(12) United States Patent
Huang et al.

(10) Patent No.: US 6,630,347 B1
(45) Date of Patent: *Oct. 7, 2003

(54) ENDOTHELIAL NOS TRANSGENIC ANIMALS AND METHODS OF USE

(75) Inventors: Paul L. Huang, Boston, MA (US); Mark C. Fishman, Newton Center, MA (US); Michael A. Moskowitz, Belmont, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/692,056

(22) Filed: Oct. 20, 2000

Related U.S. Application Data

(63) Continuation of application No. 08/818,082, filed on Mar. 14, 1997, now Pat. No. 6,310,270.
(60) Provisional application No. 60/027,362, filed on Sep. 18, 1996, and provisional application No. 60/013,525, filed on Mar. 15, 1996.

(51) Int. Cl.$^7$ .......................... C12N 5/00; C12N 5/02; C12N 5/08; C12N 15/63; C12N 15/87
(52) U.S. Cl. ...................... 435/325; 435/354; 435/366; 435/368; 435/371; 435/372; 435/455; 435/463
(58) Field of Search .............................. 800/3, 13, 18; 435/325, 354, 366, 368, 371, 372, 455, 463

(56) References Cited

U.S. PATENT DOCUMENTS

| | | | |
|---|---|---|---|
| 5,428,070 A | | 6/1995 | Cooke et al. ............... 514/557 |
| 6,310,270 B1 | * | 10/2001 | Huang et al. ................. 800/18 |

FOREIGN PATENT DOCUMENTS

| | | |
|---|---|---|
| RO | 106503 | 5/1993 |
| WO | WO 93/19166 | 9/1993 |
| WO | WO 94/28721 | 12/1994 |

OTHER PUBLICATIONS

MR Capecchi, TIG, "The new mouse genetics Altering the Genome by Gene Targeting," Mar. 1989, vol. 5, No. 3,pp. 70–76.*
Bradley et al. Modifying the mouse: Design and desire. Bio/Technology 10: 534–539, Jun. 1992.*
Gregg et al. Endothelial nitric oxide synthase (Nos3) maps to the proximal region of mouse chromosome 5. Mammalian Genome 6(2): 152, 1995.*
Janssens et al. Cloning and expression of a cDNA encoding human endothelium–derived relaxing factor/nitric oxide synthase. J. Biol. Chem. 267(21): 14519–14522, 1992.*
Lamas et al. Endothelial nitric oxide synthase: Molecular cloning and characterization of a distinct constitutive enzyme isoform. Proc. Natl. Acad. Sci. USA 89: 6348–6352, 1992.*

Moens et al. Defects in heart and lung development in compound heterozygotes for two different targeted mutations at the N–myc locus. Development 119: 485–499, 1993.*
Shalaby et al. Nature 376: 62–66, 1995.*
Sigmund, CD Viewpoint: Are studies of genetically altered mice of control? Arterioscler. Thromb. Vasc. Biol. 20: 1425–1429, 2000.*
Wall, RJ Transgenic livestock: Progress and prospects for the future. Theriogenology 45: 57–68, 1996.*
Gnanapandithen, K., et al., "Cloning and characterization of murine endothelial constitutive nitric oxide synthase," *Biochim Biophys Acta* 1308:103–106, (Aug. 1996).
Hanson, K.D. and Sedivy, J.M., "Analysis of Biological Selections for High–Efficiency Gene Targeting," *Mol. Cell. Biol.* 15:45–51, American Society for Microbiology (Jan. 1995).
Inoue, N., et al., "High–Fidelity Correction of Mutations at Multiple Chromosomal Positions by Adeno–Associated Virus Vectors," *J. Virol.* 73:7376–7380, American Society for Microbiology (Sep. 1999).
Kotkow, K.J. and Orkin, S.H., "Complexity of the erythroid transcription factor NF–E2 as revealed by gene targeting of the mouse p18 NF–E2 locus," *Proc. Natl. Acad. Sci. USA* 93:3514–3518, National Academy of Sciences (Apr. 1996).
Metcalf, D., "The Molecular Control of Hematopoiesis: Progress and Problems with Gene Manipulation," *Stem Cells* 16:314–321, AlphaMed Press (Sep. 1998).
Mohn, A. and Koller, B.H., "5. Genetic manipulation of embryonic stem cells," in: *DNA Cloning 4. A Practical Approach. Mammalian Systems. Second Edition,* Glover, D.M. and Hames, B.D., eds., Oxford University Press, Oxford, England, pp. 143–184 (Jan. 1995).
Mortensen, R.M., et al., "Production of homozygous mutant ES cells with a single targeting construct," *Mol. Cell. Biol.* 12:2391–2395, American Society for Microbiology, Inc. (1992).
Rajewsky, K., et al., "Perspective Series: Molecular Medicine in Genetically Engineered Animals," *J. Clin. Invest.* 98:600–603, American Society for Clinical Investigation, Inc. (Aug. 1996).

(List continued on next page.)

Primary Examiner—Anne-Marie Falk
(74) Attorney, Agent, or Firm—Sterne, Kessler, Goldstein & Fox PLLC

(57) ABSTRACT

This invention relates to transgenic non-human animals comprising a disrupted endothelial nitric oxide synthase gene. These animals exhibit abnormal wound-healing properties and hypertension. This invention also relates to methods of using the transgenic animals to screen for compounds having a potential therapeutic utility for vascular endothelial disorders, such as hypertension, cerebral ischemia or stroke, atherosclerosis and wound-healing activities. Moreover, this invention also relates to methods of treating a patient suffering from hypertension and wound-healing abnormalities with the compounds identified using the transgenic animals, and methods of making the transgenic animals. A method of treating a wound using nitroglycerin is also provided.

2 Claims, 24 Drawing Sheets

OTHER PUBLICATIONS

Sigmund, C.D., "Viewpoint: Are Studies in Genetically Altered Mice Out of Control?" *Arterioscler. Thromb. Vasc. Biol.* 20:1425–1429, American Heart Association, Inc. (Jun. 2000).

Silver, L.M., "6. Mutagenesis and Transgenesis," in: *Mouse Genetics. Concepts and Applications,* Silver, L.M., ed., Oxford University Press, Oxford, England, pp. 114–132 (Feb. 1995).

Smithies, O. and Maeda, N., "Gene targeting approaches to complex genetic diseases: Atherosclerosis and essential hypertension," *Proc. Natl. Acad. Sci. USA* 92:5266–5272, National Academy of Sciences (Jun. 1995).

Takahashi, J.S., et al., "Forward and Reverse Genetic Approaches to Behavior in the Mouse," *Science* 264:1724–1733, American Association for the Advancement of Science (1994).

Aji, W. et al., "L–Arginine Prevents Xanthoma Development and Inhibits Atherosclerosis in LDL Receptor Knockout Mice," *Circulation* 95: 430–437, American Heart Association, Baltimore, MD (1997).

Archer, S., "Measurement of nitric oxide in biological models" *FASEB J.* 7:349–360, The Federation of American Societies for Experimental Biology, Bethesda, MD (1993).

Babbedge, R.C. et al., "Inhibition of the rat cerebellar nitric oxide synthase by 7–nitro indazole and related substituted indazoles," *Br. J. Pharmacol.* 110:225–228, Macmillan Press Ltd., London, England (1993).

Bath, P.M.W., "The effect of nitric oxide–donating vasodilators on monocyte chemotaxis and intracellular cGMP concentrations in vitro," *Eur. J. Clin. Pharmacol.* 45:53–58, Springer–Verlag, Berlin, Germany (1993).

Beckman, J.S. et al., "Oxidative Chemistry of Peroxynitrite," *Meth. Enzymol.* 233:229–240, Academic Press, Inc., New York, NY (1994).

Beckman, J.S. et al., "Extensive Nitration of Protein Tyrosines in Human Atherosclerosis Detected by Immunohistochemistry," *Biol. Chem. Hoppe–Seyler* 375:81–88, Walter de Gruyter & Co., Berlin, Germany (1994).

Benditt, E.P. and Benditt, J.M., "Evidence for a Monoclonal Origin of Human Atherosclerotic Plaques," *Proc. Natl. Acad. Sci. USA* 70(6): 1753–1756, National Academy of Sciences of the USA, Washington, D.C. (1973).

Benrath, J. et al., "Substance P and nitric oxide mediate wound healing of ultraviolet photodamaged rat skin: evidence for an effect of nitric oxide on keratinocyte proliferation," *Neurosci. Letts.* 200:17–20, Elsevier Science Ireland Ltd., Limerick, Ireland (1995).

Boeckxstaens, G.E. et al., "Evidence for nitric oxide as mediator of non–adrenergic, non–cholinergic relaxations induced by ATP and GABA in the canine gut," *Br. J. Pharmacol.* 102:434–438, Macmillan Press Ltd., London, England (1991).

Böhme, G.A. et al., "Possible involvement of nitric oxide in long–term potentiation," *Eur. J. Pharmacol.* 199:379–381, Elsevier Science Publishers B.V., Amsterdam, Netherlands (1991).

Booth, R.F.G. et al., "Rapid development of atherosclerotic lesions in the rabbit carotid artery induced by perivascular manipulation," *Atherosclerosis* 76:257–268, Elsevier Science Publishers Ireland, Ltd., Limerick, Ireland (1989).

Bredt, D.S. et al., "Localization of nitric oxide synthase indicating a neural role for nitric oxide," *Nature* 347:768–770, Macmillan Publishers Ltd., London, England (1990).

Bredt, D.S. and Snyder, S.H., "Isolation of nitric oxide synthetase, a calmodulin–requiring enzyme," *Proc. Natl. Acad. Sci. USA* 87: 682–685, National Academy of Sciences of the USA, Washington, D.C. (1990).

Bredt, D.S. and Snyder, S.H., "Nitric Oxide, a Novel Neuronal Messenger," *Neuron* 8:3–11, Cell Press, Cambridge, MA (1992).

Bredt, D.S. and Snyder, S.H., "Nitric Oxide: A Physiologic Messenger Molecule," *Ann. Rev. Biochem.* 63:175–195, Annual Reviews, Inc., Palo Alto, CA (1994).

Breslow, J.L., "Mouse Models of Atherosclerosis," *Science* 272: 685–688, Association for the Advancement of Science, Washington, D.C. (1996).

Brinster, R.L. et al., "Somatic Expression of Herpes Thymidine Kinase in Mice following Injection of a Fusion Gene into Eggs," *Cell* 27: 223–231, MIT Press, Cambridge, MA (1981).

Bult, H. et al., "Nitric oxide as an inhibitory non–adrenergic non–cholinergic neurotransmitter," *Nature* 345:346–347, Macmillan Publishers Ltd., London, England (1990).

Burnett, A.L. et al., "Nitric Oxide: A Physiologic Mediator of Penile Erection," *Science* 257:401–403, Association for the Advancement of Science, Washington, D.C. (1992).

Busse, R. and Fleming, I., "Endothelial Dysfunction in Atherosclerosis," *J. Vasc. Res.* 33:181–194, Karger, Basel, Switzerland (1996).

Curran, R.D. et al., "Hepatocytes Produce Nitrogen Oxides from L–Arginine in Response to Inflammatory Products of Kupffer Cells," *J. Exp. Med.* 170:1769–1774, The Rockefeller University Press, New York, NY (1989).

Dalkara, T. and Moskowitz, M.A., "The Complex Role of Nitric Oxide in the Pathophysiology of Focal Cerebral Ischemia," *Brain Pathol.* 4:49–57, International Society of Neuropathology, Zurich, Germany (1994).

Darley–Usmar, V.M. et al., "The Simultaneous Generation of Superoxide and Nitric Oxide Can Initiate Lipid Peroxidation in Human Low Density Lipoprotein," *Free Rad. Res. Comm.* 17:9–20, Harwood Academic Publishers GmbH, New York, NY (1992).

Dawson, T.M. et al., "A Novel Neuronal Messenger Molecule in Brain: The Free Radical, Nitric Oxide," *Ann. Neurol.* 32:297–311, Little, Brown And Company, Boston, MA (1992).

Dawson, V.L. et al., "Nitric oxide mediates glutamate neurotoxicity in primary cortical cultures," *Proc. Natl. Acad. Sci. USA* 88:6368–6371, National Academy of Science of the USA, Washington, D.C. (1991).

Desai, K.M. et al., "Involvement of nitric oxide in the reflex relaxation of the stomach to accomodate food or liquid," *Nature* 351:477–479, Macmillan Publishers Ltd., London, England (1991).

Dimmeler, S. et al., "Nitric Oxide Causes ADP–ribosylation and Inhibition of Glyceraldehyde–3–phosphate Dehydrogenase," *J. Biol. Chem.* 267: 16771–16774, American Society for Biochemistry and Molecular Biology, Inc., Baltimore, MD (1992).

Dinerman, J.L. et al., "Endothelial nitric oxide synthase localized to hippocampal pyramidal cells: Implications for synaptic plasticity," *Proc. Natl. Acad. Sci. USA* 91:4214–4218, National Academy of Sciences of the USA, Washington, D.C. (1994).

Edelman, G.M. and Gally, J.A., "Nitric oxide: Linking space and time in the brain," *Proc. Natl. Acad. Sci. USA* 89:11651–11652, National Academy of Sciences of the USA, Washington, D.C. (1992).

Furchgott, R.F. and Zawadzki, J.V., "The obligatory role of endothelial cells in the relaxation of arterial smooth muscle by acetylcholine," *Nature* 288:373–376, Macmillan Publishers Ltd., London, England (1980).

Furchgott, R.F., "Studies on Relaxation of Rabbit Aorta by Sodium Nitrite: The Basis for the Proposal That the Acid-Activatable Inhibitory Factor from Bovine Retractor Penis is Inorganic Nitrite and the Endothelium–Derived Relaxing Factor is Nitric Oxide," in: *Vasodilation: Vascular Smooth Muscle, Peptides, Autonomic Nerves, and Endothelium*, Vanhoutte, P.M., eds., Raven Press, New York, NY, pp. 401–414 (1988).

Furchgott, R.F. and Vanhoutte, P.M., "Endothelium–derived relaxing and contracting factors," *FASEB J.* 3:2007–2018, The Federation of American Societies for Experimental Biology, Bethesda, MD (1989).

Gally, J.A. et al., "The NO hypothesis: Possible effects of a short–lived, rapidly diffusible signal in the development and function of the nervous system," *Proc. Natl. Acad. Sci. USA* 87:3547–3551, National Academy of Sciences of the USA, Washington, D.C. (1990).

Garcia, J.H. et al., "Progression from Ischemic Injury to Infarct Following Middle Cerebral Artery Occlusion in the Rat," *Am. J. Pathol.* 142: 623–635, American Society for Investigative Pathology, Bethesda, MD (1993).

Gibson, A. et al., "L–$N^G$–monomethyl arginine and L–$N^G$–nitro arginine inhibit non–adrenergic, non–cholinergic relaxation of the mouse anococcygeus muscle," *Br. J. Pharmacol.* 99:602–606, Macmillan Press Ltd., London, England (1990).

Gillespie, J.S. et al., "The effects of L–arginine and $N^G$–monomethyl L–arginine on the response of the rat anococcygeus muscle to NANC nerve stimulation," *Br. J. Pharmacol.* 98:1080–1082, Macmillan Press Ltd., London, England (1989).

Haley, J.E. et al., "The Role of Nitric Oxide in Hippocampal Long–Term Potentiation," *Neuron* 8:211–216, Cell Press, Cambridge, MA (1992).

Hamberg, L.M. et al., "Time Effects of L–Arginine on Cerebral Hemodynamics and Ischemic Volume During Acute Focal Ischemia Demonstrated by Dynamic MRI," *Proc. Soc. Mag. Res. Med.* 1:397, Society of Magnetic Resonance in Medicine, New York, NY (1993).

Heck, D.E. et al., "Epidermal Growth Factor Suppresses Nitric Oxide and Hydrogen Peroxide Production by Keratinocytes," *J. Biol. Chem.* 267: 21277–21280, American Society for Biochemistry and Molecular Biology, Inc., Baltimore, MD (1992).

Hibbs, J.B. et al., "Nitric Oxide: A Cytotoxic Activated Macrophage Effector Molecule," *Biochem. Biophys. Res. Comm.* 157(1):87–94, Academic Press, Inc., Orlando, FL (1988).

Huang, P.L. et al., "Targeted Disruption of the Neuronal Nitric Oxide Synthase Gene," *Cell* 175:1273–1286, Cell Press, Cambridge, MA (1993).

Huang, P.L. et al., et al., "Hypertension in mice lacking the gene for endothelial nitric oxide synthase," *Nature* 377:239–242, Macmillan Publishers, Ltd., London, England (1995).

Huang, P.L. et al., "Genetic analysis of nitric oxide synthase isoforms: targeted mutation in mice," *J. Mol. Med.* 74:415–421, Springer–Verlag, Berlin, Germany (1996).

Huang, Z. et al., "Effects of Cerebral Ischemia in Mice Deficient in Neuronal Nitric Oxide Synthase," *Science* 265:1883–1885, Association for the Advancement of Science, Washington, D.C. (1994).

Huang, Z. et al., "Focal cerebral ischemia in mice deficient in either endothelial (eNOS) or neuronal nitric oxide (nNos) synthase," *Stroke* 27(1):173, Abstract No. 41, Lippincott Williams & Wilkins, Baltimore, MD (Jan. 1996).

Huang, Z. et al., "bFGF ameliorates focal ischemic injury by blood flow–independent mechanisms in eNOS mutant mice," *Am. J. Physiol.* 272:H1401–H1405, American Physiological Society, Bethesda, MD (1997).

Iadecola, C. et al., "Nitric Oxide Synthase Inhibition and Cerebrovascular Regulation," *J. Cereb. Blood Flow Metabol.* 14:175–192, International Society of Cerebral Blood Flow and Metabolism, New York, NY (1994).

Ignarro, L.J. et al., "Endothelium–derived relaxing factor produced and released from artery and vein is nitric oxide," *Proc. Natl. Acad. Sci. USA* 84:9265–9269, National Academy of Sciences of the USA, Washington, D.C. (1987).

Ignarro, L.J., "Endothelium–derived nitric oxide: actions and properties," *FASEB J.* 3:31–36, The Federation of American Societies for Experimental Biology, Bethesda, MD (1989).

Ishibashi, S. et al., "Hypercholesterolemia in Low Density Lipoprotein Receptor Knockout Mice and its Reversal by Adenovirus–mediated Gene Delivery," *J. Clin. Invest.* 92:883–893, The Rockefeller University Press, New York, NY (1993).

Janssens, S.P. et al., "Cloning and Expression of a cDNA Encoding Human Endothelium–derived Relaxing Factor/Nitric Oxide Synthase," *J. Biol. Chem.* 267(21):14519–14522, American Society for Biochemistry and Molecular Biology, Inc., Baltimore, MD (1992).

Janssens, S.P. et al., "Cloning and expression of a CDNA encoding human endothelium–derived relaxing factor/nitric oxide synthase, Correction," *J. Biol. Chem.* 267(37):22694, American Society for Biochemistry and Molecular Biology, Inc., Baltimore, MD (1992).

Kano, M. et al., "Parasympathetic Denervation of Rat Pial Vessels Significantly Increases Infarction Volume Following Middle Cerebral Artery Occlusion," *J. Cereb. Blood Flow Metabol.* 11:628–637, International Society of Cerebral Blood Flow and Metabolism, New York, NY (1991).

Kaufman, P.B. et al., "Gene Transfer and Expression in Animals," Chapter 15 in: *Handbook of Molecular and Cellular Methods in Biology and Medicine*, Kaufman, P.B. et al., eds., CRC Press, Boca Raton, FL, pp. 329–365 (1995).

Kidd, E.J. et al., "Autoradiographic Distribution of [$^3$H] L–$N^G$–Nitro–arginine Binding in Rat Brain," *Neuropharmacol.* 34:63–73, Pergamon Press, Oxford, England (1995).

Knowles, R.G. and Moncada, S., "Nitric oxide as a signal in blood vessels," *TIBS* 17:399–402, International Union of Biochemistry and Elsevier Trends Journal, Cambridge, England (1992).

Kockx, M.M. et al., "The Endothelium During Cuff–Induced Neointima Formation in the Rabbit Carotid Artery," *Arterioscler. Thromb.* 13:1874–1884, American Heart Association, Baltimore, MD (1993).

Koketsu, N. et al., "Chronic Parasympathetic Sectioning Decreases Regional Cerebral Blood Flow During Hemmorrhagic Hypotension and Increases Infarct Size After Middle Cerebral Artery Occlusion in Spontaneously Hypersensitive Rats," *J. Cereb. Blood Flow Metab.* 12:613–620, International Society of Cerebral Blood Flow and Metabolism, New York, NY (1992).

Kots, A.Y. et al., "Nitroprusside stimulates the cysteine–specific mono(ADP–ribosylation) of glyceraldehyde–3–phosphate dehydrogenase from human erythrocytes," *FEBS Letts.* 300:9–12, Federation of European Biochemical Societies, Amsterdam, Netherlands (1992).

Kubes, P. et al., "Nitric oxide: An endogenous modulator of leukocyte adhesion," *Proc. Natl. Acad. Sci. USA* 88:4651–4655, National Academy of Sciences of the USA, Washington, D.C. (1991).

Kurose, I. et al., "Modulation of Ischemia/Reperfusion–Induced Microvascular Dysfunction by Nitric Oxide," *Circ. Res.* 74:376–382, American Heart Association, Baltimore, MD (1994).

Lamas, S. et al., "Endothelial nitric oxide synthase: Molecular cloning and characterization of a distinct constitutive enzyme isoform," *Proc. Natl. Acad. Sci. USA* 89:6348–6352, National Academy of Sciences of the USA, Washington, D.C. (1992).

Leitinger, N. et al., "The Effect of NO/EDFR and Monocytes/Macrophages on LDL—Oxidation," *J. Physiol. Pharmacol.* 46:385–408, Polish Physiological Society, Krakow, Poland (1995).

Lindner, V. et al., "Mouse Model of Arterial Injury," *Circ. Res.* 73:792–796, American Heart Association, Baltimore, MD (1993).

Lowenstein, C.J. and Snyder, S.H., "Nitric Oxide, A Novel Biological Messenger," *Cell* 70:705–707, Cell Press, Cambridge, MA (1992).

Malinski, T. et al., "Nitric Oxide Measured by a Porphyrinic Microsensor in Rat Brain After Transient Middle Cerebral Artery Occlusion," *J. Cereb. Blood Flow Metabol.* 13:355–358, International Society of Cerebral Blood Flow and Metabolism, New York, NY (1993).

Marletta, M.A., "Nitric oxide: biosynthesis and biological significance," *TIBS* 14:488–492, International Union of Biochemistry and Elsevier Trends Journal, Cambridge, England (1989).

Marletta, M.A., "Nitric Oxide Synthase Structure and Mechanism," *J. Biol. Chem.* 268:12231–12234, American Society for Biochemistry and Molecular Biology, Inc., Baltimore, MD (1993).

Mayer, B. et al., "Molecular Mechanisms of Inhibition of Porcine Brain Nitric Oxide Synthase by the Antinociceptive Drug 7–Nitro–Indazole," *Neuropharmacol.* 33:1253–1259, Pergamon Press, Oxford, England (1994).

McDonald, L.J. and Moss, J., "Stimulation by nitric oxide of an AND linkage to glyceraldehyde–3–phosphate dehydrogenase," *Proc. Natl. Acad. Sci. USA* 90:6238–6241, National Academy of Sciences of the USA, Washington, D.C. (1993).

Michel, A.D. et al., "Characterization of the binding of [$^3$H]–L–N$^G$–nitro–arginine in rat brain," *Br. J. Pharmacol.* 109:287–288, Macmillan Press, Ltd., London, England (1993).

Miyahara, K. et al., "Cloning and structural characterization of the human endothelial nitric–oxide–synthase gene," *Eur. J. Biochem.* 223:719–726, Blackwell Science Ltd., Berlin, Germany (1994).

Moncada, S. et al., "Nitric Oxide: Physiology, Pathophysiology, and Pharmacology," *Pharmacol. Rev.* 43:109–142, American Society for Pharmacology and Experimental Therapeutics, Bethesda, MD (1991).

Moncada, S., "The 1991 Ulf von Euler Lecture: The L–arginine:nitric oxide pathway," *Acta Physiol. Scand.* 145:201–207, Blackwell Scientific Publications, Oxford, England (1992).

Moore, P.K. et al., "7–Nitro indazole, and inhibitor of nitric oxide synthase, exhibits anti–nociceptive activity in the mouse without increasing blood pressure," *Br. J. Pharmacol.* 108:296–297, Macmillan Press Ltd., London, England (1993).

Moore, P.K. et al., "Characterization of the novel nitric oxide synthase inhibitor 7–nitro indazole and related indazoles: antinociceptive and cardiovascular effects," *Br. J. Pharmacol.* 110:219–224, Macmillan Press Ltd., London, England (1993).

Mooradian, D.L. et al., "Nitric Oxide (NO) Donor Molecules: Effect of NO Release Rate on Vascular Smooth Muscle Cell Proliferation In Vitro," *J. Cardiovasc. Pharmacol.* 25:674–678, Lippincott Williams & Wilkins, Hagerstown, MD (1995).

Morikawa, E. et al., "L–Arginine Infusion Promotes Nitric Oxide–Dependent Vasodilation, Increases Regional Cerebral Blood Flow, and Reduces Infarction Volume in the Rat," *Stroke* 25:429–435, American Heart Association, Baltimore, MD (1994).

Morikawa, E. et al., "Therapeutic Potential of L–Arginine, a Precursor of Nitric Oxide, in Focal Cerebral Ischemia," Chapter 28 in : *The Human Brain Circulation: Functional Changes in Disease,* Bevan, R.D. and Bevan, J.A., eds, Humana Press, pub., Totowa, pp. 373–387 (1994).

Moroi, M. et al., "Mice Mutant in Endothelial Nitric Oxide Synthase: Vessel Growth and Response to Injury," *Circulation* 94(*Suppl. 1*):I–154, Abstract N.: 0890, American Heart Association, Baltimore, M D (1996).

Murphy, S. et al., "Synthesis of nitric oxide in CNS glial cells," *TINS* 16:323–328, Elsevier Science Publishers B.V., Amsterdam, Netherlands (1993).

Nathan, C., "Nitric oxide as a secretory product of mammalian cells," *FASEB J.* 6:3051–3064, The Federation of American Societies for Experimental Biology, Bethesda, MD (1992).

Nathan, C. and Xie, Q., "Nitric Oxide Synthases: Roles, Tolls, and Controls," *Cell* 78:915–918, Cell Press, Cambridge, MA (1994).

Nozaki, K. et al., "Possible Origins and Distributions of Immunoreactive Nitric Oxide Synthase–Containing Nerve Fibers in Cerebral Arteries," *J. Cereb. Blood Metab.* 13:70–79, International Society of Cerebral Blood Flow and Metabolism, New York, NY (1993).

O'Dell, T.J. et al., "Tests of the roles of two diffusible substances in long–term potentiation: Evidence for nitric oxide as a possible early retrograde messenger," *Proc. Natl. Acad. Sci. USA* 88:11285–11289, National Academy of Sciences of the USA, Washington, D.C. (1991).

O'Dell, T.J. et al., "Endothelial NOS and the Blockade of LTP by NOS Inhibitors in Mice Lacking Neuronal NOS," *Science* 265:542–546, Association for the Advancement of Science, Washington, D.C. (1994).

Palmer, R.M.J. et al., "Nitric oxide release accounts for the biological activity of endothelium–derived relaxing factor," *Nature* 327:524–526, Macmillan Publishers, Ltd., London, England (1987).

Palmer, R.M.J. et al., "Vascular endothelial cells synthesize nitric oxide from L–arginine," *Nature* 333:664–666, Macmillan Publishers, Ltd., London, England (1988).

Peng, H. et al., "Induction and Stabilization of IκBα by Nitric Oxide Mediates Inhibition of NF–κB," *J. Biol. Chem.* 270:14214–14219, American Society for Biochemistry and Molecular Biology, Inc., Baltimore, MD (1995).

Plump, A.S. et al., "Severe Hypercholesterolemia and Atherosclerosis in Apolipoprotein E–Deficient Mice Created by Homologous Recombination in ES Cells," *Cell* 71:343–353, Cell Press, Cambridge, MA (1992).

Purcell–Huynh, D.A. et al., "Transgenic Mice Expressing High Levels of Human Apolipoprotein B Develop Severe Atherosclerotic Lesions in Response to a High–Fat Diet," *J. Clin. Invest.* 95:2246–2257, The Rockefeller University Press, New York, NY (May 1995).

Radomski, M.W. et al., "An L–arginine/nitric oxide pathway present in human platelets regulates aggregation," *Proc. Natl. Acad. Sci. USA* 87: 5193–5197, National Academy of Sciences of the USA, Washington, D.C. (1990).

Radomski, M.W. et al., "Modulation of platelet aggregation by an L–arginine–nitric oxide pathway," *TiPS* 12:87–88, Elsevier Science Publishers B.V., Amsterdam, Netherlands (1991).

Radomski, M.W. and Salas, E., "Nitric oxide—Biological mediator, modulator and factor of injury: its role in the pathogenesis of atherosclerosis," *Atherosclerosis* 118 (*Suppl.*):S69–S80, Elsevier Science Ireland, Ltd., Limerick, Ireland (1995).

Rajfer, J. et al., "Nitric Oxide as a Mediator of Relaxation of Relaxation of the Corpus Cavernosum In Response to Nonadrenergic, Noncholinergic Neurotransmission," *New England J. Med.* 326:90–94, Massachusetts Medical Society, Boston, MA (1992).

Ramagopal, M.V. and Leighton, H.J., "Effects of $N^G$–monomethyl–L–arginine on field stimulation–induced decreases in cytosolic $Ca^{2+}$ levels and relaxation in the rat anococcygeus muscle," *Eur. J. Pharmacol.* 174:297–299, Elsevier Science Publishers B.V., Amsterdam, Netherlands (1989).

Rees, D.D. et al., "Characterization of three inhibitors of endothelial nitric oxide synthase in vitro and in vivo," *Br. J. Pharmacol.* 101:746–752, Macmillan Press, Ltd., London, England (1990).

Ross, R., "Cell Biology of Atherosclerosis," *Ann. Rev. Physiol.* 57:791–804, Annual Reviews, Inc., Palo Alto, CA (1995).

Ross, R., "Genetically modified mice as models of transplant atherosclerosis," *Nature Med.* 2:527–528, Nature Publishing Company, New York, NY (1996).

Rutherford, R.A.D. et al., "Nitric oxide synthase in human placenta and umbilical cord from normal, intrauterine growth–retarded and pre–eclamptic pregnancies," *Br. J. Pharmacol.* 116:3099–3109, Macmillan Press, Ltd., London, England (1995).

Schmidt, H.H.H.W. et al., "Mapping of Neural Nitric Oxide Synthase in the Rat Suggests Frequent Co–localization with NADPH Diaphorase but Not with Soluble Guanylyl Cyclase, and Novel Paraneural Functions for Nitrinergic Signal Transduction," *J. Histochem. Cytochem.* 40:1439–1456, The Histochemical Society, New York, NY (1992).

Schmidt, H.H.H.W. and Walter, U., "NO at Work," *Cell* 78:919–925, Cell Press, Cambridge, MA (1994).

Schulz, J.B. et al., "Inhibition of Neuronal Nitric Oxide Synthase by 7–Nitroindazole Protects Against MPTP–Induced Neurotoxicity in Mice," *J. Neurochem.* 64:936–939, Lippincott Williams & Wilkins, Hagerstown, MD (1995).

Schulz, J.B. et al., "Blockade of Neuronal Nitric Oxide Synthase Protects against Excitotoxicity in vivo," *J. Neurosci.* 15:8419–8429, Society for Neuroscience, Washington, D.C. (1995).

Schuman, E.M. and Madison, D.V., "A Requirement for the Intercellular Messenger Nitric Oxide in Long–Term Potentiation," *Science* 254:1503–1506, Association for the Advancement of Science, Washington, D.C. (1991).

Schwartz, S.M. et al., "The Intima: Soil for Atherosclerosis and Restenosis," *Circ. Res.* 77:445–465, American Heart Association, Baltimore, MD (1995).

Shibuki, K. and Okada, D., "Endogenous nitric oxide release required for long–term synaptic depression in the cerebellum," *Nature* 349:326–328, Macmillan Publishers, Ltd., London, England (1991).

Snyder, S.H. and Bredt, D.S., "Nitric oxide as a neuronal messenger," *TiPS* 12:125–128, Elsevier Science Publishers B.V., Amsterdam, Netherlands (1991).

Snyder, S.H., "Nitric Oxide: First in a New Class of Neurotransmitters?," *Science* 257:494–496, Association for the Advancement of Science, Washington, D.C. (1992).

Snyder, S.H., "No endothelial NO," *Nature* 377:196–197, Macmillan Publishers Ltd., London, England (1995).

Sobey, C.G. et al., "Evidence That Expression of Inducible Nitric Oxide Synthase in Response to Endotoxin Is Augmented in Atherosclerotic Rabbits," *Circ. Res.* 77:536–543, American Heart Association, Baltimore, MD (1995).

Toda, N. and Okamura, T., "Possible Role of Nitric Oxide in Transmitting Information from Vasodilator Nerve to Cerebroarterial Muscle," *Biochem. Biophys. Res. Comm.* 170:308–313, Academic Press, Inc., Orlando, FL (1990).

Topors, M. et al., "Endothelin–1 Stimululates NO Release from Proliferating Vascular Smooth Muscle Cells: Evidence for Constitutive Nitric Oxide Synthase Expression," *Circulation* 92(*Suppl. 1*):I–564, Abstract No. 2697, American Heart Association, Baltimore, MD (1995).

Tøttrup, A. et al., "Nitric oxide mediating NANC inhibition in opossum lower esophageal sphincter," *Am. J. Physiol.* 260:G385–G389, American Physiological Society, Bethesda, MD (1991).

Tybulewicz, V.L.J. et al., "Neonatal Lethality and Lymphopenia in Mice with a Homozygous Disruption of the c–abl Proto–Oncogene," *Cell* 65:1153–1163, Cell Press, Cambridge, MA (1991).

van den Maagdenberg, A.M.J.M. et al., "Transgenic Mice Carrying the Apolipoprotein E3–Leiden Gene Exhibit Hyperlipoproteinemia," *J. Biol. Chem.* 268: 10540–10545, American Society for Biochemistry and Molecular Biology, Inc., Baltimore, MD (1993).

Vincent, S.R. and Kimura, H., "Histochemical Mapping of Nitric Oxide Synthase in the Rat Brain," *Neurosci.* 46:755–784, Society For Neuroscience, Washington, D.C. (1992).

Wallace, M.N. and Fredens, K., "Activated astrocytes of the mouse hippocampus contain high levels of NADPH–diaphorase," *NeuroReport* 3:953–956, Rapid Communications of Oxford Ltd., Oxford, England (1992).

Wilcox. J.N. et al., "Expression of Multiple Nitric Oxide Synthase Isoforms in Human Aortic Fatty Streaks and Advanced Atherosclerotic Plaques," *Circulation* 90(4):I–298, Abstract No. 1600, American Heart Association, Baltimore, MD.

Yamamoto, S. et al., "Inhibition of Nitric Oxide Synthesis Increases Focal Ischemic Infarction in Rat," *J. Cereb. Blood Flow Metabol.* 12:717–726, International Society of Cerebral Blood Flow and Metabolism, New York, NY (1992).

Yoshida, T. et al., "The NOS Inhibitor, 7–Nitroindazole, Decreases Focal Infarct Volume but not the Response to Topical Acetylcholine in Pial Vessels," *J. Cereb. Blood Flow Metabol.* 14:924–929, International Society of Cerebral Blood Flow and Metabolism, New York, NY (1994).

Yoshida, T. et al., "Induction of nitric oxide synthase activity in rodent brain following middle cerebral artery occlusion," *Neurosci. Letts.* 194:214–218, Elsevier Science Ireland Ltd., Limerick, Ireland (Jul. 1995).

Zhang, F. and Iadecola, C., "Nitroprusside improves blood flow and reduces brain damage after focal ischemia," *NeuroReport* 4:559–562, Rapid Communications of Oxford Ltd., Oxford, England (1993).

Zhang, F. et al., "Nitric Oxide Donors Increase Blood Flow and Reduce Brain Damage in Focal Ischemia: Evidence that Nitric Oxide is Beneficial in the Early Stages of Cerebral Ischemia," *J. Cereb. Blood Flow Metabol.* 14:217–226, International Society of Cerebral Blood Flow and Metabolism, New York, NY (1994).

Zhang, J. and Snyder, S.H., "Nitric oxide stimulates auto–ADP–ribosylation of glyceraldehyde–3–phosphate dehydrogenase," *Proc. Natl. Acad. Sci. USA* 89:9382–9385, National Academy of Sciences of the USA, Washington, D.C. (1992).

Zhang, S.H. et al., "Spontaneous Hypercholesterolemia and Arterial Lesions in Mice Lacking Apolipoprotein E," *Science* 258:468–471, Association for the Advancement of Science, Washington, D.C. (1992).

Zhang, Z.G. et al., "Selective Neuronal NOS Inhibitor Decreases Infarct Volume After Transient Focal Cerebral Ischemia in Rats," *J. Cereb. Blood Flow Metab.* 15(Supp. 1):S90, International Society of Cerebral Blood Flow and Metabolism, New York, NY (Jul. 1995).

Bradley, A. et al., "Modifying the mouse: Design and Desire," *Biotechnol.* 10:534–539, Nature Publishing Co., New York, NY (1992).

Campbell, H.S. and Wilmut, I., "Totipotency or multipotentiality of cultured cells: Applications and progress," *Theriogenology* 47:63–72, Elsevier Science Inc., Stoneham, MA (1997).

Gregg, A.R. et al., "Endothelial nitric oxide synthase (Nos3) maps to the proximal region of mouse Chromosome 5," *Mammalian Genome* 6:152, Springer International, New York, NY (1995).

English language abstract of RO 106503 B1, Document No. AN1, CaPlus Accession No. 1998:402473 (1998).

Campbell, K.H.S. et al., "Sheep cloned by nuclear transfer from a cultured cell line," *Nature* 380:64–66, Macmillan Publishing Ltd., London, England (1996).

Niemann, H. and Reichelt, B., "Manipulating early pig embryos," *J. Reprod. Fertil.* 48(Suppl.):75–94, Journals of Reproduction and Fertility Ltd., London, England (1993).

Schoonjans, L. et al., "Pluripotential Rabbit Embryonic Stem (ES) Cells Are Capable of Forming Overt Coat Color Chimeras Following Injection Into Blastocysts," *Mol. Repro. Develop.* 45:439–443, Wiley–Liss, Inc., New York, NY (1996).

Sims, M. and First, N.L., "Production of calves by transfer of nuclei from cultured inner cell mass cells," *Proc. Natl. Acad. Sci. USA* 90:6143–6147, National Academy of Sciences of the USA, Washington, D.C. (1993).

Stice, S.L. et al., "Pluripotent Bovine Embryonic Cell lines Direct Embryonic Development Following Nuclear Transfer," *Biol. Repro.* 54:100–110, Society for the Study of Reproduction, New York, NY (1996).

Wheeler, M.B., "Development and Validation of Swine Embryonic Stem Cells: a Review," *Reprod. Fertil. Dev.* 6:563–568, Commonwealth Scientific and Industrial Research Organisation, East Melbourne, Australia (1994).

\* cited by examiner

SEQUENCE LISTING

<160> NUMBER OF SEQ ID NOS: 6

<210> SEQ ID NO 1
<211> LENGTH: 26
<212> TYPE: DNA
<213> ORGANISM: Oligonucleotide

<400> SEQUENCE: 1
ccttagagag taaggaaggg ggcggg                                  26

<210> SEQ ID NO 2
<211> LENGTH: 28
<212> TYPE: DNA
<213> ORGANISM: Oligonucleotide

<400> SEQUENCE: 2
gggccgatca ttgacggcga gaatgatg                                28

<210> SEQ ID NO 3
<211> LENGTH: 25
<212> TYPE: DNA
<213> ORGANISM: Oligonucleotide

<400> SEQUENCE: 3
gggctccctc cttccggctg ccacc                                   25

<210> SEQ ID NO 4
<211> LENGTH: 24
<212> TYPE: DNA
<213> ORGANISM: Oligonucleotide

<400> SEQUENCE: 4
ggatccctgg aaaaggcggt gagg                                    24

```
<210> SEQ ID NO 5
<211> LENGTH: 24
<212> TYPE: DNA
<213> ORGANISM: Oligonucleotide

<400> SEQUENCE: 5
atcaggaacc tgaagcccca ggac                                              24

<210> SEQ ID NO 6
<211> LENGTH: 24
<212> TYPE: DNA
<213> ORGANISM: Oligonucleotide

<400> SEQUENCE: 6
tgttgccaga tttctctgca cggt                                              24
```

ENDOTHELIAL NOS TRANSGENIC ANIMALS AND METHODS OF USE

CROSS-REFERENCES TO RELATED APPLICATION

This application is a continuation of application Ser. No. 08/818,082, filed on Mar. 14, 1997, now U.S. Pat. No. 6,310,270 which claims the benefit of U.S. Provisional Application No. 60/013,525 filed Mar. 15, 1996, and U.S. Provisional Application No. 60/027,362, filed Sep. 18, 1996. The content of these provisional applications are expressly incorporated herein by reference.

BACKGROUND OF THE INVENTION

STATEMENT AS TO RIGHTS TO INVENTIONS MADE UNDER FEDERALLY-SPONSORED RESEARCH AND DEVELOPMENT

Part of the work performed during the development of this invention was supported by U.S. Government funds. The U.S. Government may have certain rights in this invention.

1. Field of the Invention

This invention relates to transgenic non-human animals comprising a disrupted endothelial nitric oxide synthase gene. This invention also relates to methods of using these transgenic animals to screen compounds for activity against vascular endothelial disorders such as hypertension, stroke, and atherosclerosis, as well as for wound healing activity; methods of treating a patient suffering from a vascular endothelial disorder; methods of making the transgenic animals; and cell lines comprising a disrupted eNOS gene.

2. Related Art

In 1980, Furchgott and Zawadzzi first proposed the existence of endothelium derived relaxing factor or EDRF, later identified as nitric oxide. Furchgott (1980); Furchgott (1988); Ignarro (1988); Palmer (1987). Nitric oxide is an important messenger molecule produced by endothelial cells, neurons, macrophages, and other tissues. Marietta (1989); Moncada (1991); Nathan (1992); Snyder (1992); and Dawson et al. (1992). Since nitric oxide is a gas with no known storage mechanism, it diffuses freely across membranes and is extremely labile. Nitric oxide has a biological half-life on the order of seconds.

Nitric oxide exhibits several biochemical activities. This compound can bind to and activate soluble guanyl cyclase, resulting in increased cGMP levels. Nitric oxide also modifies a cysteine residue in glyceraldehyde-3-phosphate dehydrogenase by adenosine diphosphate ribosylation, Zhang & Snyder (1992), Katz et al. (1992), and Dimmeler et al. (1992), or S-nitrosylation via NAD interactions, McDonald & Moss (1993). Nitric oxide also binds to a variety of iron- and sulphur-containing proteins, Marletta (1993), and may have other modes of action as well.

Nitric oxide formation is catalyzed by the nitric oxide synthase enzymes (NOS). These enzymes act by producing nitric oxide from the terminal guanidino nitrogen of arginine, with the stoichiometric production of citrulline. There are several NOS isoforms encoded by separate genes. Marletta (1993), and Lowenstein & Snyder (1992). The various NOS isoforms are about 50–60% homologous overall. Some forms of NOS are found in most tissues. The different NOS isoforms: neuronal NOS (nNOS), macrophage NOS (iNOS), and endothelial NOS (eNOS), are now known as type I NOS, type II NOS and type III NOS, respectively. The properties of these NOS isoforms are summarized in the following Table:

| Property | Type I NOS | Type II NOS | Type III NOS |
|---|---|---|---|
| Common name | nNOS | iNOS | eNOS |
| Typical cell | neurons | macrophages | endothelium |
| Other sites of expression | smooth muscle | endothelium smooth muscle | smooth muscle neurons |
| Expression | constitutive | inducible | constitutive |
| Regulation | Ca/CaM | transcription | Ca/CaM |
| Output | moderate (nM to $\mu$M) | high ($\mu$M) | low (pM to nM) |
| Function | signalling | toxin | signalling |

The ubiquitous presence of blood vessels and nerves means that the endothelial and neuronal isoforms may be present in most tissues. The expression of the endothelial and neuronal isoforms can also be induced in cells that normally do not express them. The sequence of these isoforms have been published or are available in Genbank under the following accession numbers:

| | Species: | | | |
|---|---|---|---|---|
| Gene: | Man | Rat | Mouse | Cow |
| Neuronal (type I) | U17327 D16408 L02881 | X59949 | D14552 | |
| Macrophage (type II) | L09210 X85759-81 U18334 U31511 U20141 U05810 X73029 L24553 | D14051 D83661 U26686 U16359 D44591 X76881 U02534 L12562 | M87039 U43428 L23806 L09126 M92649 M84373 | U18331 U14640 |
| Endothelial (type III) | X76303-16 L26914 L23210 L10693 M95296 M93718 | U18336 U28933 | | M89952 L27056 M95674 M99057 M89952 |

Each of these sequences are expressly incorporated herein by reference.

In blood vessels, the endothelial NOS isoform mediates endothelium-dependent vasodilation in response to acetylcholine, bradykinin, and other mediators. Nitric oxide also maintains basal vascular tone and regulates regional blood flow. Nitric oxide levels increase in response to shear stress, i.e., forces on the blood vessels in the direction of blood flow, and to mediators of inflammation. Furchgott & van Houtte (1989); Ignarro (1989).

In the immune system, the macrophage isoform is produced by activated macrophages and neutrophils as a cytotoxic agent. Nitric oxide produced in these cells targets tumor cells and pathogens. Hibbs et al. (1988); Nathan (1992); and Marletta (1989).

In the nervous system, the neuronal NOS isoform is localized to discrete populations of neurons in the cerebellum, olfactory bulb, hippocampus, cortex, striatum, basal forebrain, and brain stem: Bredt et al. (1990). NOS is also concentrated in the posterior pituitary gland, in the superoptic and paraventricular hypothalamic nuclei, and in discrete ganglion cells of the adrenal medulla Id. The widespread cellular localization of neuronal NOS and the short half-life and diffusion properties of nitric oxide suggest that it plays a role in nervous system morphogenesis and synaptic plasticity.

During development, NO may influence activity-dependent synaptic pruning, apoptosis, and the establishment of the columnar organization of the cortex. Gaily et al. (1990), Edelman & Gally (1992). Two forms of long-term synaptic modulation, long-term depression of the cerebellum, Shibuki & Okada (1991), and long-term potentiation (LTP) in the hippocampus, are sensitive to inhibitors of NOS. Bohme et al. (1991); Haley et al. (1992); O'Dell et al. (1991); Schuman & Madison (1991). Thus, nitric oxide may serve as a retrograde neurotransmitter to enhance synaptic function due to correlated firing of pre-and postsynaptic cells.

In the peripheral nervous system, nitric oxide mediates relaxation of smooth muscle. Smooth muscle relaxation in the gut, important to adaptation to a bolus of food and peristalsis, depends upon inhibitory non adrenergic, noncholinergic nerves that mediate their effects via nitric oxide. Boeckvstaens et al. (1991); Bult et al. (1990); Desai et al. (1991); Gillespie et al. (1989); Gibson et al. (1990); Ramagopal & Leighton (1989); Tottrup et al. (1991). NOS-containing neurons also innervate the corpus carvornosa of the penis, Burnett et al. (1992); Rajfer et al. (1992), and the adventitial layer of cerebral blood vessels. Nozaki et al. (1993); Toda & Okamura (1990). Stimulation of these nerves can lead to penile erection and dilation of cerebral arteries, respectively. These effects are blocked by inhibition of NOS.

Various biological roles of NO are described by Schmidt & Walter (1994); Nathan & Xie (1994); and Snyder (1995). The major roles of nitric oxide include:
  (1) vasodilation or vasoconstriction with resulting change in blood pressure and blood flow;
  (2) neurotransmission in the central and peripheral nervous system, including mediation of signals for normal gastrointestinal motility; and
  (3) defense against pathogens like bacteria, fungus, and parasites due to the toxicity of high levels of NO to pathogenic organisms.

Recently, a role for NO has been proposed in the pathophysiology of cerebral ischemia, one form of vascular endothelial disorder. Iadecola et al. (1994); Dalkara and Moskowitz (1994). Since NO is diffuisible, short-lived, and reactive free radical gas that is difficult to measure in vivo, Archer (1993), most studies examining ischemic outcomes have based their conclusions on results following NOS inhibition by arginine analogues such as nitro-L-arginine or nitro-L-arginine methyl ester. These inhibitors, however, lack enzyme selectivity and block multiple isoforms. Rees et al. (1990). This nonselectivity might account in part for the discrepant outcomes after administration of NOS inhibitors following middle cerebral artery (MCA) occlusion.

Atherosclerosis is another form of a vascular endothelial disorder. This disease, a major cause of mobidity and mortality, is progressive beginning many years before the onset of overt symptoms. During the development of atherosclerosis, biochemical, cellular, and hemodynamic forces drive change in blood vessel walls, which ultimately leads to endothelial disfunction, cellular proliferation, recruitment of endothelial cells, and accumulation of oxidized LDL. Ross (1995). The cellular and molecular mechanisms that underlie these processes are complex. Rodent models offer the ability to study the contribution of individual genes, alone or in combination, to the molecular events in atherosclerosis. Breslow (1996); Ross (1996).

Cells within atherosclerotic plaques are monoclonal or oligoclonal in origin, indicating that intimal proliferation plays an important role in the development of lesions. Benditt (1973). Intimal proliferation also occurs as a common response to arterial injury of many kinds, regardless of whether the injury is luminal or advertitial. Schwartz (1995). Thus, niodels of vessel injury are relevant to atherosclerosis. For example, in a cuff model of adventitial injury, Booth et al. (1989); Kockx et al (1993), signals from the adventitia stimulate formation of a neointimal layer in a predictable manner. This model leaves the endothelium intact, so that the role of endothelial gene products can be studied. In a filament model of endothelial injury, Lindner (1993), the endothelium is physically removed, resulting in proliferation of medial smooth muscle cells. The rate at which endothelial cells resurface the injured areas can be quantitated.

In another type of atherosclerosis model, defined genetic mutations are used to increase the propensity of mice to atherosclerosis. Breslow (1996); Ross (1996). For example, mutant mice that form atherosclerotic lesions include apoE gene knockout mice, Plumb (1992); Zhang (1992); apoE Leiden mutation, van der Maagdenberg (1993); LDL receptor gene knockout mice, Ishibayashi (1993); and transgenic mice expressing the human apoB gene, Purcell-Huynh (1995). Of these, apoE knockout mice are an attractive atherosclerosis model, since they develop lesions on a low cholesterol, low-fat diet, and do not require the addition of cholic acid. These knockout mice develop fatty streaks that progress to fibrous plaques at branchpoints of major vessels, similar to human lesions. The rate and extent of lesion formation and its pathological severity can be quantitated. For example, a Western diet results in faster progression of the disease and formation of larger plaques than a low-cholesterol diet. Thus, the apoE knockout mice exhibit many aspects of human atherosclerosis.

Nitric oxide has physiological effects in blood vessels that may prevent atherosclerosis, such as suppression of smooth muscle proliferation, Mooradian (1995), inhibition of platelet aggregation and adhesion, Radomski (1991), and inhibition of leukocyte activation and adhesion, Bath (1993); Lefer (1993). It has also been recently reported that arginine inhibits atherosclerosis in LDL receptor mutant mice. Aji (1997).

While certain physiological effects of nitric oxide may prevent atherosclerosis, other studies suggest that excessive nitric oxide production may contribute to the development of atherosclerosis. Busse (1976); Leitinger (1995); Radomski (1995). Evidence for a pro-atherogenic role for nitric oxide includes several different findings. First, expression of iNOS and nNOS isoforms can be induced in atherosclerotic vessels. Aji (1997); Sobey (1995); Topors (1995); Wilcox (1994). Second, human atherosclerotic lesions contain nitrotyrosine, suggesting that peroxynitrite is formed in atherosclerotic lesions. See Beckman (1994b). Peroxynitrite is formed by the reaction of nitric oxide with superoxide in biological systems, Beckman (1994a), and is an extremely potent oxidant that can initiate lipid peroxidation of human LDL. Darley-Usmar (1992). Third, nitric oxide affects redox-sensitive transcription of genes involved in endothelial cell activation such as VCAM-1. This implicates nitric oxide in atherosclerosis.

However, prior to this invention, it was not clear which NOS isoforms were involved in stimulating atherosclerosis. Malinski (1993). Moreover, it was also not clear how important is peroxynitrite formation to the molecular events of atherosclerosis. Peroxynitrite ($ONOO^-$) is a strong oxidant capable of lipid and protein oxidation. Beckman (1994a). Superoxide reacts with nitric oxide to form peroxynitrite faster, rate constant of $6.7 \times 10^{-9}$ M/sec, than superoxide is scavenged by superoxide dismutase, rate constant of $2.0 \times 10^{-9}$ M/sec. Endothelial cells are sensitive to the redox state and may respond with a program of endothelial cell activation, including expression of VCAM-1, ICAM-1, E-selectin, and MCP-1.

Many studies depend on pharmacological agents that block NOS enzymes, such as L-nitroarginine (L-NA) and L-N-arginine methyl ester (L-NAME). Inhibition of a process by these NOS inhibitors, and reversal of inhibition by excess L-arginine, but not D-arginine, provides evidence for the involvement of NO. However, these NOS inhibitors affect all three isoforms, so that the effect on different isoforms cannot be distinguished. Distinguishing between various NOS isoforms is particularly important since NOS isoforms have multiple roles and divergent effects.

Targeted gene disruption of the endothelial or neuronal NOS isoforms offers a new approach to dissect the relevance of NO in brain ischemia and the development of treatments for brain ischemia and stroke. For example, mice deficient in neuronal NOS gene expression were relatively resistant to brain injury after permanent focal cerebral ischemia. Huang et al. (1994).

Over the last several years, transgenic animals have been made containing specific genetic defects, e.g., resulting in the development of, or predisposition to, various disease states. These transgenic animals can be useful in characterizing the effect of such a defect on the organism as a whole, and developing pharmacological treatments for these defects.

The relevant techniques whereby foreign DNA sequences can be introduced into the mammalian germ line have been developed in mice. See *Manipulating the Mouse Embryo* (Hogan et al., eds., 2d ed., Cold Spring Harbor Press, 1994) (ISBN 0-87969-384-3). At present, one route of introducing foreign DNA into a germ line entails the direct microinjection of a few hundred linear DNA molecules into a pronucleus of a fertilized one-cell egg. Microinjected eggs may then subsequently be transferred into the oviducts of pseudopregnant foster mothers and allowed to develop. It has been reported by Brinster et al. (1985), that about 25% of the mice that develop inherit one or more copies of the micro-injected DNA.

In addition to transgenic mice, other transgenic animals have been made. For example, transgenic domestic livestock have also been made, such as pigs, sheep, and cattle.

Once integrated into the germ line, the foreign DNA may be expressed in the tissue of choice at high levels to produce a functional protein. The resulting animal exhibits the desired phenotypic property resulting from the production of the functional protein.

In light of the various biological functions of nitric oxide, there exists a need in the art to develop transgenic animals, e.g., transgenic mice, wherein the endothelial nitric oxide synthase gene has been modified. There also exists a need in the art to develop methods to test compounds for activity against various pathological states associated with the absence of eNOS, such as hypertension, atherosclerosis, and stroke, using these transgenic animals. A further need in the art is to develop treatments for various pathological states using nitric oxide or nitric oxide prodrugs.

SUMMARY OF THE INVENTION

This invention satisfies these needs in the art by providing a transgenic non-human animal comprising a disrupted endothelial nitric oxide synthase gene. In embodiments of this invention, the transgenic non-human animal exhibits hypertension or wound-healing abnormalities. In a specific embodiment of the invention, the transgenic non-human animal is a mouse. Moreover, in specific embodiments of this invention, the endothelial nitric oxide synthase gene is disrupted at exons encoding the NADPH ribose and adenine binding sites.

In other embodiments, this invention provides a method of testing compounds for activity against a vascular endothelial disorder by providing a transgenic non-human animal having a disrupted endothelial nitric oxide synthase gene, wherein the animal exhibits either a vascular endothelial disorder or is at increased risk of developing the vascular endothelial disorder, administering a compound to be tested to the transgenic animal, and determining the effect of the compound on the vascular endothelial disorder in the animal. In specific embodiments of this invention, the vascular endothelial disorder is hypertension or atherosclerosis.

This invention also provides a method for treating vascular endothelial disorders comprising: selectively increasing the expression of eNOS in blood vessels without increasing the expression of iNOS or nNOS. In specific embodiments, gene therapy approaches are used.

In a further embodiment, this invention provides a method of testing compounds for wound-healing activity by providing a transgenic non-human animal having a disrupted endothelial nitric oxide synthase gene, administering a compound to be tested to the transgenic animal, and determining the effect of the compound on the wound-healing capabilities of the animal.

In another embodiment, this invention provides a method of treating wounds by applying nitric oxide or a prodrug thereof. In a specific embodiment thereof, compounds which release nitric oxide into wounds to improve or speed up wound healing.

In an additional embodiment, this invention provides a method of making a transgenic non-human animal of the invention comprising providing an embryonic stem cell comprising an intact eNOS gene; providing a targeting vector capable of disrupting said eNOS gene upon homologous recombination; introducing said targeting vector into said cells under conditions where the intact eNOS gene of said cell and said targeting vector undergo homologous recombination to produce a disrupted eNOS gene; introducing said cells into a blastocyst; implanting the blastocyst into the uterus of a pseudopregnant female; and delivering transgenic animals of the invention from said pseudopregnant female. In order to obtain homozygous mutant mice of the invention, the resulting animals can be bred, and homozygous mutant mice selected.

In another embodiment, this invention provides a method of testing compounds for utility in the treatment of cerebral ischemia or stroke by providing a transgenic non-human animal having a disrupted endothelial nitric oxide synthase gene, administering a compound to be tested to the transgenic animal, determining the effect of the compound on infarct size or regional cerebral blood flow (rCBF) following induction of focal cerebral ischemia in the brain of said animal, and correlating the effect of said compound on infarct size or rCBF with a utility for the treatment of cerebral ischemia or stroke. In a preferred embodiment, the eNOS mutant animal has been rendered normotensive.

In a further embodiment, the invention also provides a method for testing compounds for utility in the treatment of atherosclerosis by providing a transgenic non-human animal having a disrupted endothelial nitric oxide synthase gene, administering a compound to be tested for atherosclerosis activity to the transgenic animal, determining the effect of the compound on atherosclerosis, and correlating the effect of said compound on atherosclerosis with a utility for the treatment of atherosclerosis. In specific embodiments, the effect of the compound on atherosclerosis is determined using the vessel or the cuff vessel injury model.

BRIEF DESCRIPTION OF THE FIGURES

FIG. 6A is a micrograph of a 24 hr. wound in a wild-type mouse. FIG. 6B is a micrograph of a 5 day wound in a wild-type mouse. FIG. 6C is a 24 hr. wound of an eNOS mutant mouse. FIG. 6D is a 5 day wound of an eNOS mutant mouse. (ep) refers to the epidermis, while (d) refers to the dermis. Capillaries are indicated by (cap).

In FIG. 7A infarct volumes were measured in SV-129 mice (A), C57 Black/6 mice (B), eNOS mutant mice without hydralazine treatment (C), and eNOS mutant mice following hydralazine treatment (D). Infarct size was detected 24 hrs after permanent filament MCA occlusion by TTC staining. A statistically significant increase (p<0.05) in infarct size was noted for eNOS mutant animals. Each dot represents the value from an individual animal, and data are expressed as mean ±SD.

FIG. 7B depicts infarct areas in five coronal sections from rostral to caudal (2 to 10 mm) of the above groups. Open circles, filled circles, and triangles represent wild-type SV-129 mice, wild-type C57 Black 6 mice, and eNOS mutant mice, respectively. Data shown are means ±SD. * indicates p<0.05 as compared to both wild-type SV-129 and wild-type C57 Black/6 mice. # indicates p<0.05 as compared to SV-129 mice alone.

FIG. 11A is the distribution in SV-129 wild-type mice. FIG. 11B is the distribution in C57 Black/6 wild-type mice. FIG. 11C is the distribution in eNOS mutant mice. FIG. 11D is the distribution in nNOS mutant mice. In FIGS. 11A–D, OB: olfactory bulb; Str: striatum; HP: hippocampus; DG: dentate gyrus; AM: amygdala; CB: cerebellum. Scale bar=300 μm.

FIGS. 12A–G show total binding. FIG. 12H shows binding remaining in the presence of 10 μM L-NA. In FIG. 12, OB: olfactory bulb; TT: tenia tecta; Str: striatum; RF: rhinal fissure; HP: hippocampus; DG: dentate gyrus; MAN: medial amygdaloid nuclei; CAN: anterior cortical amygdaloid nuclei; VMH: ventromedial hypothalamic nuclei; PC: posteromedial cortical amygdaloid nuclei; PT: piriform transition; LM: lateral mammillary nucleus; SG: superficial grey layer superior colliculus; CB: cerebellum; PR: pontine reticular nucleus. Scale bar=300 μm.

FIGS. 14A–14H depict [$^3$H]L-NA binding in sagittal sections of SV-129 mouse brain. FIG. 14A shows total binding. FIGS. 14B and 14C, respectively, show binding in the presence of 10 μM D-NA, and 100 μM 7-NI, a potent and selective type 1 inhibitor. FIG. 14D shows the binding in the presence of excess L-NA (10 μM). Scale bar–300 μm.

In FIG. 15A, nitric oxide produced by normal endothelium prevents proliferative response to injury and suppresses development of atherosclerosis. In FIG. 15B, nitric oxide production in atherosclerotic plaques may lead to peroxynitrite formation, lipid oxidation, and endothelial cell inactivation.

FIG. 20A shows the aortic arch and carotid arteries; FIG. 20B shows the thoracic aorta; FIG. 20C shows the descending thorascic aorta; and FIG. 20D shows oil red O stain of an aortic lesion.

DETAILED DESCRIPTION OF THE PREFERRED EMBODIMENTS

Figure 1:
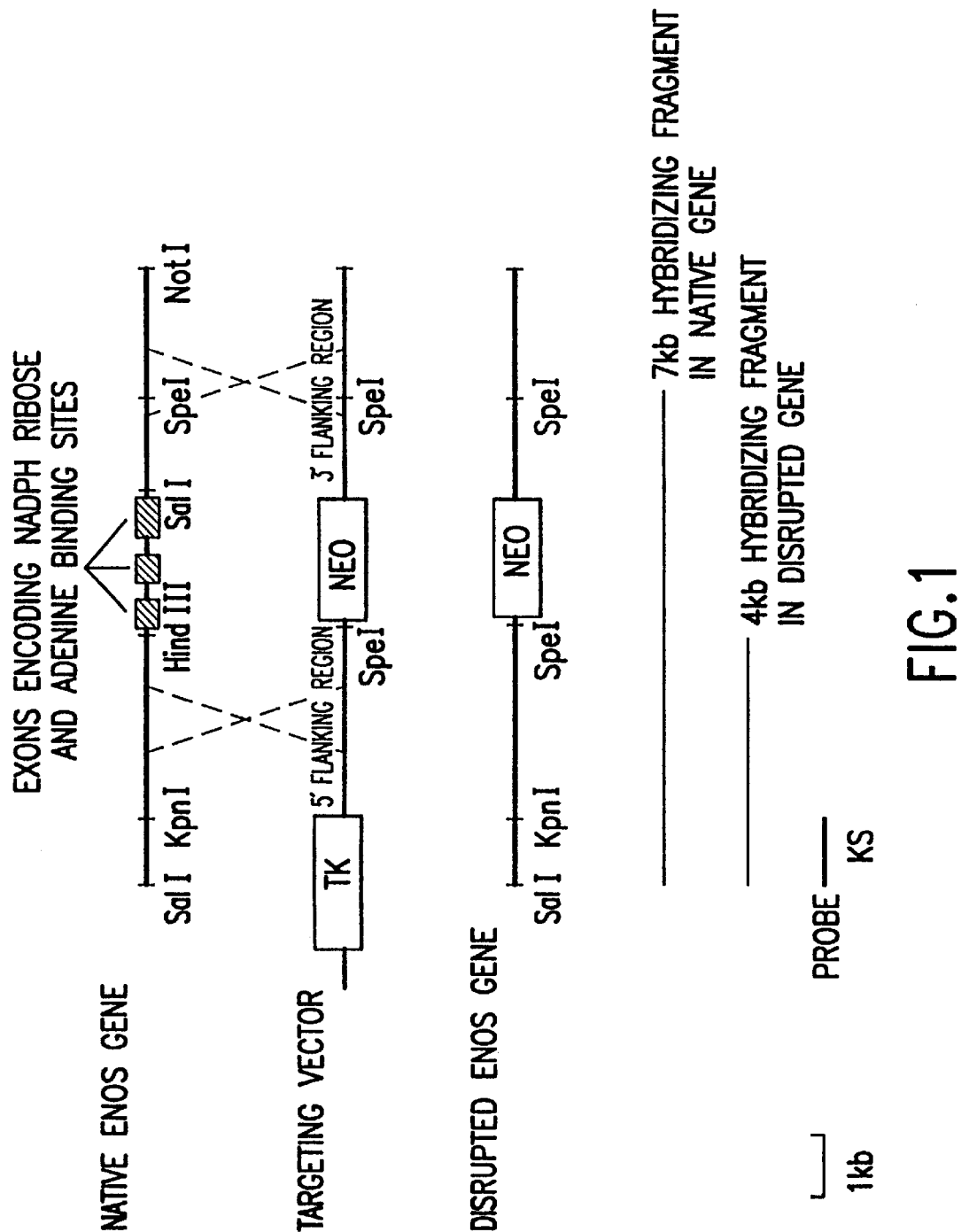
FIG. 1 depicts the targeted disruption of the endothelial NOS gene. This Figure shows restriction maps of the native mouse endothelial NOS gene, the targeting vector, and the disrupted eNOS gene. The targeted vector contains 5' and 3' flanking regions of homology and it is designed to replace the HindIII-SalI fragment of the eNOS gene containing exons encoding the NADPH ribose and adenine binding sites (amino acids 1010–1144). NEO refers to the neomycin antibiotic resistance gene. The location of the KS probe, used for Southern blot analysis, is also shown.

In the description that follows, a variety of various technical terms are used. Unless the context indicates otherwise, these terms shall have their ordinary well-recognized meaning in the art. In order to provide a clearer and more consistent understanding of the specification and claims, the following definitions are provided.

Transgenic. As used herein, a "transgenic organism" is an organism containing a defined change to its germ line, wherein the change is not ordinarily found in wild-type organisms. This change can be passed on to the organism's progeny. The change to the organism's germ line can be an insertion, a substitution, or a deletion. Thus, the term "transgenic" encompasses organisms where a gene has been eliminated or disrupted so as to result in the elimination of a phenotype associated with the disrupted gene ("knock-out animals"). The term "transgenic" also encompasses organisms containing modifications to their existing genes and organisms modified to contain exogenous genes introduced into their germ line.

Nitric oxide synthase (NOS). As used herein, nitric oxide synthase is an enzyme able to catalyze the formation of nitric oxide. For example, NOS can catalyze the formation of nitric oxide from the terminal guanidino nitrogen of arginine, with the stoichiometric production of citrulline.

Disrupted gene. As used herein, "disrupted gene" refers to a gene containing an insertion, substitution, or deletion resulting in the loss of substantially all of the biological activity associated with the gene. For example, a disrupted NOS gene would be unable to express a protein having substantial NOS enzymatic activity.

Vector. As used herein, a "vector" is a plasmid, phage, or other DNA sequence, which provides an appropriate nucleic acid environment for a transfer of a gene of interest into a host cell. The cloning vectors of this invention will ordinarily replicate autonomously in eukaryotic hosts. The cloning vector may be further characterized in terms of endonuclease restriction sites where the vector may be cut in a determinable fashion. The vector may also comprise a marker suitable for use in identifying cells transformed with the cloning vector. For example, markers can be antibiotic resistance genes.

Expression vector. As used herein, an "expression vector" is a vector comprising a structural gene operably linked to an expression control sequence so that the structural gene can be expressed when the expression vector is transformed into an appropriate host cell.

Targeting vector. As used herein "a targeting vector" is a vector comprising sequences that can be inserted into a gene to be disrupted, e.g., by homologous recombination. Therefore, a targeting vector may contain sequences homologous to the gene to be disrupted.

This invention relates to non-human transgenic animals comprising a disrupted endothelial NOS gene.

In order to obtain a transgenic animal comprising a disrupted eNOS gene, a targeting vector is used. The targeting vector will generally have a 5' flanking region and a 3' flanking region homologous to segments of the eNOS gene surrounding an unrelated DNA sequence to be inserted into the eNOS gene. For example, the unrelated DNA sequence can encode a selectable marker, such as an antibiotic resistance gene. Specific examples of a suitable selectable marker include the neomycin resistance gene (NEO) and the hygromycin β-phosphotransferase. The 5' flanking region and the 3' flanking region are homologous to regions within the eNOS gene surrounding the portion of the gene to be replaced with the unrelated DNA sequence. DNA comprising the targeting vector and the native eNOS gene are brought together under conditions where homologous recombination is favored. For example, the targeting vector and native eNOS gene sequence can be used to transform embryonic stem (ES) cells, where they can subsequently undergo homologous recombination. For example, J1 embryonic stem cells obtained from Dr. En Li of the Cardiovascular Research Center of the Massachusetts General Hospital and Dr. Rudolph Jaenisch of the Whitehead Institute of MIT. The targeting vector, pPNT-ENOS, has been deposited with the American Type Culture Collection (A.T.C.C.), 12301 Parklawn Drive, Rockville, Md. 20852 USA, under the terms of the Budapest Treaty under accession number A.T.C.C. 97469 on Mar. 13, 1996.

Proper homologous recombination can be tested by Southern blot analysis of restriction endonuclease digested DNA using a probe to a non-disrupted region of the eNOS gene. For example, the KS probe, identified in FIG. 1, can be used. Since the native eNOS gene will exhibit a different restriction pattern from the disrupted eNOS gene, the presence of a disrupted eNOS gene can be determined from the size of the restriction fragments that hybridize to the probe.

In one method of producing the transgenic animals, transformed ES cells containing a disrupted eNOS gene having undergone homologous recombination, are introduced into a normal blastocyst. The blastocyst is then transferred into the uterus of a pseudo-pregnant foster mother. Pseudo-pregnant foster mothers had been mated with vasectomized males, so that they are in the proper stage of their estrus cycle and their uterus is hormonally primed to accept an embryo. The foster mother delivers a transgenic animal containing a disrupted eNOS gene. Homozygous mutant animals are normally obtained by breeding the transgenic animals.

The extent of the contribution of the ES cells, containing the disrupted eNOS gene, to the somatic tissues of the transgenic mouse can be determined visually by choosing strains of mice for the source of the ES cells and blastocyst that have different coat colors.

The resulting homozygous eNOS mutant animals generated by homologous recombination are viable, fertile, and indistinguishable from wild-type and heterozygous littermates in overall appearance (except for the presence of a selectable marker) or routine behavior. However, the mutant animals can also be sterilized using methods well known in the art, e.g. vasectomy or tubal ligation. See *Manipulating the Mouse Embryo*, supra. The mutant animals can be mated to obtain homozygous or heterozygous progeny. These mutant animals contain substantially less immunoreactive eNOS than wild-type animals. Most preferably, these mutant mice contain no immunoreactive eNOS protein as measured by western blot analysis of brain, heart, lung, or aorta tissue.

A targeting vector such as pPNT-ENOS can be used to create cell lines or primary cell cultures that do not express NOS. The endogenous eNOS gene can be disrupted by introducing the targeting vector into cells containing the eNOS gene to be disrupted and allowing the targeting vector and the endogenous gene to undergo homologous recombination. For example, the targeting vector can be introduced into the cells by electroporation. If both copies of the eNOS gene are to be disrupted, higher concentrations of the selection agent, e.g., neomycin or its analog G418 are used. Suitable cell lines and cultures include tumor cells, endothelial cells, epithelial cells, leukocytes, neural cells, glial cells, and muscle cells.

The eNOS mutant animals of the invention can be any non-human mammal. In embodiments of this invention, the animal are mice, rats, guinea pigs, rabbits, or dogs. In an especially preferred embodiment of the invention, the eNOS mutant animal is a mouse.

These homozygous eNOS mutant animals also exhibit significantly reduced calcium-dependent membrane-associated NOS enzymatic activity. In preferred embodiments of this invention the enzymatic activity in aorta samples is less than 1.0 pmol mg$^{-1}$ min$^{-1}$ $^3$H-arginine to citrulline conversion. In most preferred embodiments of this invention the enzymatic activity in aorta samples is less than 0.5 pmol mg$^{-1}$ min$^{-1}$ $^3$H-arginine to citrulline conversion. Any residual NOS activity may be due to the presence of neuronal NOS (nNOS) in neurons in the perivascular plexus, and not to the expression of any residual nondisrupted eNOS genes.

Endothelium-derived relaxing factor is absent or significantly reduced in eNOS mutant animals. However, vascular smooth-muscle responses are intact. For example, the aortic rings of mutant mice show no relaxation to acetylcholine, while aortic rings from wild-type mice manifest a dose-dependent relaxation to acetylcholine. See FIG. 4. Moreover, treatment of wild-type aortic rings with 10$^{-4}$M L-nitroarginine has no effect on vascular tone by itself, but blocks the relaxation in response to acetylcholine. Id. Treatment of the eNOS mutant aortic rings with 10$^{-4}$M L-nitroarginine also has little or no effect on vessel tone either by itself or on the response to acetylcholine. The maximum dilation of norepinephrine pre-contracted rings from eNOS mutant mice to sodium nitroprusside is similar to wild-type mice. This indicates that vascular smooth-muscle responses in eNOS mutant animals are intact.

The eNOS mutant animals of the invention exhibit various vascular endothelial disorders. These disorders include hypertension and an increased propensity for cerebral ischemia, stroke or atherosclerosis. In addition, the eNOS mutant animals exhibit abnormal wound healing properties. Other vascular endothelial disorders include clotting disorders, other cerebrovascular disorders, coronary artery disease, and peripheral vascular disease. The eNOS mutant animals of the invention exhibit these disorders or an increased propensity of developing these disorders.

Consequently, the eNOS mutant animals are useful as a model to study these and other vascular endothelial disorders. For example, various compounds could be tested for a therapeutic effect on a vascular endothelial disorder by providing a transgenic non-human animal having a disrupted eNOS gene and exhibiting a vascular endothelial disorder; determining the effect of a compound on symptoms of the vascular endothelial disorder; and correlating the effect of the compound on the treatment of the vascular endothelial disorder.

The compounds to be tested are typically not NOS inhibitors. Determining whether a compound exhibits NOS inhibitor activity can be tested based on the information provided herein and in the technical literature. Hevel et al. (1994). In preferred embodiments of the invention, compounds that induce NO production are tested; and in more preferred embodiments, compounds that induce NO production in the endothelium are tested. The compounds to be tested can be derived from a variety of sources including, but not limited to, rationally designed and synthetic molecules, plant extracts, animal extracts, inorganic compounds, mixtures, solutions, and homogeneous molecular or elemental samples.

The eNOS mutant animals exhibit a significantly higher blood pressure than the wild-type animals. In specific embodiments of this invention eNOS mutant mice exhibit a mean blood pressure significantly higher than 81 mm Hg. In a preferred embodiment of this invention, eNOS mutant mice exhibit a mean blood pressure greater than about 100 mm Hg. In a most preferred embodiment of this invention, eNOS mutant mice exhibit a mean blood pressure of about 110 mm Hg. Analogous increases in mean blood pressure are expected in other non-murine eNOS mutant (knock-out) animals.

L-NA and other NOS inhibitors cause a rise in blood pressure in many species including humans, rats, guinea pigs, rabbits, dogs, and mice. This effect is consistent with a role of basal nitric oxide production in vasodilation, because inhibition of eNOS would lead to less basal vasodilation and result in hypertension. However, eNOS mutant mice show a decrease in blood pressure in response to L-NA. See FIG. 5. This hypotensive effect is blocked by L-arginine and is not observed with D-nitroarginine. This suggests that pharmacological blockers may have effects in addition to NOS inhibitors, or that non-endothelial NOS isoforms are involved in the maintenance of blood pressure. For example, nNOS is present both in vasomotor centers of the central nervous system and in perivascular nerves. However, effects of its blockade suggest that it plays a vasodilatory role. Mutant neuronal NOS mice have blood pressures similar to wild-type mice, but they have a tendency towards hypotension when exposed to anaesthesia, which is consistent with a possible role for nNOS in maintaining, not reducing, blood pressure. Multiple roles for endothelial and non-endothelial NOS isoforms in vasodilation and vasoconstriction may explain the observed variability in maximal pressor effects of various NOS inhibitors.

There is evidence that in hypertension the amount of NO produced by the endothelium decreases in humans. The eNOS knockout mice mimic this effect, since their endothelium also does not produce any NO. Consequently, these mice serve as a useful model for hypertension. Thus, establishing an anti-hypertensive effect in eNOS mutant animals of the invention for a compound other than an NOS inhibitor, such as a compound that induces the production of NO, would be predictive that this compound would have anti-hypertensive properties in other animals, including humans. However, the opposite result would be expected for a compound that inhibits NOS.

An inhibitor of NOS would be expected to raise blood pressure in wild-type animals, but stabilize or reduce blood pressure in eNOS mutant animals. In eNOS mutant animals, an NOS inhibitor would inhibit the residual NOS, mostly nNOS. nNOS mutant animals may have a tendency toward hypotension. Thus, the preferential inhibition of nNOS in the mutant animals should result in the same or lower blood pressure. However, in normal animals, the role of eNOS on blood pressure regulation is much more pronounced than the role of nNOS. Therefore, the predominant effect of an NOS inhibitor in normal animals would be to inhibit eNOS, which raises blood pressure. This is demonstrated in Example 5, infra.

In addition, there is also evidence that in atherosclerosis, diabetes and normal aging, the amount of NO produced by the endothelium decreases in humans. Thus, these mice would serve as a useful model not just for hypertension, but also for vascular responses in atherosclerosis, diabetes and normal aging.

The eNOS mutant animals of this invention are useful as an animal model to study hypertension. For example, various compounds could be tested for a anti-hypertensive effect in the eNOS mutant animals. Specifically, compounds that are not NOS inhibitors can be tested. In more preferred embodiments, compounds that are not eNOS inhibitors are tested. In other preferred embodiments compounds that induce NO production are tested. In additional preferred embodiments, compounds that induce NO production in the endothelium are tested. Therefore, the invention provides methods for screening compounds using the eNOS mutant animals as an animal model to identify compounds useful in treating hypertension. This aspect of the invention is useful to screen compounds from a variety of sources. Examples of compounds that can be screened using the method of the invention include but are not limited to rationally designed and synthetic molecules, plant extracts, animal extracts, inorganic compounds, mixtures, and solutions, as well as homogeneous molecular or elemental samples.

The invention, therefore, provides a method of screening compounds, comprising: providing a transgenic non-human animal having a disrupted eNOS gene and exhibiting hypertension, administering a compound to be tested to the transgenic animal; determining the effect of the compound on the blood pressure of said animal; and correlating the effect of the compound on the blood pressure of the animal with an anti-hypertensive effect of said compound.

The compounds to be tested can be administered to the transgenic non-human animal having a disrupted eNOS gene in a variety of ways well known to one of ordinary skill in the art. For example, the compound can be administered by parenteral injection, such as subcutaneous, intramuscular, or intra-abdominal injection, infusion, ingestion, suppository administration, and skin-patch application. Moreover, the compound can be provided in a pharmaceutically acceptable carrier. See Remington's Pharmaceutical Sciences (1990). The effect of the compound on blood pressure can be determined using methods well known to one of ordinary skill in the art.

In addition, the eNOS mutant animals of this invention unexpectedly exhibit abnormal wound-healing properties. For example, these animals often develop spontaneous wounds that do not heal. In contrast to normal mice, who healed their wounds within 5 days, the eNOS mutant mice exhibit significantly different wound healing properties. First, the eNOS mutant mice exhibit spontaneous wounds that never heal. Second, in experiments were wounds were created, the eNOS mutant mice heal more slowly than normal animals. Healing of eNOS mutant mice typically takes 2–3 times as long as normal mice. The exact healing time will depend on the type of wound inflicted. Moreover, two specific features of normal wound healing are abnormal in the eNOS mutant mice:

1) growth of the epithelial layer of skin across the wound to bridge the gap and close the wound; and
2) neovascularization in the granulation tissue that fills the wound.

In the eNOS mutant mice, migration of epithelial cells to the site of the wound is delayed, with epithelial cells remaining at the edge of the wound after five days. The connective tissue is also markedly abnormal, containing few or no new blood vessels. The results demonstrate an important role for eNOS in angiogenesis and epithelial cell migration during wound healing.

The eNOS mutant animals of this invention are useful as an animal model to study wound healing. For example, various compounds could be tested for a wound healing effect in the eNOS mutant animals. Therefore, the invention provides methods for screening compounds using the eNOS mutant animals as an animal model to identify compounds useful in enhancing wound healing. This aspect of the invention is useful to screen compounds from a variety of sources. Examples of compounds that can be screened using the method of the invention include but are not limited to rationally designed and synthetic molecules, plant extracts, animal extracts, inorganic compounds, mixtures, and solutions, as well as homogeneous molecular or elemental samples. For example, various compounds designed to improve wound healing can be tested. For example, compounds that deliver NO to the healing wound can be used. Establishing an enhancement of wound healing by a compound in eNOS mutant animals is predictive that this compound would enhance wound healing in other animals, including humans.

The invention, therefore, provides a method of screening compounds, comprising: providing a transgenic non-human animal having a disrupted eNOS gene and exhibiting abnormal wound healing properties, administering a compound to be tested to the transgenic animal; determining the effect of the compound on the wound healing properties of said animal; and correlating the effect of the compound on the wound healing properties of the animal with a wound healing effect of said compound.

Thus, the eNOS mutant animals of this invention are also useful as animal models to study wound healing.

Moreover, since the synthesis of nitric oxide appears to enhance wound healing, prodrugs that release nitric oxide in situ may improve or speed up healing. Examples of suitable compounds that release nitric oxide include nitroglycerin, sodium nitroprusside, and SIN-1. The extent to which these and other similar compounds improve or speed up wound healing can be determined experimentally. For example, the compound could be applied at the wound to a patient in need of treatment and its effect on wound healing can be quantified.

The eNOS mutant animals of this invention are also useful as an animal model to study cerebral ischemia resulting from stroke. Since endothelial NO production may protect brain tissue by increasing ischemic rCBF, compounds can be tested for the ability to increase rCBF as well as the ability to reduce ischemic infarct size. rCBF and infarct size can be measured as described in the Examples. Compounds that increase rCBF or decrease infarct size would be expected to be useful as therapeutics for the treatment of stroke or cerebral ischemia from other sources.

It has been reported that nNOS enzymatic activity may contribute to the development of ischemic brain necrosis. In eNOS mutant animals, any non-specific NOS inhibitor would predominantly inhibit the nNOS isoform. However, in wild-type animals, both eNOS and nNOS would be inhibited. Since eNOS and nNOS have opposite effects under ischemic conditions, with eNOS activity being protective and nNOS activity being detrimental, compounds that are non-specific NOS inhibitors should not be tested for anti-stroke activity. Therefore, in preferred embodiments compounds that are not NOS inhibitors are tested. In more preferred embodiments, compounds that induce NO production can be tested for use as a treatment for stroke or cerebral ischemia. In particularly preferred embodiments, compounds that induce production of NO in the endothelium are tested.

Compounds that can be screened for use in treating stroke or cerebral ischemia can be obtained from a variety of sources. Examples of compounds that can be screened using the method of the invention include but are not limited to rationally designed and synthetic molecules, plant extracts, animal extracts, inorganic compounds, mixtures, and solutions, as well as homogeneous molecular or elemental samples.

The compounds to be tested can be administered to the transgenic non-human animal having a disrupted eNOS gene in a variety of ways well known to one of ordinary skill in the art. For example, the compound can be administered by parenteral injection, such as subcutaneous, intramuscular, or intra-abdominal injection, infusion, ingestion, suppository administration, and skin-patch application. Moreover, the compound can be provided in a pharmaceutically acceptable carrier. See Remington's Pharmaceutical Sciences (1990).

The eNOS animals are additionally useful as an animal model to study atherosclerosis. The physiological production of nitric oxide by eNOS suppresses atherosclerosis, whereas the pathologic production of nitric oxide by iNOS and nNOS contributes to atherosclerosis. To test the effect of various compounds on atherosclerosis, various animal models involving eNOS mutant mice are used. Two vessel injury models, the cuff model and the filament model, provide useful data relevant to atherosclerosis. In the cuff model the neointima formation is stimulated by adventitial injury. In the filament model, the endothelium is physically removed, and the rate at which endothelial cells resurface the injured areas is measured. Alternatively, double mutant animals exhibiting aspects of atherosclerosis can be used. For example, double mutant apoE, eNOS mice can be used. Other potential double mutant animals for use in this aspect of the invention include apoE Leiden/eNOS and LDL-receptor eNOS mutants.

By way of example, compounds can be provided to eNOS mutant mice, and the effect of the compound on neointima formation following vessel injury using the cuff model can be determined. The extent of neointima formation can be determined as described in the Examples. Compounds that reduce the extent of neointima formation relative to control eNOS mutant mice not receiving the compound would be expected to be useful as therapeutics for the treatment of atherosclerosis.

In another example, compounds can be provided to eNOS mutant mice and the effect of the compound on the rate at which endothelial cells resurface injured areas of vessels following vessel injury using the filament model can be determined. Compounds that increase the rate of endothelial cell resurfacing relative to control eNOS mutant mice not receiving the compound would be expected to be useful as therapeutics for the treatment of atherosclerosis.

In a further example, compounds can be provided to double mutant animals, which exhibit features of human atherosclerosis. Compounds that reduce symptoms of atherosclerosis in these animals would also be expected to be useful as therapeutics for the treatment of atherosclerosis. A preferred example of a double mutant animal is an apoE/eNOS double mutant.

Since nNOS and iNOS may contribute to atherosclerosis, compounds that are non-specific NOS inhibitors should not be tested for activity against atherosclerosis. Compounds to be tested can be obtained from various sources and administered in various ways as described for other endothelial vascular disorders, supra.

Another example of a double mutant animal is eNOS/nNOS mutant mice. These double mutant animals can be obtained by mating eNOS mutant mice to nNOS mutant mice of the same genetic background. Double heterozygous eNOS/nNOS mutant mice are obtained, mating pairs of the double heterozygous mice are obtained, and eNOS/nNOS mutant mice are obtained.

EXAMPLES

Example 1

Targeted Disruption of the Endothelial NOS Gene

The endothelial NOS gene was cloned by screening a mouse genomic library, obtained from Stratagene, using a human eNOS cDNA clone, obtained from Kenneth D. Bloch, as described in Jannsens et al. (1992), Genbank accession number M93718. Plasmid hNOS3C, containing the endothelial nitric oxide synthase gene, was deposited at the American Type Culture Collection on Jul. 17, 1996. The targeting vector was derived from the pPNT vector, which contains thymidine kinase gene and the neomycin resistance gene. See FIG. 1. Tybulewicz et al. (1991). The targeting vector contains 5' and 3' flanking regions of homology to the eNOS gene, and is designed to replace the HindIII-SalI fragment that contains exons encoding the NADPH ribose and adenine binding sites of the eNOS protein (amino acids 1010–1144) following homologous recombination.

J1 ES cells were grown as described in Li et al. (1992) on irradiated embryonic fibroblast feeder cells in media containing 200 units/ml leukocyte inhibitory factor. For electroporation, $10^7$ cells were mixed with targeting vector DNA at 150 μg/ml. A Bio-Rad gene pulsar was used to electroporate the DNA into the cells at a setting of 960 μF capacitance, 250 mV. The targeting vector and the native eNOS gene were then able to undergo homologous recombination. The cells were plated on neomycin-resistant irradiated fibroblast feeder cells, and selection with 150 μg/ml G418 and 2 μM FIAU was started 48 hours later. Doubly resistant colonies were picked seven days after electroporation and grown in 24-well plates.

Example 2

Generation of Chimeric Mice With Germline Transmission

Blastocysts were isolated from C57 BL/6 mice on day 3.5 of pregnancy and 20–25 ES cells, following homologous recombination and selection, were injected into the uterine horn of pseudo-pregnant (C57 BL/6×DBA/2) F1 mice. Chimeric mice were identified by the agouti contribution of the ES cells to the coat color, and were back-crossed to C57 BL/6 mice. Germline transmission was determined by the presence of agouti mice in the offspring.

Figure 2:
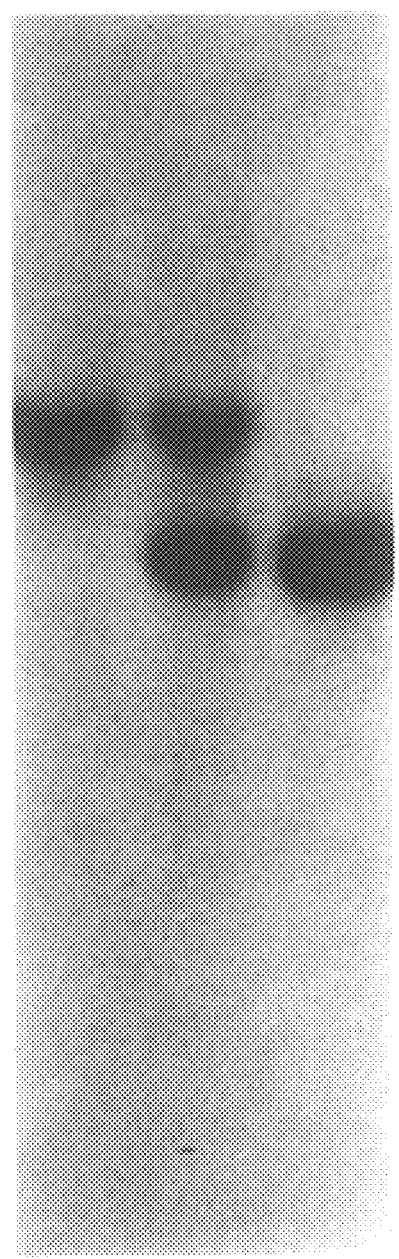
FIG. 2 shows the results of a Southern blot analysis of genomic DNA isolated from mutant mouse tails, digested with SpeI and hybridized to the KS probe, shown in FIG. 1. Lanes 1, 2, and 3 show wild-type, heterozygous, and homozygous eNOS mutant mice, respectively. The positions of fragments hybridizing to the wild-type and the disrupted eNOS gene, as depicted in FIG. 1, are indicated.

Proper recombination was demonstrated by Southern blot analysis of SpeI digested genomic DNA using the KS probe shown in FIG. 2. Back-crossed mice were screened by Southern blot, and heterologous mice were selected. In FIG. 2, lanes 1, 2 and 3 show wild-type, heterozygous, and homozygous mutant mice, respectively. The positions of the hybridizing fragments of the wild-type and the disrupted eNOS gene are shown. The results demonstrate that the targeted disruption of the eNOS gene is present in the germline of the transgenic mice.

Figure 3:
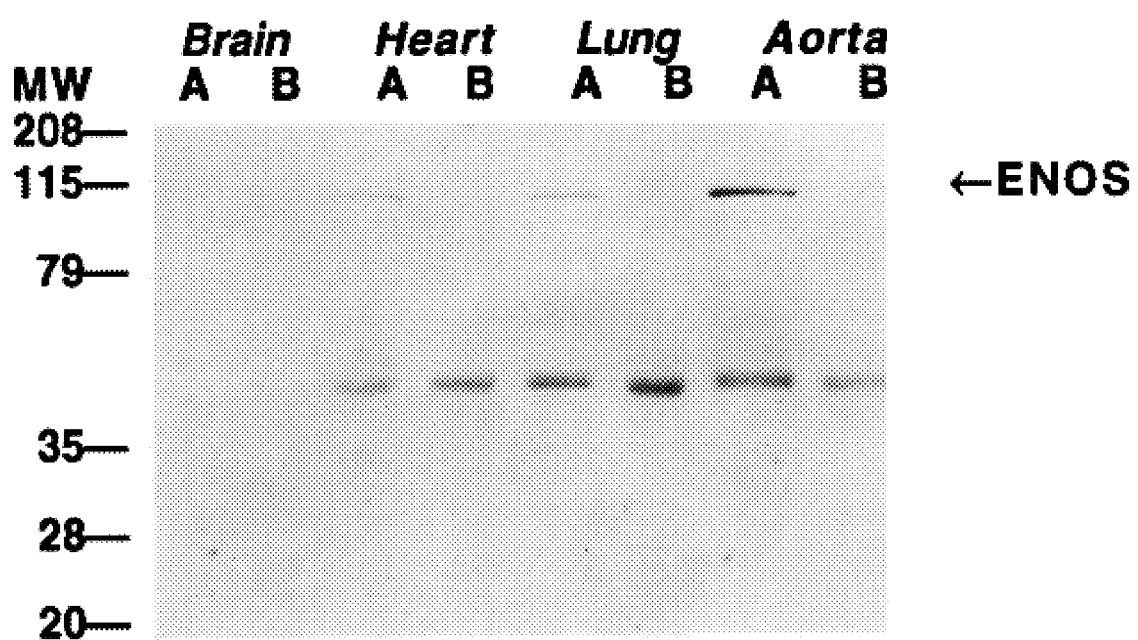
FIG. 3 depicts a Western blot analysis of eNOS mutant mice. Brain, heart, lung and aorta samples of wild-type (wt) and mutant (m) mice were tested for immunological reactivity against a mouse monoclonal antibody directed against eNOS. The position of eNOS is shown.

Western blot analysis of tissue samples from eNOS mutant mice was also performed. 10 μg protein extracts from the brain, heart, lung, and aorta/vena cava of wild-type and eNOS mutant animals were electrophoresed through a 10% SDS-polyacrylamide gel and transferred to nitrocellulose. The blot was incubated with mouse monoclonal antibodies directed against endothelial NOS (Transduction Research Laboratories), and specific hybridization was localized using chemiluminescent alkaline phosphatase conjugated with anti-mouse antibody (ECL, Amersham). Hybridization of endothelial NOS is observed for the wild-type samples, but not in the eNOS mutant samples. The heart, lung, and aorta samples show a band at relative molecular mass of 50 kDa in both wild-type and eNOS mutant samples, which represents mouse immunoglobulin heavy chains present in the tissue samples. The antibody used was directed against a peptide corresponding to amino acids 1030–1209, a region which overlaps with the region deleted in the eNOS mutant mice. See FIG. 3. This demonstrates that the eNOS mutant mice (homozygous) produce no immunoreactive undisrupted eNOS, further demonstrating successful transmission of the disruption to the germline of the transgenic mice.

Aorta samples from eNOS mutant mice were tested for calcium-dependent membrane-associated NOS enzymatic activity. This enzymatic activity was reduced to about 0.5 pmol $mg^{-1}$ $min^{-1}$. The residual activity is likely due to neuronal NOS in neurons in the perivascular plexus.

Example 3

Determination of Blood Pressure of eNOS Mutant and Wild-type Mice

Mice were kept at normal temperature (37° C.), anesthetized with urethane (1.5 mg/kg, intraperitoneal injection) or halothane inhalation, and ventilated using an SAR-830 mouse ventilator (CWE Instruments). Depth of anesthesia was adjusted to keep the blood pressure of animals unresponsive to tail-pinch with forceps. End-tidal $CO_2$ was monitored with a microcapnometer and kept constant by adjustment of respiratory parameters. The right femoral artery was cannulated using stretched PE-10 polyethylene tubing (Clay Adams) for mean arterial blood pressure recordings using an ETH-400 transducer and a MacLab data acquisition system (ADI Instruments). For awake measurements, the femoral artery catheter was placed under halothane anesthesia and the wound was covered with 1% xylocane ointment to diminish discomfort. Recordings were made within one hour of the procedure. Data are expressed as means with standard deviation. Statistical evaluation was performed by t-test.

TABLE 1

Blood pressure of eNOS mutant and wild-type mice

| | Wild-type mice | | | eNOS mutant mice | | |
|---|---|---|---|---|---|---|
| | Urethane | Halo-thane | Awake | Urethane | Halo-thane | Awake |
| Mean BP (mmHG) | 81 | 90 | 97 | 110* | 109* | 117* |
| s.d. | 9 | 12 | 8 | 8 | 11 | 10 |
| n | 16 | 15 | 14 | 17 | 18 | 17 |

*$P < 0.01$ for eNOS mutant animals vs. wild-type mice.

There is no statistically significant difference between the blood pressure of nNOS mutant mice and wild-type mice using this procedure.

Similar results are obtained with different methods of anesthesia and in the awake state. Blood pressure is the same for the wild-type SV129 strain, wild-type C57 B16 strain, and litter mates of the eNOS mutant animals that are wild-type at the eNOS locus.

Example 4

Endothelium-dependent Relaxation of Aortic Rings in Response to Acetylcholine From eNOS Mutant and Wild-type Mice The thoracic aorta was dissected from wild-type and eNOS mutant mice and placed in physiological saline aerated with 95% $O_2$/5% $CO_2$. 4 mm segments of the aorta were mounted on tungsten wires in conventional myographs and maintained at optimal tension in physiological saline for 1 hour at 37° C. The rings were pre-contracted with $10^{-7}$ M norepinephrine and exposed to increasing concentrations of acetylcholine (ACh) from $10^{-8}$ M to $3 \times 10^{-5}$ M. 2–3 segments were collected from each mouse, and five mice were used from the wild-type and eNOS mutant groups. Mean data from each animal were used. Respective tracings are shown. Acetylcholine concentrations are expressed in logM.

Figure 4A:
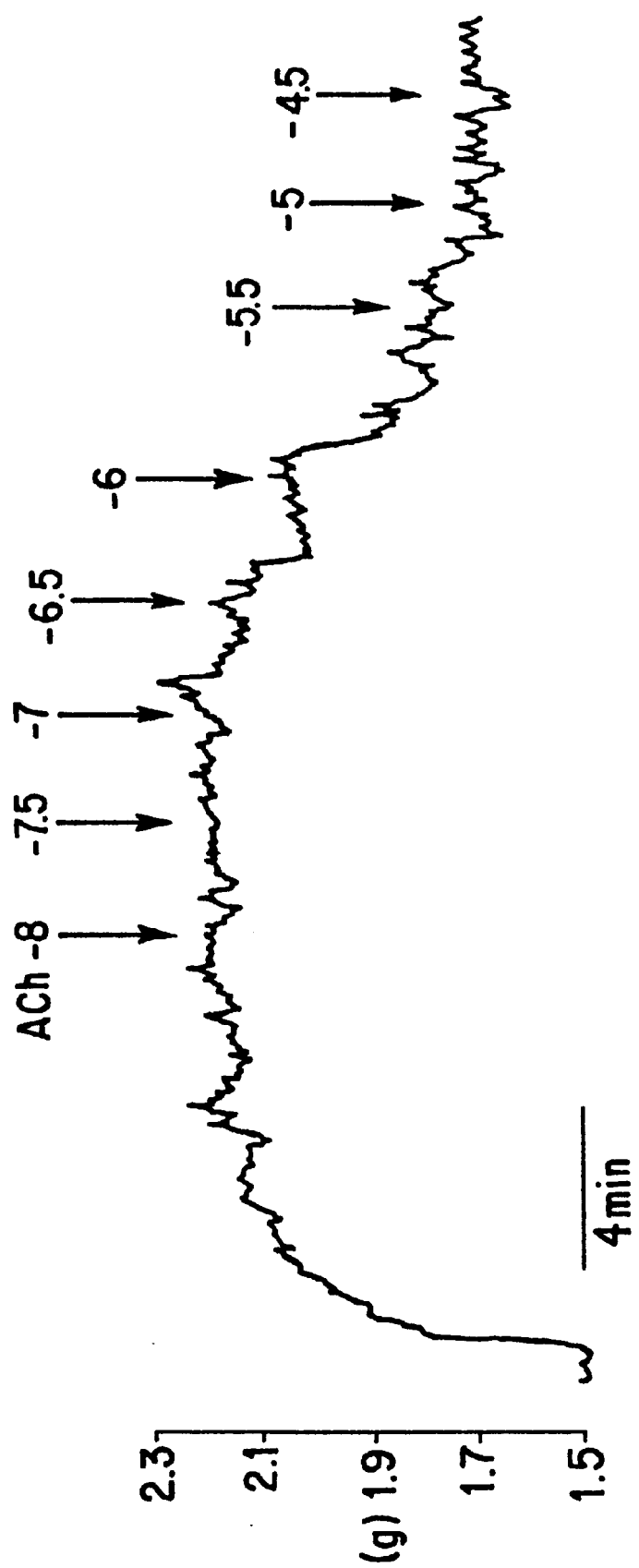
FIGS. 4A–4C depict the endothelium-dependent relaxation of aortic rings in response to acetylcholine. Panel a shows the effect on wild-type aortic segments. Panel b depicts treatment of wild-type vessel rings with L-nitroarginine (L-NA), a NOS inhibitor. Panel c depicts the endothelium-dependent relaxation of eNOS mutant aortic segments.
Figure 4B:
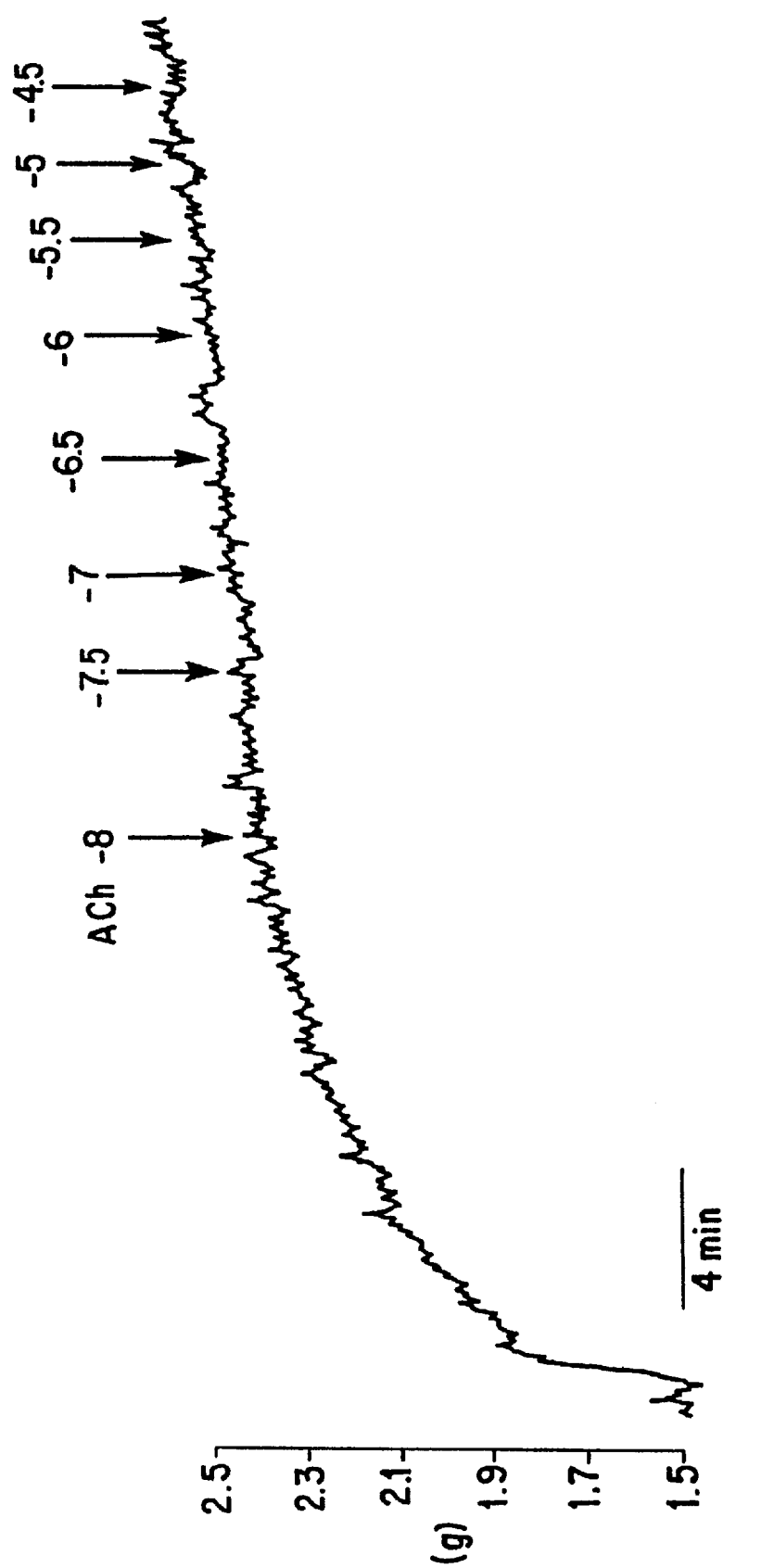
Figure 4C:
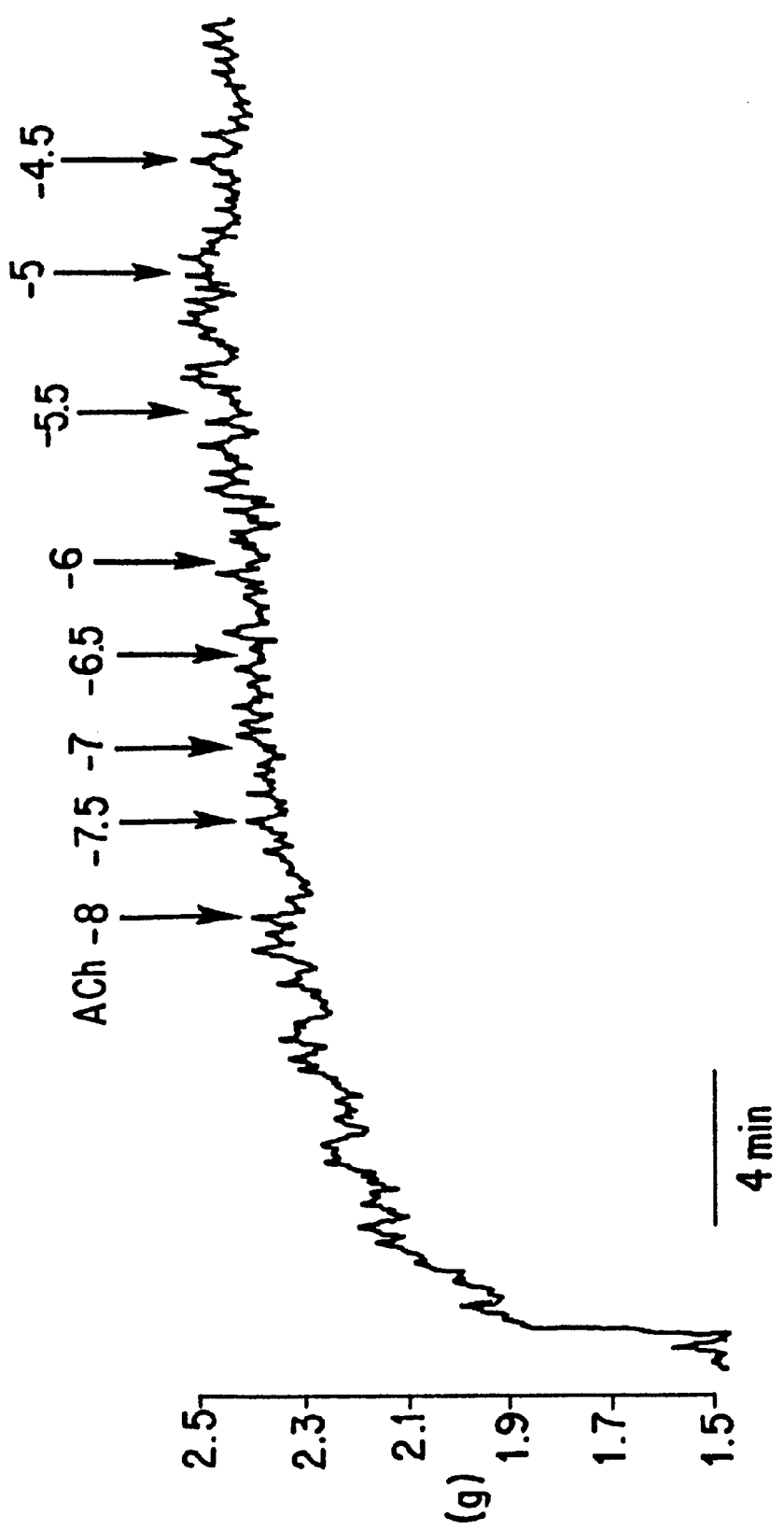

FIG. 4A depicts wild-type aortic segments responding to acetylcholine with dose-dependent relaxation. At $3 \times 10^{-5}$ M, 60.3±14.6% of pre-addition tone was present. FIG. 4B depicts treatment of the wild-type vessel rings with $10^{-4}$ M L-NA for 1 hour and shows abolished acetylcholine-induced relaxation. FIG. 4C shows that eNOS mutant aortic segments do not relax to acetylcholine, demonstrating that EDRF activity is absent from eNOS mutant mice. L-NA has no additional affect on eNOS vessel segments.

Thus, aortic rings from wild-type mice manifest a dose-dependent relaxation to acetylcholine, while aortic rings from eNOS mutant animals show no relaxation to acetylcholine. Treatment of wild-type aortic rings with $10^{-4}$ M L-NA has no effect on vascular tone by itself, but blocks the relaxation in response to acetylcholine. Treatment of the eNOS mutant aortic rings with $10^{-4}$ M L-NA has no effect on vessel tone, either by itself or in response to acetylcholine. The maximum dilation of norepinephrine pre-contracted rings from eNOS mutant mice to sodium nitroprusside is no different from wild-type mice, indicating that vascular smooth-muscle responses are intact.

Example 5

Blood Pressure Responses to L-NA for Wild-type and eNOS Mutant Mice

Figure 5:
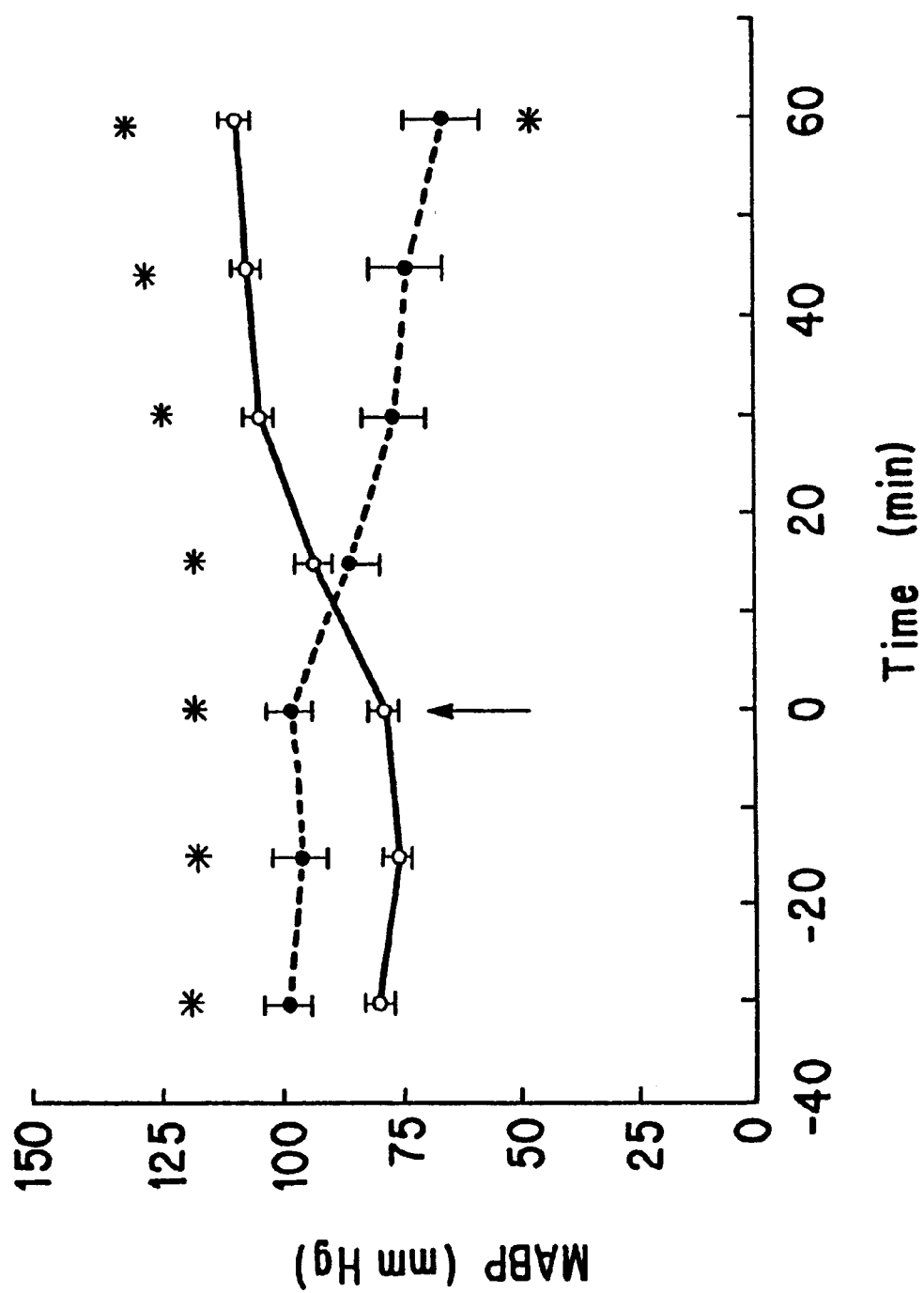
FIG. 5 depicts blood pressure responses to L-NA. Urethane-anesthetized wild-type (solid line) and eNOS mutant mice (dotted line) were measured before and after L-NA administration at time 0.
Figure 6A:
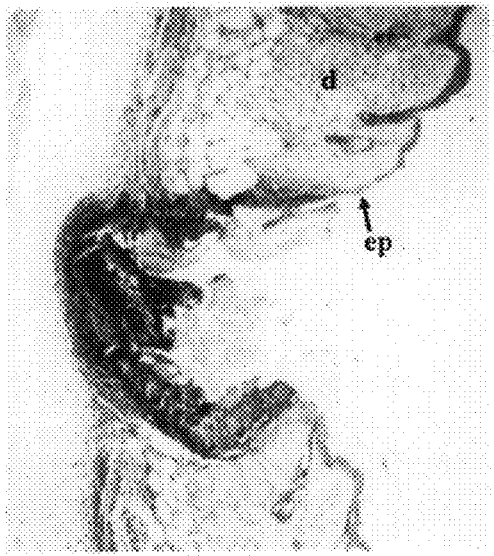
FIGS. 6A–6D depict wound healing in eNOS mutant mice.
Figure 6B:
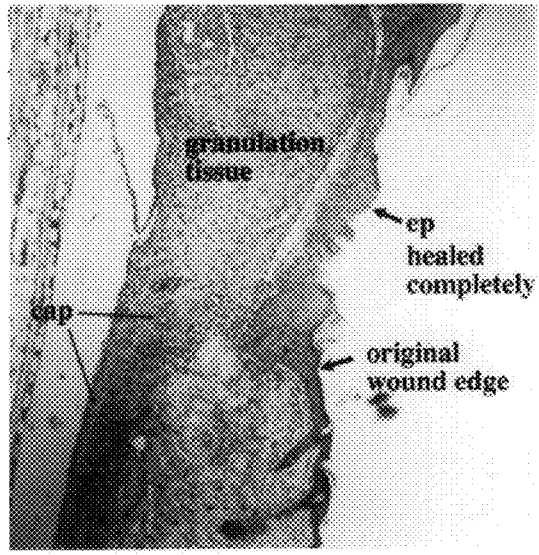
Figure 6C:
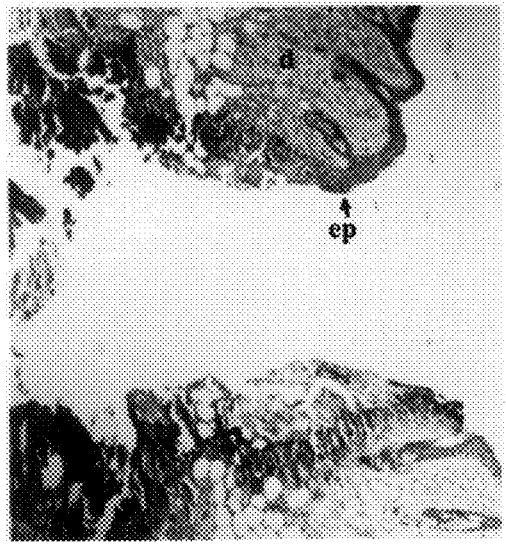
Figure 6D:
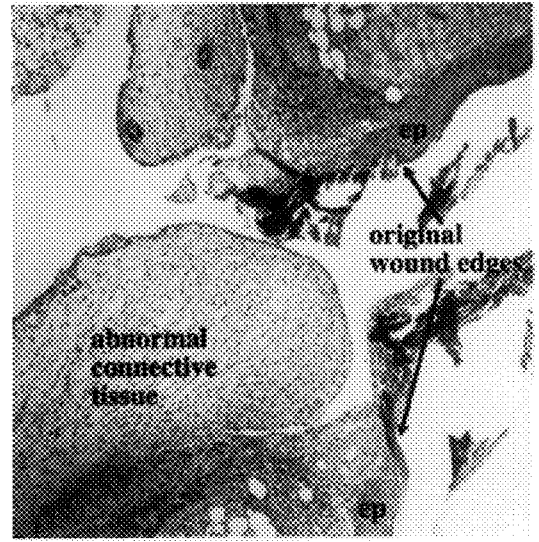

Mean arterial blood pressure (MABP) of urethane-anesthetized wild-type (solid line in FIG. 5) and eNOS mutant mice (dotted line in FIG. 5) were measured by femoral artery catheterization and recorded for 30 minutes of baseline before L-NA administration (arrows in FIG. 5). At time 0, 12 mg/kg of L-NA was given intraperitoneally. Monitoring for 1 hour shows that the blood pressure of wild-type mice rose from a baseline of 78 mm Hg to 109 mm Hg (n=11). The blood pressure of eNOS mutant mice dropped from a baseline of 98 mm Hg to 66 mm Hg (n=5). Each mouse in the wild-type group responded to L-NA with a rise in blood pressure, and each mouse in the eNOS mutant group responded with a drop in pressure. Mean arterial blood pressure differences between wild-type and eNOS mutant animals are statistically significant by the t-test (#, $p<0.01$). Differences between baseline blood pressures and following L-NA treatment were also statistically significant (*, $P<0.05$ by ANOVA followed by Dunnett). These effects were prevented by L-arginine (200 mg/kg, intraperitoneal), and were not seen with D-nitroarginine (12 mg/kg). The heart rate of eNOS mutant mice and wild-type mice did not differ, and L-NA had no effect on heart rate.

These results support the conclusion that eNOS in the endothelium regulates blood pressure. The major NOS isoform in the endothelium is eNOS. However, a small amount of nNOS is also present. Disruption of the eNOS gene raises blood pressure, while disruption of the nNOS gene stabilizes or lowers blood pressure. Thus, inhibition of NOS in wild-type animals by L-NA, which would predominantly inhibit eNOS, would be expected to raise blood pressure. This is shown in FIG. 5. However, inhibition of NOS in eNOS mutant mice would not be expected to raise blood pressure since the effect of L-NA inhibition in the mutants would be to inhibit nNOS and not eNOS. Since nNOS maintains or raises blood pressure levels, see supra, inhibition of nNOS would be expected to lower blood pressure levels. This is also seen in FIG. 5.

Example 6

Screening of Compounds for Anti-hypertensive Effects Using eNOS Mutant Mice The eNOS mutant mice exhibit hypertension. Compounds that are associated with NO production in the endothelium, thereby replacing eNOS enzymatic activity, are screened for anti-hypertension activity in eNOS mutant mice. These compounds can be administered to the eNOS mutant mice using pharmaceutically acceptable methods. See Remington's Pharmaceutical Sciences (1990). For example, the compound to be screened can be administered at various concentrations by parenteral injection, infusion, ingestion, and other suitable methods in admixture with a pharmaceutically acceptable carrier. The effect of various concentrations of the screened compound on blood pressure is measured relative to control eNOS mutant animals that have not been administered the compound.

A significant decrease in blood pressure of the eNOS mutant mice by a screened compound is indicative that this compound would exhibit beneficial anti-hypertensive properties in other animals and in humans.

Example 7

Wound Healing in eNOS Mutant Mice

It was observed that eNOS mutant mice, but not wild-type or nNOS mutant mice, tend to develop chronic wounds. Therefore, eNOS mutant mice were tested in a model of wound healing involving a full thickness transverse incision overlying the lumbar area. The incisions penetrated the deep dermis down to the skeletal muscle. In FIG. 6, the histological appearance of these wounds at 24 hours and at 5 days following incision, for wild-type and eNOS mutant mice, are shown. At 24 hours, the wounds are very similar. The epidermis (ep) and the deep dermis (d) are transfected. Inflammatory cells are seen in both wild-type and eNOS mutant mice.

By five days, wild-type mice have healed. The epithelial layer is reconstituted, and granulation tissue with newly sprouted capillaries fills in the scar. The dermis, which has been cut, remains absent in the healed wound. Thus, normal healing involves two quantifiable features: rapid epithelial migration from the wound edges, and the development of new capillaries, neovasculation, in the connective tissue matrix.

In these eNOS mutant animals, little or no healing has been observed at 5 days. The migration of epithelial cells is delayed, and the epithelial cells remain at the edge of the wound (ep). The connective tissue is markedly abnormal, and contains few or no new vessels. These results demonstrate an important role for eNOS in angiogenesis and epithelial cell migration during wound healing.

Example 8

Screening of Compounds for Wound Healing Effects Using eNOS Mutant Mice

The eNOS mutant mice exhibit spontaneous wounds. Compounds to be screened for wound healing activity can be administered to the eNOS mutant mice in a pharmaceutically acceptable excipient. For example, the compound can be administered at various concentrations to the wound directly as an ointment or salve. Alternatively, other pharmaceutically acceptable modes of administration can be used. For example, a pharmaceutical composition comprising the compound can be administered by parenteral injection, infusion, ingestion, skin-patch application, and other suitable methods. The effect of the compound is measured relative to control eNOS animals that have not been administered the compound.

A significant enhancement of wound healing on the spontaneous wounds of eNOS mutant mice by a screened compound would indicate that this compound exhibits beneficial wound healing properties in other animals and in humans.

Particularly preferred compounds for screening are compounds known to release NO, such as nitroglycerin, sodium nitroprusside, and SIN-1.

Similarly, eNOS mutant mice having artificially inflicted wounds can also be used in such a screening assay. For example, the effect of various compounds on a full thickness transverse incision, as described in the preceding example, can be used as a screening assay.

Example 9

Determination of Cerebral Infarct Sizes After Middle Cerebral Artery (MCA) Occlusion in Wild-type and eNOS Mutant Mice Male and female wild-type (SV-129 and C57 Black/6, Taconic Farms, Germantown, N.Y.) and eNOS mutant mice weighing 20 to 26 g were housed under diurnal lighting conditions and allowed free access to food and water ad libitum. Nitro-L-arginine, nitro-D-arginine, hydralazine hydrochloride and 2,3,5-triphenyltetrazolium chloride (TTC) were purchased from Sigma.

Mice were anesthetized with 2% halothane for induction and maintained on 1% halothane in 70/30% nitrous oxide/oxygen by mask. The right femoral artery was cannulated with PE-10 polyethylene tubing for arterial blood pressure measurement (Gould, Oxnard, Calif.) and blood gas determination (Corning 178, Ciba Corning Diag., Medford, Mass.). Rectal temperature was maintained between 36.5–37.5° C. with a homeothermic blanket system (YSI, Yellow Springs, Ohio).

Focal cerebral ischemia was induced by occlusion of middle cerebral artery (MCA) using the intraluminal filament technique. Zea-Longa et al. (1989); Huang et al. (1994). Through a ventral midline incision, the right common and external arteries were isolated and ligated. A microvascular clip (Zen temporary clip, Ohwa Tsusho, Tokyo, Japan) was temporarily placed on the internal artery and the pterygopalatine artery. An 8-0 nylon monofilament (Ethicon, Somerville, N.J.) coated with silicone was introduced through a small incision in the common corotid artery and advanced 10 mm distal to the carotid bifurcation so as to occlude the MCA and posterior communicating artery. The wound was sutured and the animal returned to its cage and allowed free access to water and food.

Twenty-four hours later, animals were sacrificed with an overdoses of pentobarbital and the brains removed and sectioned coronally into five 2-mm slices in a mouse brain matrix. Slices were placed in 2% TTC solution, followed by 10% formalin overnight. Morikawa et al. (1994a). The infarction area, outlined in white, was measured (Bioquant IV image analysis system) on the posterior surface of each section, and the infarction volume was calculated by summing the infarct volumes of sequential 2 mm thick sections.

In protocol 1, MCA occlusion was produced in SV-129 (n=12), C57 Black/6 (n=11), eNOS mutant mice (n=14), and eNOS mutant mice injected with hydralazine (1 mg/kg, ip, 1 hr before and 5, 17 hrs after MCA occlusion) to match the arterial blood pressure of wild-type mice (n=10).

In protocol 2, eNOS mutant and wild-type animals were injected with nitro-L-arginine (6 mg/kg, ip, 5 min, 3 and 6 hrs after ischemia) or an equivalent volume of saline vehicle in order to test the hypothesis that inhibition of nNOS activity alleviated ischemic brain injury. The investigator was blinded to the treatment group in this protocol.

As discussed supra, the mean arterial blood pressures in eNOS mutant mice were higher (115±8 mmHg) than wild-type animals (98±7 mmHg and 94±7 mmHg in SV-129 and C57 B/6, respectively). After hydralazine administration however, mean arterial blood pressures (MABP) did not differ between groups (Table 2).

In this and in Examples 10–11, data are expressed as means ±SD. Statistical evaluation was performed by analysis of variance (ANOVA) followed by t-test to compare the data among groups in protocol 1. Unpaired Student's t-test was used to test the significance between two groups in protocol 2 and rCBF measurement. ANOVA with repeated measures and ANOVA followed by t-test were used to evaluate significance within group differences and individual points between groups in the autoregulation experiment. Probability values less than 0.05 were considered of statistical significance.

Figure 7A:
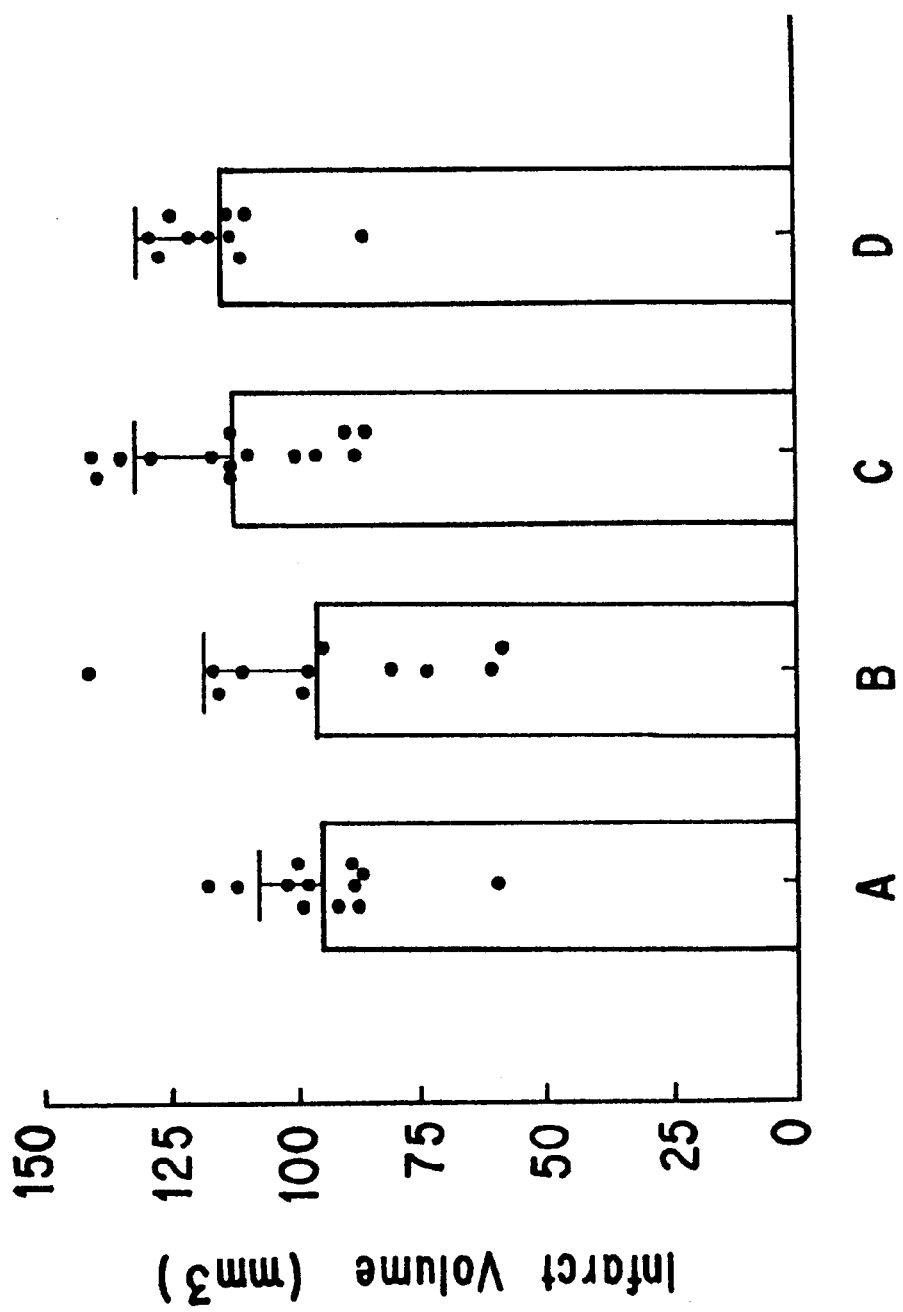
FIGS. 7A–7B depict infarct size in wild-type and eNOS mutant mice.
Figure 7B:
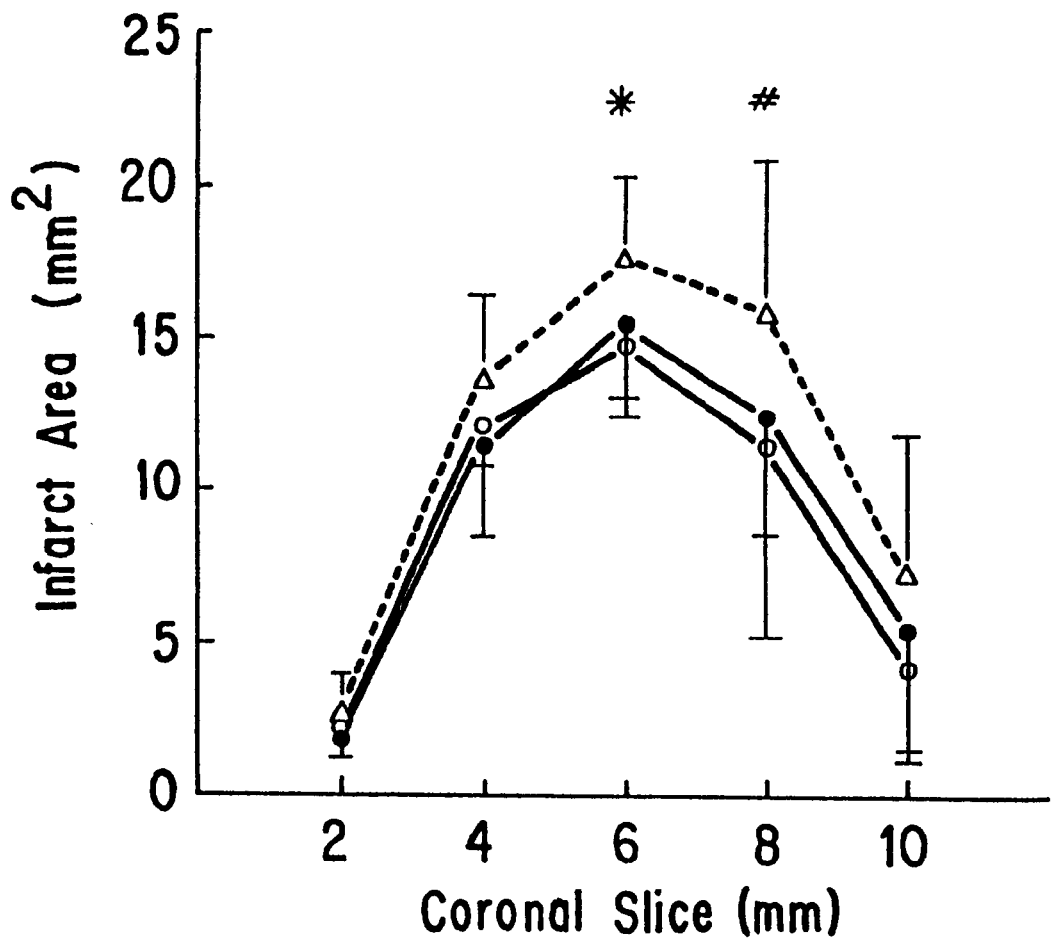

In protocol 1, wild-type SV-129 and C57 Black/6 developed infarcts that were 37±7% (n=12) and 38±15% (n=11) of their respective hemispheres. Larger infarct volumes (46±9% of hemisphere, n=14, $p<0.05$ as compared to wild-type SV-129 and C57 Black/6) were measured in eNOS mutant mice. Larger infarct volumes were also recorded in eNOS mutant mice made normotensive by hydralazine treatment (48±7% of hemisphere, n=10, $p<0.05$ vs wild-type SV-129 or C57 Black/6) (FIGS. 7A,B). There were no significant group differences in physiology or blood gases before and 24 hrs after MCA occlusion to explain these differences (Table 2).

In protocol 2, administration of nitro-L-arginine decreased infarct volume in the eNOS mutant mice by 24% and injury volumes became equivalent to wild type. Nitro-L-arginine treatment, however, did not change lesion size after MCA occlusion in wild-type mice (Table 3).

TABLE 2

Physiological data 10 min before MCA occlusion and 24 hrs after ischemia

| | pH | | pCO2 (mmHg) | | pO2 (mmHg) | | MABP (mmHg) | |
|---|---|---|---|---|---|---|---|---|
| | before | after | before | after | before | after | before | after |
| Protocol 1 | | | | | | | | |
| Wt SV-129 | 7.33 ± 0.04 | 7.29 ± 0.06 | 42.2 ± 4.5 | 43.8 ± 6.6 | 153 ± 20 | 146 ± 29 | 98 ± 7 | 95 ± 6 |
| Wt C57 B/6 | 7.34 ± 0.05 | 7.35 ± 0.06 | 49.5 ± 3.1 | 51.1 ± 4.7 | 148 ± 30 | 137 ± 38 | 94 ± 7 | 96 ± 4 |
| eNOS mutant[a] | 7.33 ± 0.07 | 7.32 ± 0.08 | 47.2 ± 4.8 | 49.6 ± 7.3 | 139 ± 37 | 128 ± 35 | 115 ± 8 | 117 ± 9 |
| eNOS mutant[b] | 7.35 ± 0.04 | 7.30 ± 0.05 | 43.8 ± 5.9 | 47.3 ± 2.9 | 148 ± 16 | 139 ± 28 | 102 ± 6 | 102 ± |
| Protocol 2 | | | | | | | | |
| eNOS mutant | | | | | | | | |
| nitro-L-arginine | 7.36 ± 0.07 | 7.33 ± 0.05 | 47.6 ± 4.3 | 51.0 ± 2.9 | 120 ± 38 | 134 ± 35 | 110 ± 10 | 107 ± 9 |
| Vehicle | 7.32 ± 0.07 | 7.32 ± 0.07 | 44.6 ± 4.2 | 43.6 ± 6.3 | 129 ± 32 | 138 ± 32 | 113 ± 8 | 118 ± 8 |

TABLE 2-continued

Physiological data 10 min before MCA occlusion and 24 hrs after ischemia

| | pH | | pCO2 (mmHg) | | pO2 (mmHg) | | MABP (mmHg) | |
|---|---|---|---|---|---|---|---|---|
| | before | after | before | after | before | after | before | after |
| Wt SV-129 | | | | | | | | |
| nitro-L-arginine | 7.36 ± 0.04 | 7.35 ± 0.03 | 47.8 ± 3.5 | 49.3 ± 6.3 | 142 ± 17 | 158 ± 22 | 92 ± 4 | 97 ± 14 |
| Vehicle | 7.37 ± 0.04 | 7.36 ± 0.03 | 46.8 ± 4.4 | 45.6 ± 2.0 | 134 ± 35 | 146 ± 28 | 94 ± 5 | 98 ± 13 |

Data are expressed as means ± SD. n = 5–7 in each group.
[a]Hypertensive group;
[b]normotensive group treated with hydralazine.

TABLE 3

Effects of nitro-L-arginine on infarct size 24 hrs after middle cerebral artery occlusion in mice.

| | Infarct Volume (mm$^3$) | |
|---|---|---|
| | Wild-type | eNOS mutant |
| Vehicle | 94 ± 27 | 116 ± 13 |
| Nitro-L-arginine | 97 ± 13 | 88 ± 23* |

Data are expressed as mean ± SD. n = 8–12 in each group. *p < 0.05 vs vehicle.

Example 10

Measurement of rCBF in Wild-type and eNOS Mutant Mice Following MCA Occlusion

In randomly selected mice, rCBF was determined by laser-Doppler flowmetry (Perimed, PF2B, Stockholm, Sweden) and recorded on a MacLab/8 data acquisition system (AD Instruments, Milford, Mass.). Two fiberoptic probe tips (Perimed PF 319:2, diameter=0.5 mm) were fixed 2 mm posterior, 3 mm lateral to bregma and 2 mm posterior, 6 mm lateral to bregma on the ipsilateral hemisphere. These two coordinates identify sites on the convex brain surface within the vascular territory supplied by distal and proximal segments of the middle cerebral artery, respectively, and they correspond to peri-infarct zone and deeply ischemic territory, respectively. Yang et al. (1994); Huang et al. (1994). Steady-state baseline values were recorded before MCA occlusion. rCBF was recorded continuously during and after ischemia and expressed as percentage relative to the baseline value.

Figure 8:
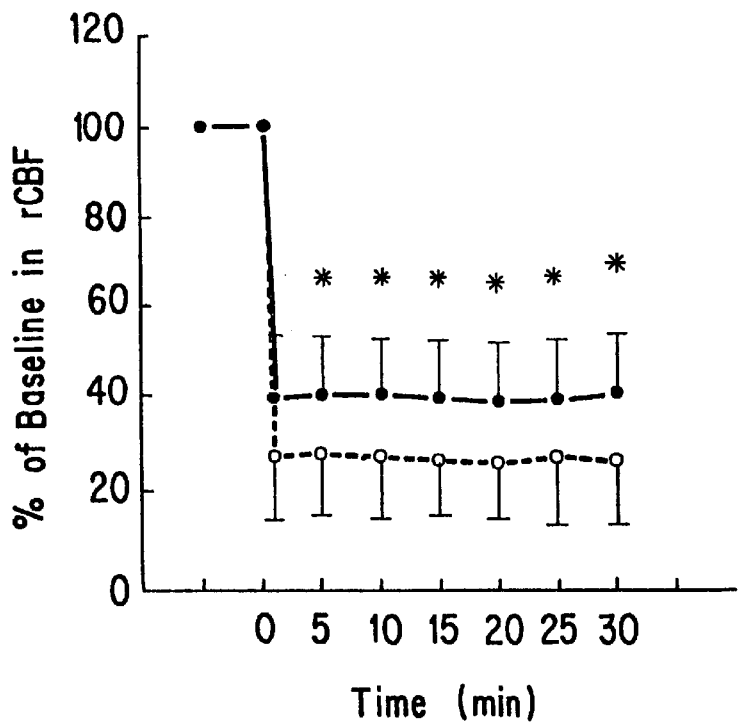
FIG. 8 depicts regional cerebral blood flow (rCBF) as measured by laser Doppler flowmetry after MCA occlusion in the periinfarct area of eNOS mutant mice (dotted line, n=11) as compared to wild-type SV-129 animals (continuous line, n=10, p<0.05). A greater rCBF reduction was noted in eNOS mutant mice as compared to wild-type mice. A flexible optic probe tip (diameter=0.5 mm) was secured 2 mm posterior and 3 mm lateral to bregma on the ipsilateral hemisphere. Steady-state rCBF values prior to occlusion were taken as a baseline (100%) and the subsequent changes after the onset of ischemia were shown as a percentage relative to baseline. Time zero represents the point of MCA occlusion. There were no significant differences in rCBF blood flow between SV-129 and C57 Black/6 wild-type mice.

As depicted in FIG. 8, rCBF reduction was greater in the zone corresponding to the per infarct area (30±16% of baseline, n=11), in eNOS mutant mice (p<0.05) as compared to SV-129 (40±13% of baseline, n=10), although there was no significant difference in the MCA core territory (data not shown).

Autoregulation Study

Mice were anesthetized with urethane (1.5 g/kg, ip) and ventilated (SAR-830 ventilator, CWE Inc., Ardmore, Pa.) with 70/30% nitrous oxide/oxygen after tracheostomy. Both femoral arteries were cannulated for arterial blood pressure measurement, blood gas determination and for blood withdrawal. Respiratory parameters were adjusted to keep the $P_aCO_2$ in normal ranges (30–40 mmHg). The core temperature was kept normothermic as above. The level of rCBF was monitored by laser Doppler flowmetry. Dalkara et al. (1995).

Following reflection of the skin and subcutaneous tissue, an rCBF probe tip was secured directly over the parietal skull with glue (Borden Inc, Columbus, Ohio), away from pial vessels. An initial rCBF recording was taken as 100% and subsequent flow changes were expressed relative to this value. After heparin (10 units, iv) administration, arterial blood pressure was lowered −10 mmHg every 5 min by withdrawing femoral artery blood (0.05–0.15 ml). Corresponding rCBF readings were averaged for each 10 mm Hg stepwise reduction. The duration of total experiment was approximately 2–2.5 hrs. The upper limit of autoregulation was not tested in these mice.

Figure 9:
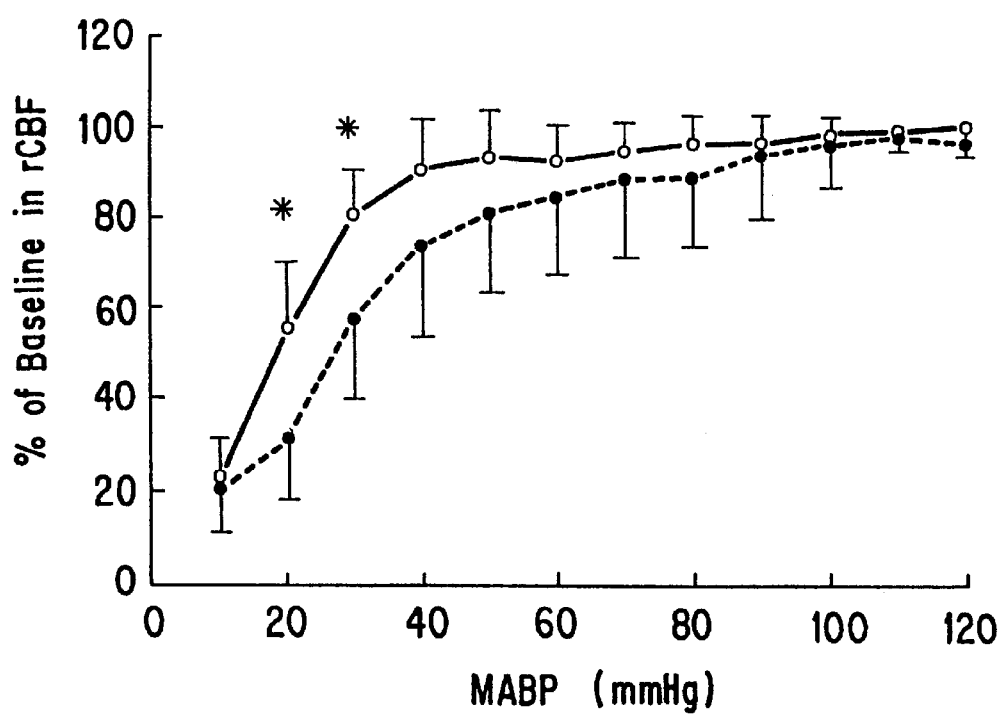
FIG. 9 depicts the effect of hemorrhagic hypotension on rCBF in urethane-anesthetized (dotted line) and wild-type animals (continuous line). Hypotension was induced by gradually withdrawing arterial blood as described infra, and rCBF was measured by laser Doppler flowmetry. The initial rCBF values were taken as 100% and the corresponding changes thereafter calculated as percentage relative to the initial value. The baseline MABF in wild-type and mutants were 104±12 (n=7) and 117±13 mm Hg (n=7), respectively. There was a greater tendency toward hypoperfusion at higher levels of MABP in the mutant animals. Data are expressed as mean ±SD. * signifies p<0.05 as compared to wild-type animals.

When arterial blood pressure was lowered step-wise by controlled hemorrhagic hypotension in wild-type mice, cerebral blood flow stayed relatively constant until<40 mmHg. However, as depicted in FIG. 9, at low blood pressures, the autoregulation curve was shifted slightly to the right in eNOS mutant animals, suggesting higher cerebrovascular resistance than wild type at lower perfusion pressures.

The data in Examples 9–10 demonstrate that deletion of the mouse eNOS gene is associated with larger brain infarcts and more pronounced rCBF reductions in corresponding brain regions after MCA occlusion. See FIG. 8. eNOS mutants also exhibit proportionally lower rCBFs at reduced perfusion pressures during controlled hemorrhagic hypotension. See FIG. 9. While the reduction in rCBF at reduced perfusion pressure may be due to hypertension in the eNOS mutant animal, no hypertensive changes were noted in the vessel wall or heart on preliminary histopathological analyses. The contribution of high blood pressure to infarct enlargement in eNOS animals was probably minor since infarct size did not change in eNOS mutants made normotensive by hydralazine administration.

Nitro-L-arginine decreased infarct volumes in eNOS mutant mice but not in wild-type animals. Since nNOS is the only constitutively expressed isoform in eNOS mutant mice, this decrease was likely caused by nNOS inhibition. However, the reductions after nitro-L-arginine treatment were not as large as expected (24% decrease) based on the observation in nNOS mutant, suggesting that either the degree of nNOS inhibition was small using the employed protocol or that undocumented factors such as systemic hypotension induced by nitro-L-arginine, may have attenuated an even greater reduction in infarct size.

Example 11

Increase in Blood Vessel Diameter After Nitro-L-arginine Superfusion in Wild-type and eNOS Mutant Mice The mouse head was fixed in a stereotaxic frame and the skull exposed by a longitudinal skin incision. A stainless steel cranial window ring (8.0 mm in inner diameter, 2.0 mm in height) containing three ports was imbedded into a loop of bone wax over the skull. Dental acrylic was then applied. A craniotomy (2×1.5 mm) was made in the left parietal bone within the ring of the window. After dura was opened and the brain surface superfused with artificial cerebrospinal fluid (aCSF), a cover glass was placed to close the window. The volume under the window was approximately 0.1 ml. The composition of aCSF was as follows (in mMol/L): $Na^+$ 156.5, $K^+$ 2.95, $Ca^{++}$ 1.25, $Mg^{++}$ 0.67, $Cl^-$ 138.7, $HCO_3^-$ 24.6, dextrose 3.7 and urea 0.67. The pH value of aCSF was kept at 7.35–7.45, and monitored continuously with a pH meter (Corning Inc., Corning, N.Y.). The aCSF was superfused by an infusion pump (0.4 ml/min) via a PE-100 tubing connected to a window port. Intracranial pressure was maintained at 5–8 mm Hg. The temperature of aCSF within the windows was maintained at 36.5–37.0° C.

Pial vessels were visualized through a cranial window by an intravital microscope (Leitz, Germany) equipped with a video camera (C2400, Hamamatsu Photonics, Hamamatsu, Japan). The diameter of a single pial arteriole (20–30 µm) was continuously measured by a video width analyzer (C3161, Hamamatsu, Japan) and recorded using the MacLab data acquisition and analysis system. After baseline stabilization, nitro-L-arginine or nitro-D-arginine solution (1 mM) was superfused into the window and the diameter of pial arteriole measured continuously 40 min thereafter.

Figure 10:
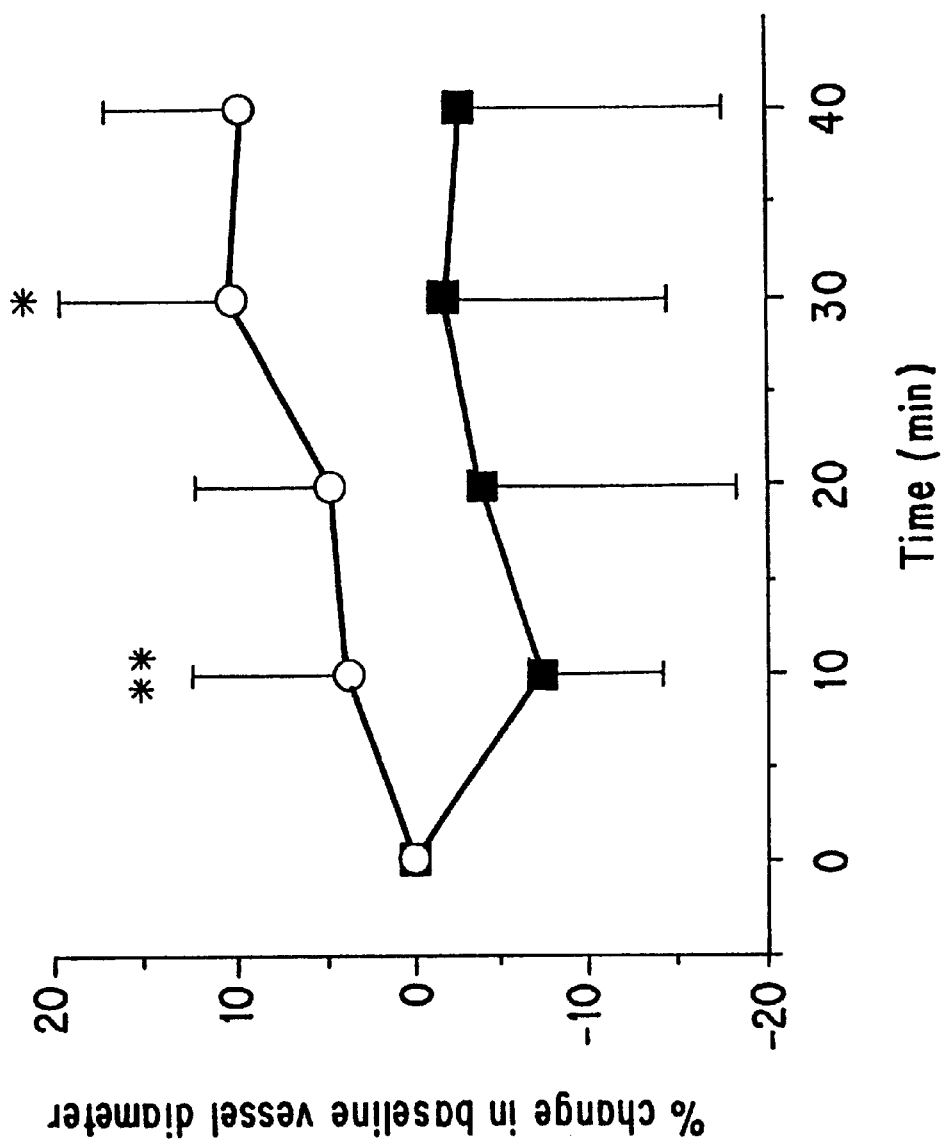
FIG. 10 shows that the diameter of pial arterioles was increased in eNOS mutant mice (circle, n=7), but not in wild-type (square, n=8) mice after nitro-L-arginine superfusion in a closed cranial window. Nitro-L-arginine (1 mM) was topically superfused for 40 minutes. Superfusion of nitro-D-arginine (1 mM, n=3) did not affect the diameter of pial arterioles in eNOS mutant mice (data not shown). The data are calculated as percent from baseline and expressed as mean ±SD. * indicates p<0.05 and ** indicates p<0.01 vs. wild-type.

As depicted in FIG. 10, unlike wild-type mice, nitro-L-arginine superfusion alone increased vessel diameter in eNOS mutant animals, reaching maximum at 30 min (p<0.05 vs wild-type). Similar changes in rCBF were recorded in preliminary experiments by laser Doppler flowmetry using the closed cranial window technique (data not shown). There was no change in MABP during nitro-L-arginine superfusion. No change was found in pial diameter after nitro-D-arginine superfusion in eNOS mutant mice (data not shown).

In the eNOS mutant, nitro-L-arginine superfusion inhibits nNOS within subjacent brain parenchyma, and there is published evidence for a contribution from parenchymally-derived NO to cerebrovascular tone. Iadecola et al, 1994. This example provides evidence that nitro-L-arginine may directly decrease tone in resistance vessels or surrounding tissues of eNOS mutants by showing that nitro-L-arginine superfusion dilates pial arterioles in these mutants. However, the mechanism remains unknown.

NO is a potent vasodilator and it, or a closely related chemical, is proposed as EDRF or endothelium-derived relaxing factor. Ignarro et al. (1987); Palmer et al. (1988). This is evidence to support the hypothesis that endothelium-derived NO or reaction product may be beneficial to stroke by augmenting rCBF in ischemic territory. Infusion of L-arginine, a substrate for NOS, caused NO-dependent vasodilation and increased rCBF distal to MCA occlusion in rats. Morikawa et al. (1994a). Dynamic susceptibility contrast magnetic resonance imaging also suggests that L-arginine infusion cerebral blood flow and blood volume. Hamberg et al. (1993). Zhang et al. (1994) reported that NO donors improved rCBF in the ischemic area and reduced infarct size as well. In addition, sectioning of NOS-containing parasympathetic cerebrovascular fibers in sphenopalatine ganglia, Nozaki et al. (1993), increased infarct size after focal ischemia, Kano et al. (1991), and reduced cerebral perfusion during hemorrhagic hypotension. Koketsu et al. (1992). The above evidence coupled with our observation that arterial blood pressures are less stable in eNOS mutant animals, e.g., during hypercapnic challenge, shows the importance of eNOS regulation of vascular hemodynamics and its potential importance to stroke outcome.

eNOS mutant mice maybe more susceptible to ischemic injury because NO modulates the microcirculation. NO may also block leukocyte adhesion and decrease microvascular stasis often seen following MCA occlusion. Garcia et al. (1993). Kubes et al. (1991) reported that superfusing mesenteric vessels with NOS inhibitors increased leukocyte adhesion. Kurose et al. (1994) found that L-arginine attenuated ischemia-induced platelet-leukocyte aggregation, mast cell degranulation and albumin extravasation. We also found that rCBF was more severely reduced in homologous brain areas after MCA occlusion in eNOS but not nNOS mutant mice. Huang et al. (1994). These findings confirm that NO plays a role in the modulation of the microcirculation which may contribute to the outcome of ischemia.

eNOS inhibition may account for the increases in infarct size in some studies after nitro-L-arginine, particularly after large doses. Yamamoto et al. (1992); Zhang and Iadecola (1993); Morikawa et al. (1994b). By contrast, neuroprotection was reported after selective nNOS inhibition with 7-nitroindazole, Yoshida et al. (1994), or FPL17477, Zhang et al. (1995). Consistent with present findings, infarction size increased when nitro-L-arginine was administered to mutant mice expressing only the eNOS isoform (i.e., nNOS knockout mouse). Importantly, iNOS enzyme activity is not measurable in mouse (SV-129 strain) brain for at least 4 days after permanent MCA occlusion. Yoshida et al. (1995).

We conclude that NO possesses a dual role in focal cerebral ischemia. Depending upon its source, NO may be toxic or protective to brain under ischemic conditions. Parenchymal NO overproduction may lead to neurotoxicity whereas endothelial NO may protect brain tissue by increasing rCBF or some other hemodynamic mechanism. These results emphasize the importance of knockout mice to dissect the role of individual proteins in these pathophysiological events.

Example 12

Brain Distribution of NOS in Wild-type and Mutant Mice

Experimental Procedures

Animals

Adult male wild-type, SV-129 and C57black/6 (Taconic Farms, Germantown, N.Y., U.S.A.), and adult male and female nNOS mutant, Huang et al., *Cell* 75:1273–1286 (1993), and eNOS mutant mice weighing 22 to 29 g and adult male Wistar rats (Charles River, Mass., U.S.A.) weighing 250 to 300 g were allowed free access to food and water.

Tissue Preparation

Mice and rats were sacrificed by decapitation under 2% halothane anesthesia (30% $O_2$+70% $N_2O$). The brains were rapidly removed, immediately frozen in powdered dry ice, and stored at −70° C. Twelve µm sagittal or coronal sections were cut in a cryostat-microtome at −18° C. (Leitz 1720, Leica, Deerfield, Ill., U.S.A.) and thaw-mounted onto gelatin-coated slides (1% gelatin and 0.1% $KCr_2O$). Adjacent sections were stained with cresyl violet and hematoxylin eosin, and stored at −70° C.

[$^3$H]L-NG-Nitro-arginine Autoradiographic Binding Assay

The method for the autoradiographic visualization of NOS binding using [$^3$H]L-NG-Nitro-arginine ([$^3$H]L-NA) has been described previously. Rutherford et al., (1995). Prior to experiments, sections were brought to −20° C. and then to room temperature. Sections were preincubated for 15 min at room temperature in 50 mM Tris-HCl (pH 7.3) to remove the endogenous ligands and/or modulators, then incubated for 30 min at room temperature in 50 mM Tris-HCl buffer containing 10 μM $CaCl_2$ and 25 nM $N^G$-nitro-L-[2,3,4,5-H]arginine hydrochloride ([$^3$H]L-NA, specific activity: 48–57 Ci/mmol, Amersham, Arlington Heights, Ill., U.S.A.). Unlabelled L-$N^G$-nitro-arginine (L-NA, Sigma, St. Louis, Mo., U.S.A.), D-$N^G$-nitro-arginine (D-NA, RBI, Natick, Mass., U.S.A.) and 7-nitroindazole (7-NI, Cookson Chemicals Ltd., England) was added at concentrations of 10, 10, and 100 μM, respectively. The sections were then washed twice for 5 min in ice-cold buffer and rinsed for 10 sec in ice-cold distilled water to eliminate residual buffer. After drying with cold air, the slides were tightly apposed to $^3$H-Hyperfilm (Amersham) together with tritiated polymer standards (Amersham) and exposed at −4° C. for 6 weeks.

Densitometric Analysis

Films were developed in Kodak D-19 and fixed in Kodak Rapid Fixer, according to the manufacturer's instructions. The optical density of the regions of interest was measured by a computer-assisted image analysis (System M4, Imaging Research, St. Catharines, Ontario, Canada). The relationship between optical density and radioactivity was examined with reference to the tritium standards (Amersham, [$^3$H] microscale) co-exposed with the tissue sections. The optical density of the brain regions measured in the present study was in a range in which the optical density and the radioactivity of the $^3$H-microscale showed a near linear relationship. The densities of NOS binding sites are expressed in fmol bound [$^3$H]L-NA/mg tissue using the [$^3$H]L-NA concentration of 25 nM.

NOS Catalytic Activity

NOS activity was measured by the conversion of [$^3$H] arginine to [$^3$H]citrulline according to the method described by Bredt et al. (1990b) with minor modifications. Samples were homogenized in 500 μl cold 50 mM HEPES buffer (Research Organics Inc., Ohio, U.S.A.) containing 1 mM EDTA (pH 7.4, Sigma). Homogenates were centrifuged at 500×g for 5 min. at 4° C. and the supernatant used for assay. The incubation mixture contained 100 μl HEPES (50 mM, pH 7.4), EDTA (1 mM), reduced β-nicotinamide adenine dinucleotide phosphate (β-NADPH, 1 mM, Sigma), dithiothreitol (1 mM, Sigma), calmodulin (10 μg/ml, Calbiochem, CA, U.S.A.) and $CaCl_2$ (1 mM) and 25 μl of 100 mM L-[$^3$H]arginine (1 mCi, Dupont NEN, Mass., U.S.A.). The reaction was started by adding the supernatant (25 μl) and stopped after 20 min incubation at 37° C. by adding HEPES buffer (20 mM, pH 5.5) containing EDTA (2 mM), pH 5.5. The mixture was then applied to cation-exchange columns containing Dowex AG50WX-8 ($Na^+$ form; Bio-Rad, Richmond, Va., U.S.A.) and eluted with 2 ml of distilled water. [$^3$H]Citrulline was measured within eluates by a scintillation spectrometry (Packbeta 1209, LKB, Gaithersburg, Md., U.S.A.).

Statistical Analysis

Data are presented as mean ±SE. Statistical comparisons were made by one-way ANOVA and Tukey's multiple-range test or Student's t-test using the software super ANOVA (Abacus Concepts, Berkeley, Calif., U.S.A.).

Results

Figure 12A:
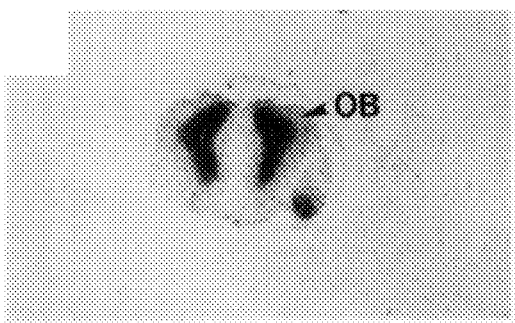
FIGS. 12A–12H depict the autoradiographic distribution of [$^3$]L-NA binding in coronal sections of SV-129 wild-type mouse brain.
Figure 12B:
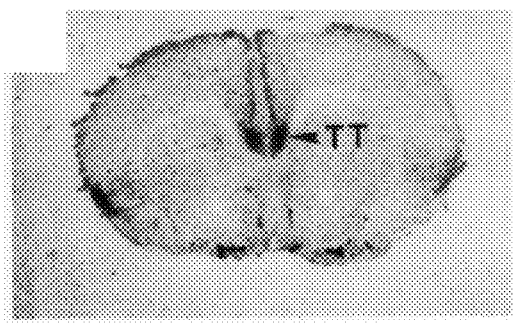
Figure 12C:
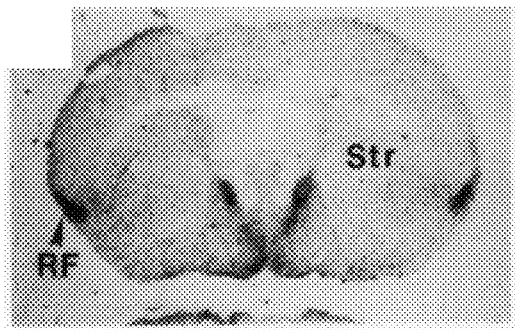
Figure 12D:
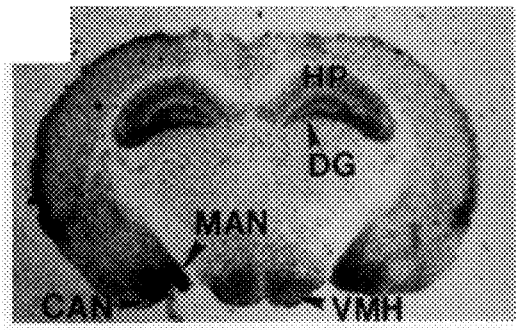
Figure 12E:
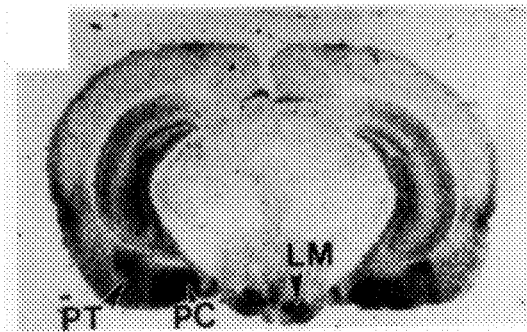
Figure 12F:
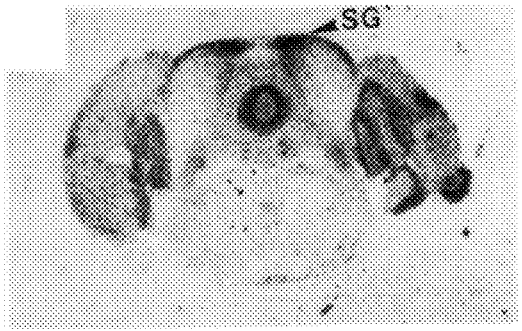
Figure 12G:
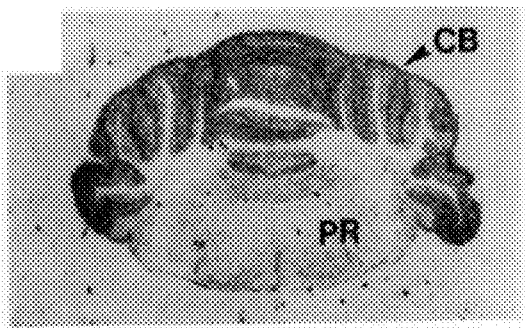
Figure 12H:
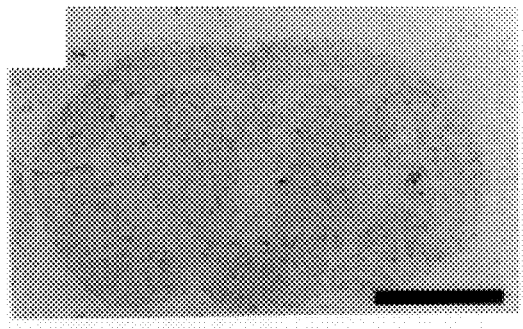
Figure 13:
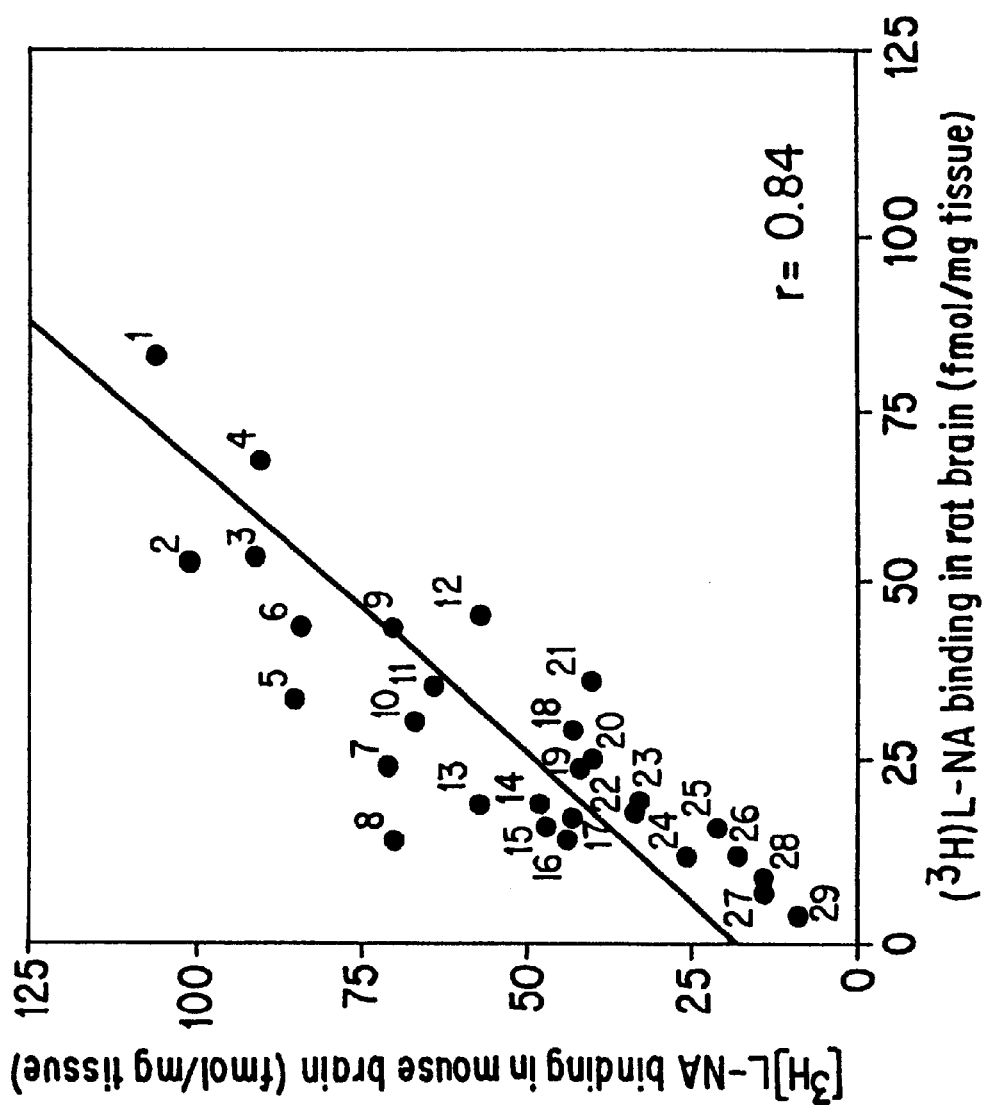
FIG. 13 depicts the correlation between [$^3$H]L-NA binding in mouse and rat brain. 1: granular layer of olfactory bulb, 2: amygdaloid nuclei-posteromedial cortical, 3: amygdaloid piriform transition, 4: amygdaloid nuclei-medial, 5: taenia tecta, 6: rhinal fissure, 7: lateral mammillary nucleus, 8: hippocampal CA3 subfield, 9: amygdaloid nuclei-basomedial, 10: superficial grey layer of superior colliculus, 11: molecular layer of cerebellum, 12: amygdaloid nuclei-anterior cortical, 13: dentate gyrus, 14: amygdaloid nuclei-central, 15: I and II layers of occipital cortex, 16: hippocampal CA1, 17: dorsal tegmental nucleus, 18: plexiform layer of olfactory bulb, 19: I and II layers of frontal cortex, 20: ventromedial hypothalamic nuclei, 21: granule layer of cerebellum, 22: dorsomedial hypothalamic nuclei, 23: medial mammillary nucleus, 24: III to VI layers of occipital cortex, 25: III to VI layers of frontal cortex, 26: striatum, 27: pontine reticular nucleus, 28: posterior thalamus nuclei, 29: ventral posteromedial thalamus nuclei. Values in mouse and rat brain represent the mean of five SV-129 mice and three rats, respectively.

Regional Distribution of [$^3$H]L-$N^G$-nitro-arginine Binding in the 4 Mouse Strains (FIGS. 11–13, Table 4)

Figure 11A:
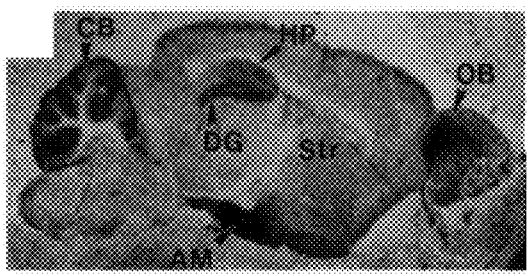
FIGS. 11A–11D depict the autoradiographic distribution of [$^3$H]L-NA binding in sagittal brain sections of wild-type and mutant mice.
Figure 11B:
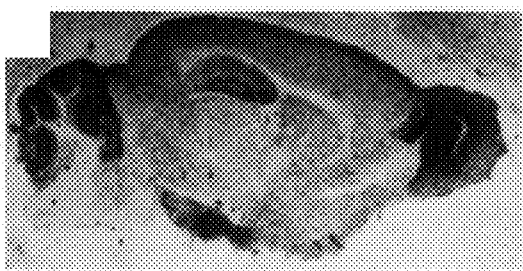

[$^3$H]L-NA binding was heterogeneously distributed in wild-type (SV-129 and C57Black/6) mouse brain, with highest densities (>90 fmol/mg tissue) associated with the granular layer of the olfactory bulb, the medial amygdaloid nuclei, posteromedial cortical amygdaloid nuclei and amygdaloid piriform transition. Also, the islands of Calleja, tenia tecta, rhinal fissure, hippocampal CA3 subfield, dentate gyrus, anterior cortical and basomedial amygdaloid nuclei, lateral mammillary nucleus, superficial grey layer of the superior colliculus and cerebellar molecular layer contained high densities of [$^3$H]L-NA (50–90 fmol/mg tissue). Other area of prominent binding (30–50 fmol/mg tissue) were the plexiform layer of the olfactory bulb, cortical layers I–II, hippocampal CA1 subfield, dorsomedial and ventromedial hypothalamic nuclei, central amygdaloid nuclei and granule layer of cerebellum. The striatum and pontine reticular nucleus showed relatively poor binding (<20 fmol/mg tissue) (FIGS. 11A, 11B and 12, Table 4). Binding was not significantly different from background in cortical layers III–VI, posterior and ventral posteromedial thalamus nuclei and medial mammillary nucleus (FIGS. 11A, 11B and 12).

Figure 11C:
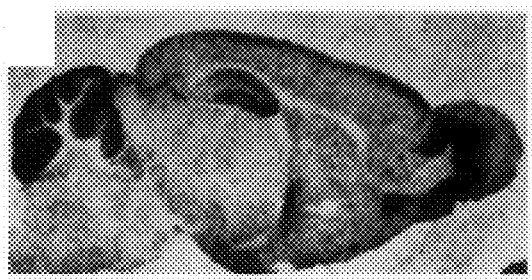

The density of [$^3$H]L-NA binding in nNOS mutant mice was significantly decreased in all regions (FIG. 11D). [$^3$H] L-NA in eNOS mutant mice was similar to wild-type mice (FIG. 11C, Table 4).

The distribution of [$^3$H]L-NA binding was similar in mouse and rat brain as shown in FIG. 13. Although the binding was relatively higher in mouse brain.

Effects of 7-NI on [$^3$H]L-$N^G$-nitro-arginine Binding (FIG. 14 and Table 5)

In the presence of 7-NI (100 μM), [$^3$H]L-NA binding was significantly decreased in all regions measured in wild-type (FIG. 14) and eNOS mutant mice, but not in nNOS mutant mice. In the presence of 7-NI, the densities of [$^3$H]L-NA binding did not show significant differences between wild-type, eNOS mutant and nNOS mutant mice (Table 5).

Effects of L-NA and D-NA on [$^3$H]L-$N^G$-Nitro-arginine Binding (FIGS. 11, 14 and Table 6)

Figure 11D:
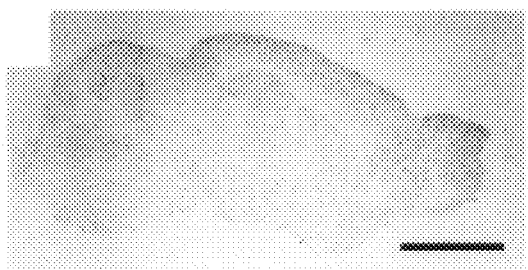
Figure 14A:
Figure 14B:
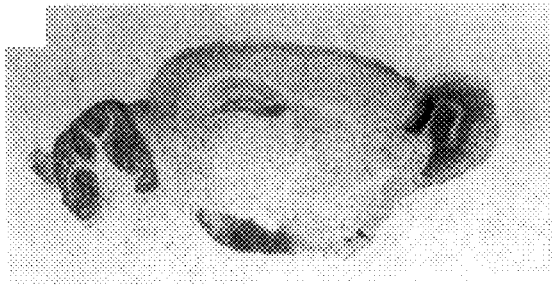
Figure 14C:
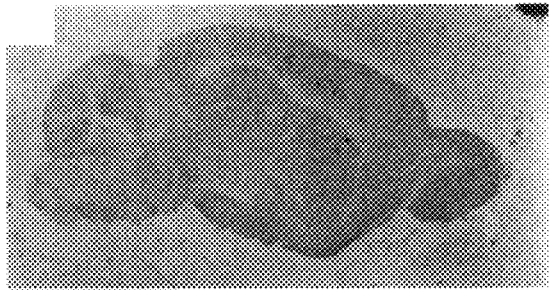
Figure 14D:
Figure 15A:
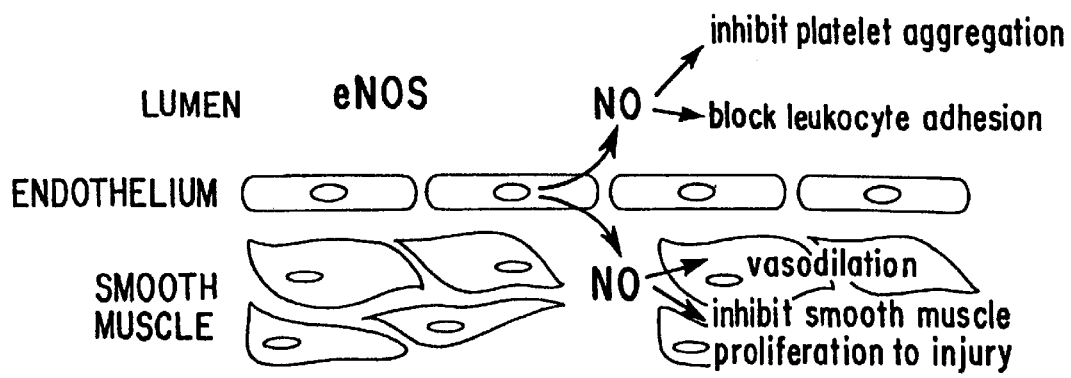
FIGS. 15A–15B are schematics showing the effects of nitric oxide produced from various NOS isoforms in normal and atherosclerotic arteries.
Figure 15B:
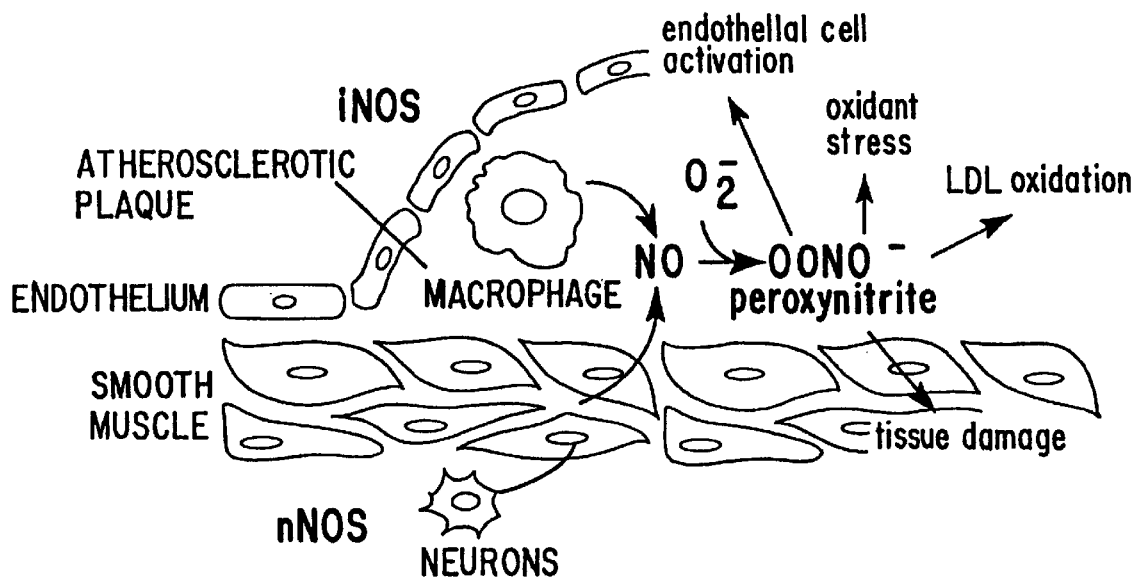

In the presence of L-NA (10 μm), the density of [$^3$H]L-NA binding sites was very low in all brain regions of all mouse strains (FIGS. 11D, 12H). In the presence of D-NA (10 μM), the density of [$^3$H]L-NA binding sites was decreased by approximately 20 to 30% in SV-129 mice (FIGS. 14A, 14B, Table 6). Both L-NA and D-NA decreased slightly the binding to the gelatinized slide itself (FIGS. 14C, 14D). Binding in brain of the nNOS mutant mice was not significantly higher than background in any regions (FIG. 11D).

NOS Catalytic Activity (Table 7)

The highest NOS catalytic activities in SV-129 mice were found in the cerebellum, thalamus/hypothalamus and cerebral cortex/amygdala. Moderate activities were observed in the brain stem, hippocampus, olfactory bulb and striatum. The activities in eNOS mutant mouse brain were similar to those found in SV-129. In nNOS mutant mice NOS activity was dramatically reduced in all regions investigated. Very low levels of residual NOS catalytic activity were measured in type 1 mutant mice (0–1.7% of SV-129) (Table 7).

Discussion

In this Example, the distribution and density of [$^3$H]L-NA NOS binding sites in the brains of wild-type, eNOS mutant mice, and nNOS mutant mice was examined using quantitative in vitro autoradiography. Previous studies showed that [$^3$H]L-NA binds specifically and stereospecifically to the nNOS isoform in the rat brain. Kidd et al. (1995); Michel et al. (1993). Specific binding of [$^3$H]L-NA to the endothelium of placental blood vessels was recently established by Rutherford et al. (1996) using in vitro autoradiography. Using similar techniques, we recently observed specific [$^3$H]L-NA binding to pig aortic endothelium, which is displaceable by unlabelled L-NA. Hence, this ligand can detect the presence of both eNOS and nNOS by in vitro autoradiography.

The highest density of [$^3$H]L-NA binding was observed in the olfactory bulb, the amygdaloid complex, the islands of Calleja, and the cerebellum (FIG. 12). In general, these regions exhibit the highest NADPH-diaphorase activity and brain NOS positive immunostaining in the mouse, Huang et al. (1993), and in the rat, Schmidt et al. (1992); Vincent et al. (1992). Thus, the density and distribution of [$^3$H]L-NA binding presumably reflects the density and distribution of nNOS, the predominant isoform in brain which comprises more than 95% of NOS activity in the brain.

While the density and distribution of binding was similar in the two wild-type strains, it was relatively higher in mouse than rat brain (FIG. 13). In particular, higher binding was detected in the hippocampus of the mouse which may correspond to the greater NADPH-diaphorase activity reported in mouse CA1 pyramidal cells. Wallace et al. (1992). Because activity of the inducible isoform, type 2 NOS (iNOS), is undetectable in normal mouse brain, Yoshida et al. (1995), it is unlikely to be a major source for [$^3$H]L-NA binding in our studies. The values of [$^3$H]L-NA binding in our rat study were higher than those of Kidd et al. (1995), although the rank order of binding activity in rat brain regions was similar in both studies. Id. These discrepancies may be due to strain differences or different concentrations of added [$^3$H]L-NA.

[$^3$H]L-NA binding in nNOS mutant mice was remarkably lower than wild-type or eNOS mutant mice and the L-NA displaceable [$^3$H]L-NA binding was distributed diffusely throughout the brain (Table 4). Thus, it is presumed that the loss of [$^3$H]L-NA binding reflected the absence of nNOS. The residual binding probably did not reflect the labeling of eNOS, since the binding in nNOS mutant brain was not stereoselective and could be displaced by both L- and D-NA.

D-NA displaceable binding, detectable in brain of both wild-type strains, may represent an additional binding site for L-arginine unrelated to NOS protein. The fact that both L-NA and D-NA were able to decrease [$^3$H]L-NA binding to the gelatinized glass slide (see FIG. 14) suggests that the D-NA-displaceable component of [$^3$H]L-NA binding is nonspecific. Therefore, "specific" binding should not be equated with "displaceable" binding, especially when the displacer is the unlabelled tracer, or closely related to the tracer.

Michel et al. (1993) reported that L-NA and D-NA displaced [$^3$H]L-NA binding with pI$_{50}$ values, i.e., the logarithm of the concentration of competing compound causing 50% inhibition of [$^3$H]L-NA binding, of 7.1 and 3.1 (log molar concentration), respectively. Hence 10 $\mu$M D-NA is unlikely to affect the [$^3$H]L-NA labelling of specific NOS binding sites and could be used to mask part of the non-specific component of [$^3$H]L-NA binding.

There was no significant difference between [$^3$H]L-NA binding in eNOS mutant and wild-type mice (FIG. 11, Table 4). Furthermore, NOS enzymatic activity in eNOS mutant mice was almost the same as that in wild-type mice (Table 7). Therefore, these results indicate that the expression of eNOS is low in the mouse brain. However, Dinerman et al. (1994) reported the presence of eNOS in the hippocampal pyramidal cells, the cerebellum and olfactory bulb by immunohistochemistry in the rat brain. This discrepancy may reflect species differences and/or the technical differences between quantitative autoradiography and immunohistochemistry.

[$^3$H]L-NA binding was inhibited by 7-NI in wild-type and eNOS mutant mice, but not in nNOS mutant mice (Table 5). Hence, the results indicate that binding site of 7-NI in the mouse brain is mainly to nNOS. 7-NI and related substituted indazoles are potent and competitive nNOS inhibitors, Babbedge et al. (1993); Moore et al. (1993a); Moore et al. (1993b), and have been useful for treatment of focal ischemia damage in vivo, Yoshida et al. (1994), MPTP neurotoxicity in vivo, Schulz et al. (1995a) and NMDA-induced excitotoxicity in vivo, Schulz et al. (1995b). 7-NI may also compete with L-arginine for binding to the prosthetic heme group, and affect the pteridine site of the enzyme. Mayer et al. (1994). The mechanism of selective nNOS inhibition remains unclear. However, 7-NI at 10 mg/kg i.p., decreases NOS catalytic activity by approximately 30 to 40% within the mouse cerebellum, cerebral cortex and hippocampus. Moore et al. (1993); Moore et al. (1993). 7-NI does not increase blood pressure, like other NOS inhibitors. Babbedge et al. (1993). Moreover, the similarity in [$^3$H]L-NA binding in eNOS mutant mice and wild-type mice further supports the use of eNOS mutant mice to screen compounds for use in the treatment or prevention of cerebral ischemia or stroke.

Conclusion

This regional distribution of [$^3$H]L-NA binding was similar to that seen with the NADPH-diaphorase method. The density of [$^3$H]L-NA binding in nNOS mutant mice was dramatically reduced in all regions, compared with wild-type mice, but not eNOS mutant mice. nNOS in mouse brain may represent the majority of [$^3$H]L-NA binding sites. [$^3$H]L-NA autoradiography may provide a useful method for estimating the distribution of NOS, effects of drugs and pathogenesis of NO-related diseases such as stroke, Alzheimer's disease and tumor. For example, it should be useful for estimating regional changes in NOS binding after cerebral ischemia.

TABLE 4

Regional distribution of L-NA displaceable ($^3$H]L-N$^G$-nitro-arginine binding in wild-type (SV-129 and C57black/6) and mutant (eNOS and nNOS mutant) mice.

| Brain regions | Wild-type | | Mutant | |
|---|---|---|---|---|
| | SV-129 | C57black/6 | eNOS | nNOS |
| Olfactory bulb-granular layer | 106 ± 2.5 | 101 ± 12.1 | 108 ± 3.8 | 13 ± 1.6*,#,+ |
| Olfactory bulb-plexiform layer | 43 ± 3.1 | 32 ± 3.1 | 33 ± 1.6 | 18 ± 0.6*,#,+ |
| Islands of Calleja | 71 ± 7.9 | 70 ± 13.7 | 51 ± 3.5 | 5 ± 0.6*,#,+ |
| Tenia tecta | 85 ± 6.7 | 106 ± 8.0 | 94 ± 6.1 | 13 ± 0.6*,#,+ |
| Rhinal fissure | 84 ± 5.2 | 80 ± 5.8 | 70 ± 3.9 | 17 ± 2.0*,#,+ |
| Striatum | 18 ± 1.4 | 16 ± 1.7 | 12 ± 0.7 | 9 ± 0.7*,# |
| Frontal cortex I-II | 40 ± 1.4 | 40 ± 3.0 | 32 ± 2.6 | 19 ± 1.5*,#,+ |
| Occipital cortex I-II | 47 ± 4.6 | 42 ± 5.9 | 36 ± 3.9 | 16 ± 0.9*,#,+ |
| Hippocampal CA1 subfield | 44 ± 2.4 | 42 ± 5.1 | 43 ± 2.3 | 13 ± 1.3*,#,+ |

TABLE 4-continued

Regional distribution of L-NA displaceable ($^3$H]L-N$^G$-nitro-arginine binding in wild-type (SV-129 and C57black/6) and mutant (eNOS and nNOS mutant) mice.

| | Wild-type | | Mutant | |
|---|---|---|---|---|
| Brain regions | SV-129 | C57black/6 | eNOS | nNOS |
| Hippocampal CA3 subfield | 70 ± 2.5 | 63 ± 4.0 | 63 ± 2.2 | 13 ± 1.1*,#,+ |
| Dentate gyrus | 57 ± 4.6 | 56 ± 4.0 | 52 ± 1.1 | 14 ± 1.2*,#,+ |
| Dorsomedial hypothalamic nuclei | 34 ± 2.6 | 25 ± 4.2 | 29 ± 6.0 | 12 ± 1.4* |
| Ventromedial hypothalamic nuclei | 42 ± 5.8 | 47 ± 7.4 | 45 ± 5.9 | 13 ± 1.8*,#,+ |
| Amygdaloid complex | | | | |
| Amygdaloid nuclei-medial | 90 ± 5.6 | 96 ± 8.8 | 89 ± 4.2 | 14 ± 2.2*,#,+ |
| Amygdaloid nuclei-anterior cortical | 57 ± 7.9 | 73 ± 8.6 | 69 ± 5.7 | 15 ± 2.9*,#,+ |
| Amygdaloid nuclei-basomedial | 70 ± 5.7 | 53 ± 7.7 | 63 ± 8.2 | 13 ± 1.9*,#,+ |
| Amygdaloid nuclei-central | 48 ± 6.5 | 41 ± 2.4 | 33 ± 4.4 | 14 ± 2.1*,#,+ |
| Amygdaloid nuclei-posteromedial cortical | 101 ± 5.0 | 98 ± 5.7 | 98 ± 3.5 | 15 ± 1.5*,#,+ |
| Amygdaloid piriform transition | 91 ± 6.3 | 93 ± 5.9 | 87 ± 5.1 | 13 ± 0.7*,#,+ |
| Lateral mammillary nucleus | 71 ± 6.3 | 52 ± 5.4 | 52 ± 3.7 | 13 ± 1.6*,#,+ |
| Superficial grey layer superior colliculus | 67 ± 4.4 | 54 ± 4.4 | 61 ± 5.4 | 16 ± 3.3*,#,+ |
| Cerebellum | | | | |
| Molecular layer | 64 ± 4.2 | 70 ± 4.9 | 67 ± 7.0 | 14 ± 3.0*,#,+ |
| Granule layer | 40 ± 2.2 | 42 ± 4.6 | 42 ± 3.6 | 13 ± 2.7*,#,+ |
| Pontine reticular nucleus | 14 ± 1.3 | 10 ± 1.9 | 10 ± 0.4 | 6 ± 1.4* |

Values (fmol/mg tissue) represent mean ± S.E. of five mice per group and were determined by subtracting binding remaining in the presence of 10 μM L-NA from the total binding in serial sections.
*p < 0.01 vs. SV-129,
p < 0.01 vs. C57 black,
+p < 0.01 vs. type 3 mutant (Turkey's multiple range test).

TABLE 5

Effects of 7-NI on the regional distribution of [$^3$H]L-NA binding in wild-type (SV-129 and C57black/6) and mutant (type 3 and type 1) mice.

| | Wild-type | | Mutant | |
|---|---|---|---|---|
| Brain regions | SV-129 | C57black/6 | eNOS | nNOS |
| Olfactory bulb (glanular layer) | | | | |
| L-NA displaceable[1] | 109 ± 1.9 | 113 ± 9.9 | 106[3] | 33 ± 1.9 |
| 7-NI[2] | 17 ± 0.7 | 28 ± 4.1* | N.T. | 30 ± 2.7 |
| Hippocampal CA3 subfield | | | | |
| L-NA displaceable | 60 ± 3.1 | 53 ± 2.3 | 50 ± 6.2 | 25 ± 0.9 |
| 7-NI | 18 ± 1.8* | 22 ± 4.7* | 21 ± 1.8* | 23 ± 2.3 |
| Dentate gyrus | | | | |
| L-NA displaceable | 48 ± 2.6 | 58 ± 5.6 | 58 ± 5.4 | 28 ± 2.2 |
| 7-NI | 18 ± 0.7* | 22 ± 4.6* | 20 ± 2.7* | 22 ± 1.7 |
| Amygdaloid complex | | | | |
| L-NA displaceable | 90 ± 4.9 | 89 ± 11.3 | 88 ± 2.9 | 29 ± 1.4 |
| 7-NI | 21 ± 2.1* | 21 ± 4.8* | 21 ± 2.9* | 23 ± 2.5 |
| Cerebellum (molecular layer) | | | | |
| L-NA displaceable | 67 ± 1.7 | 78 ± 6.8 | 67 ± 5.8 | 30 ± 0.8 |
| 7-NI | 18 ± 1.3* | 23 ± 5.4* | 20 ± 2.2* | 24 ± 1.0 |

Values (fmol/mg tissue) represent mean ± S.E. of three mice per group.
[1]L-NA displaceable = (total - binding in the presence of 10 μM L-NA) binding
[2]7-NI = L-NA displaceable binding in the presence of 100 μM 7-NI,
[3]n = 1, N.T.: not tested,
*p < 0.01 vs. L-NA displaceable. There are no significant differences between L-NA displaceable and 7-NI groups in type 1 mice.

TABLE 6

Effects of D-nitro-arginine (D-NA) on the regional distribution of [$^3$H]L-NA binding in wild-type (SVC-129) and nNOS mutant mice.

| Brain Regions | Binding | SV-129 | nNOS mutant |
|---|---|---|---|
| Olfactory bulb (granular layer) | | | |
| | L-NA displaceable[1] | 121 ± 12.4 | 32 ± 2.3[#] |
| | D-NA[2] | 92 ± 10.8 | 5 ± 3.0[*,#] |
| Hippocampal CA3 subfield | | | |
| | L-NA displaceable | 83 ± 2.4 | 33 ± 4.2[#] |
| | D-NA | 66 ± 5.9 | 3 ± 1.9[*,#] |
| Dentate gyrus | | | |
| | L-NA displaceable | 67 ± 3.7 | 33 ± 5.5[#] |
| | D-NA | 43 ± 4.8 | 2 ± 1.9[*,#] |
| Amygdaloid complex | | | |
| | L-NA displaceable | 96 ± 12.6 | 32 ± 5.9[#] |
| | D-NA | 64 ± 7.6 | 3 ± 1.7[*,#] |
| Cerebellum (molecular layer) | | | |
| | L-NA displaceable | 86 ± 4.5 | 32 ± 6.2[#] |
| | D-NA | 59 ± 6.7 | 0 ± 3.6[*,#] |

Values (fmol/mg tissue) represent mean ± S.E. of four to five mice per group.
[1]L-NA displaceable = (total - binding remaining in the presence of 10 $\mu$M L-NA) binding;
[2]D-NA = L-NA displaceable binding in the presence of 10 $\mu$M D-NA,
*$p < 0.01$ vs. L-NA displaceable, #$p < 0.01$ vs. SV-129

TABLE 7

NOS catalytic activity in SV-129, eNOS mutant and nNOS mutant mice.

| | NOS catalytic activity (fmol/mg wet weight/min) | | |
|---|---|---|---|
| Brain regions | SV-129 | eNOS mutant | nNOS mutant |
| Olfactory bulb | 3.1 ± 0.9 | 4.0 ± 1.2 | 0 ± 0[#] |
| Striatum | 2.4 ± 0.3 | 2.4 ± 0.8 | 0.04 ± 0.04[*,#] |
| Thalamus/Hypothalamus | 6.2 ± 1.8 | 5.8 ± 1.2 | 0.07 ± 0.04[*,#] |
| Hippocampus | 3.1 ± 0.9 | 3.2 ± 0.5 | 0.03 ± 0.03[*,#] |
| Cerebral cortex/Amygdala | 4.0 ± 1.0 | 4.0 ± 0.7 | 0.07 ± 0.02[*,#] |
| Cerebellum | 9.0 ± 2.0 | 7.3 ± 1.7 | 0.04 ± 0.04[*,#] |
| Brain stem | 3.3 ± 0.7 | 3.5 ± .09 | 0.05 ± 0.05[*,#] |

*$p < 0.05$ vs. SV-129, #: $p < 0.05$ vs. type 3 mutant mice (Turkey's multiple range test).
NOS catalytic activity was measured by calcium-dependent [$^3$H]arginine to [$^3$H]citruline conversion. The experiment was performed three times in duplicate.

Example 13

Use of the Vessel Injury Models of Atherosclerosis in eNOS Mutant Mice

Both the cuff model and the filament model of vessel injury can be used as an animal model for atherosclerosis. Major features of these two vessel injury models can be seen in the following Table:

TABLE 8

Comparison of Vessel Injury Models

| Feature | Cuff Model | Filament Model |
|---|---|---|
| Exemplary Location | femoral artery | carotid artery |
| Method of Injury | placement of non-occlusive cuff around vessel | insertion of filament to denude endothelial layer |
| Manipulated Area | adventitia | endothelium |
| Response | adventitial inflammation; medical cellular proliferation | removal of endothelium, medical cellular proliferation |
| Time to response | 14–28 days | 14–28 days |
| Measurements | quantitative morphometry; immunohistochemistry; expression studies (RT-PCR); indices of cellular proliferation | quantitative morphometry; immunohistochemistry; expression studies (RT-PCR); indices of cellular proliferation |

The Cuff Model:

Mice aged 7–8 weeks were anesthetized with pentobarbital (50 mg/kg ip). Femoral arteries were surgically exposed and dissected from the surrounding tissue. A non-occlusive polyethylene cuff (2 mm in length, 0.58 mm inner diameter, made of PE-50 tubing split longitudinally) was placed around the left femoral artery and tied snugly with a silk thread. The right femoral artery served as a sham control. The wounds were then closed and the animals allowed to awaken from anesthesia. Animals were euthanized at 3, 14, 21, and 28 days after cuff placement. The femoral arteries were fixed under perfusion in 10% formalin, and embedded in paraffin.

Figure 16:
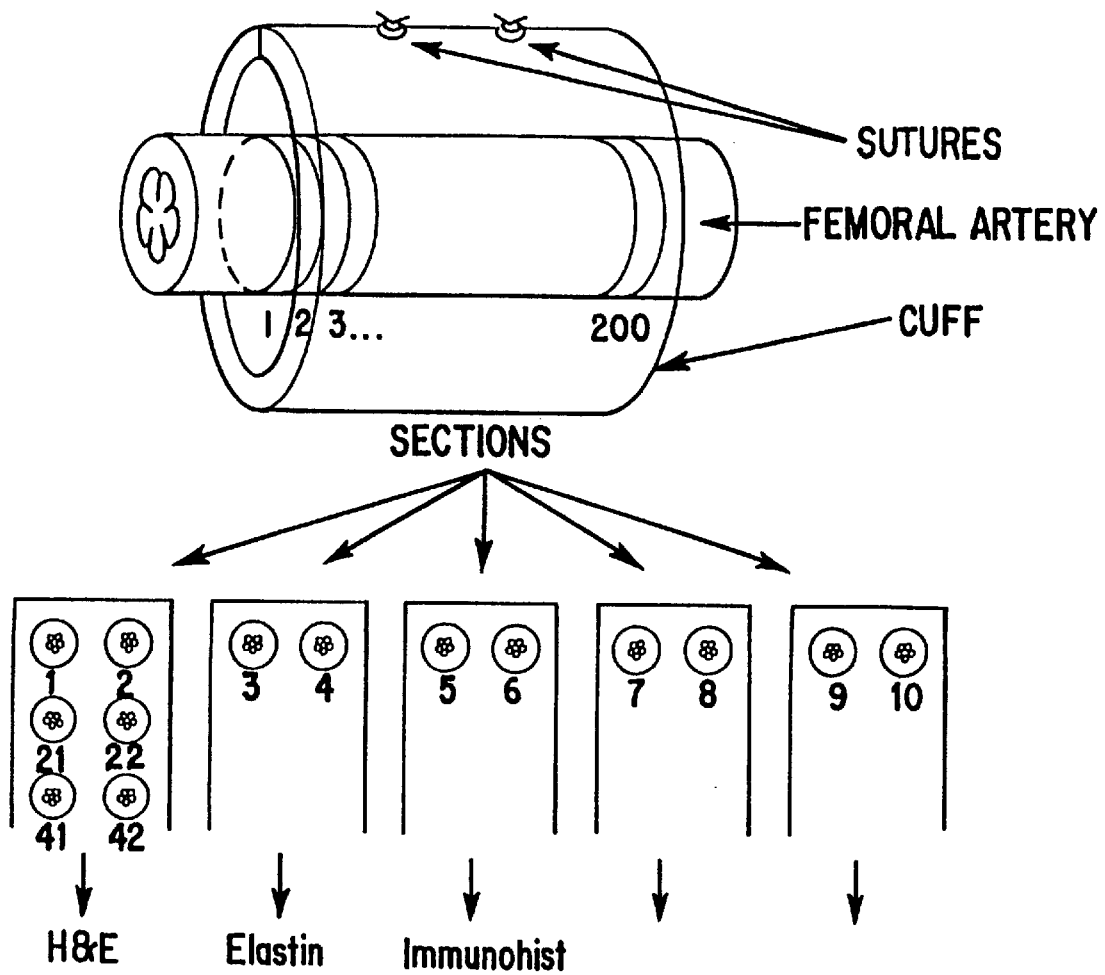
FIG. 16 is a schematic showing the cuff model of vessel injury.
Figure 17A:
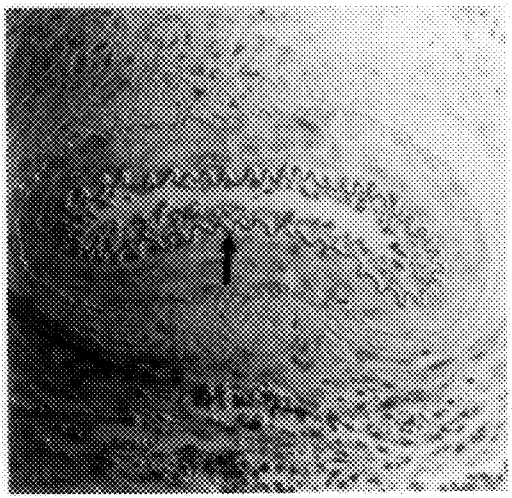
FIGS. 17A–17D depict micrographs of hematoxylin and eosin stained sections of cuff injured vessels. Injured vessels contain neointima seen inside of the internal elastic lamina (shown with arrows). Control vessels do not contain the neointima. Vessels from eNOS mutant mice show significantly increased neointimal formation, which is shown with an asterisk.
Figure 17B:
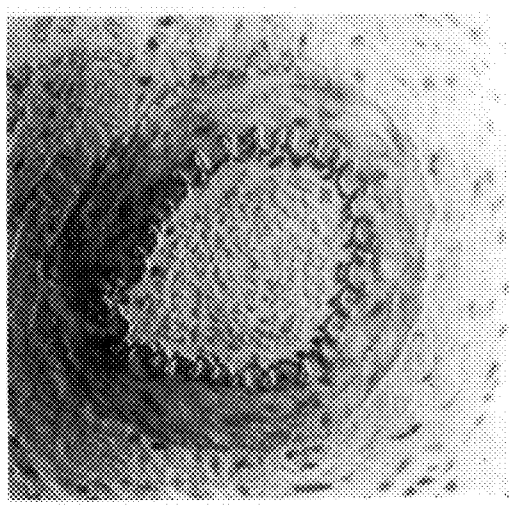
Figure 17C:
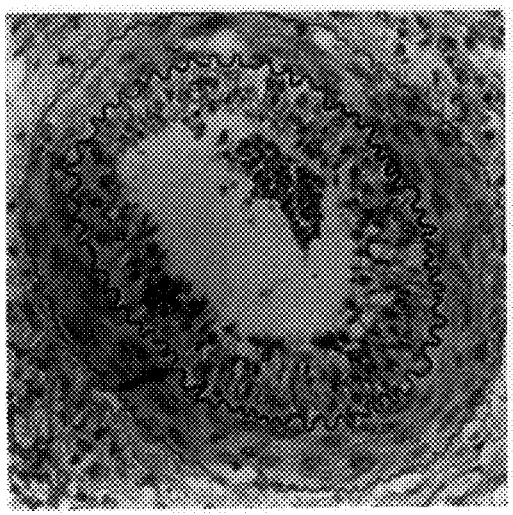
Figure 17D:
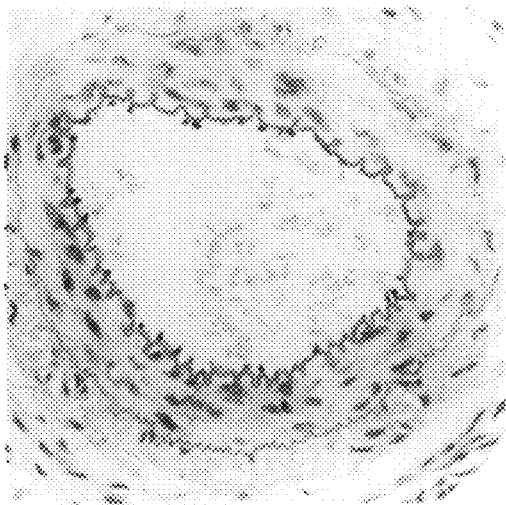
Figure 18A:
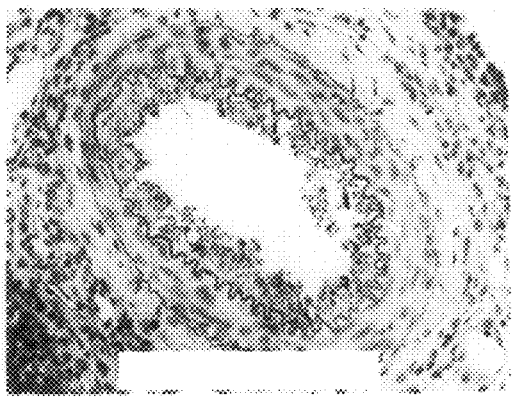
FIGS. 18A–18H depict histology and immunochemical staining of injured and control vessels from eNOS mutant mice. Control vessels have no intima.
Figure 18B:
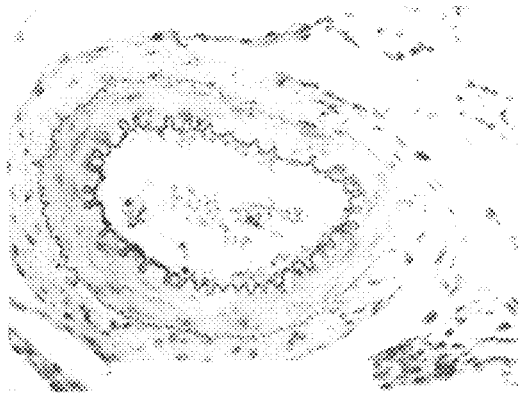
Figure 18C:
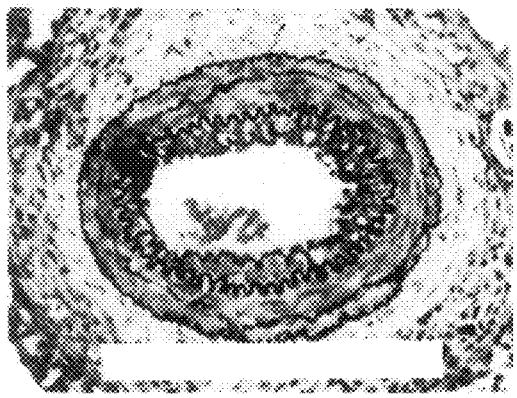
Figure 18D:
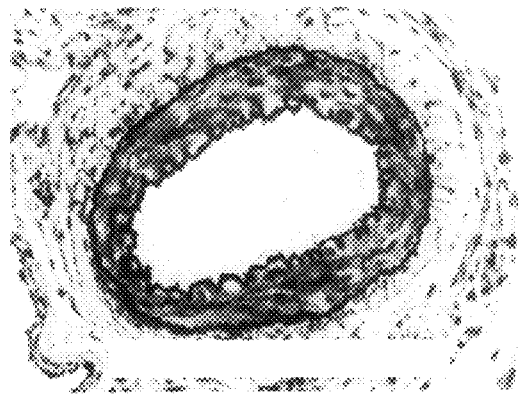
Figure 18E:
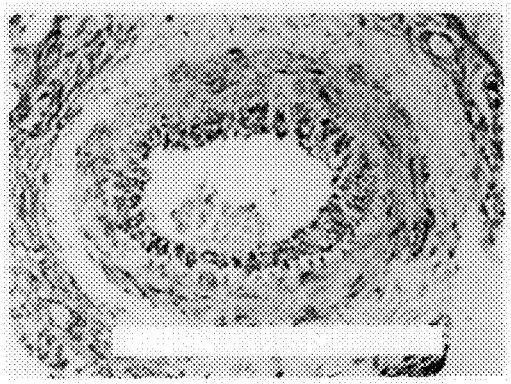
Figure 18F:
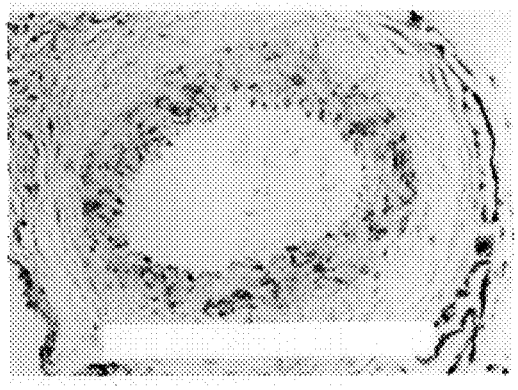
Figure 18G:
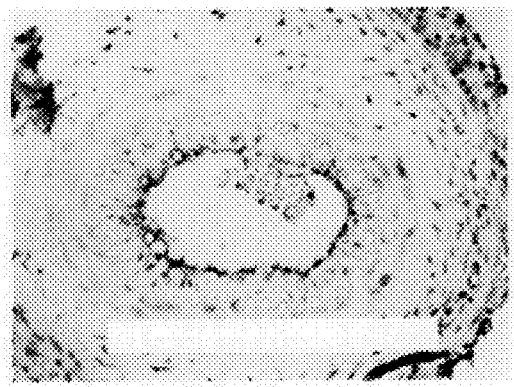
Figure 18H:
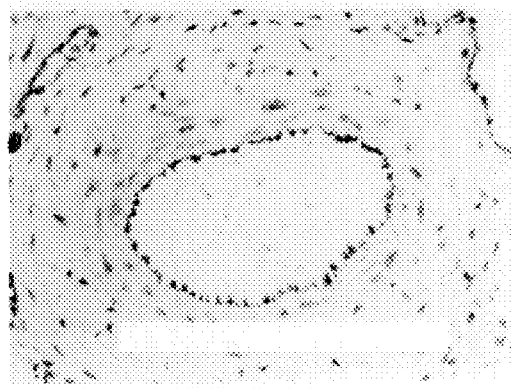

The cuffed vessel segment and the corresponding sham operated vessel were cut into 200 serial 10 $\mu$m sections, and were placed in order on five series of slides, as shown in FIG. 16. One series was stained with hematoxylin-eosin, another with elastin, and the others were saved for immunohistochemistry. The slides were scanned into Adope Photoshop, and the quantitative morphometry was performed using the public domain program NIH Image.

We performed two types of measurements. First, for area/volume measurements, the areas within the lumen, internal elastic lamina, and external elastic lamina were measured. The intimal area was calculated as the difference between the area within the internal elastic lamina and the lumen. The medial area was calculated as the difference between the areas within the external and internal elastic laminae. The areas were integrated over the length of the vessel segment to calculate the volume of intima and media. Second, for thickness measurements, the thickness of the intima and the media at four points located 90° to each other, and averages over the length of the vessel segment.

Table 9 shows the representative data from individual wild-type and eNOS mutant male mice, to indicate the types of measurements and their variance.

These results are summarized in Table 10. Wild-type mice, which have no detectable intima at baseline, develop neointima within 14 days of cuff injury, with an intima to media (I/M) volume ratio of 0.29 for males and 0.18 for females. The eNOS mutant animals developed substantially more neointima, with an I/M volume ratio of 0.73 for males and 0.43 for females. Thus, animals with a disrupted eNOS gene exhibit greater neointimal formation in response to cuff injury. FIG. 17 shows representative section of vessels stained with hematoxylin-eosin. The internal elastic lamina is indicated by arrows, and the degree of neointima formation can be easily seen.

| | | | | | Volume measurements | | | Linear measurements, um | | | | | |
|---|---|---|---|---|---|---|---|---|---|---|---|---|---|
| | | | | | | | | Injured side | | | Control side | | |
| No. | Genotype | Sex | Age | Wt, g. | Intima | Media | I/M ratio | Lum diam | Intima | Media | Lum diam | Intima | Media |
| | | | | | (wild-type male mice) | | | | | | | | |
| 70 | Wild-type | M | 8 | 24.0 | 5.9 | 25.1 | 0.23 | 111.4 | 7.9 | 27.7 | 110.9 | 0 | 28.8 |
| 71 | Wild-type | M | 8 | 23.0 | 7.5 | 23.1 | 0.32 | 210.1 | 5.5 | 15.6 | 166.2 | 0 | 23.5 |
| 72 | Wild-type | M | 8 | 24.0 | 6.5 | 22.8 | 0.28 | 172.8 | 5.8 | 17.9 | 154.9 | 0 | 22.4 |
| 73 | Wild-type | M | 8 | 25.9 | 8.9 | 31.5 | 0.28 | 160.4 | 8.3 | 23.4 | 119.7 | 0 | 29.8 |
| 74 | Wild-type | M | 8 | 26.1 | 5.4 | 23.6 | 0.23 | 198.5 | 4.9 | 17.1 | 211.6 | 0 | 20.0 |
| 75 | Wild-type | M | 8 | 24.3 | 6.7 | 24.5 | 0.27 | 227.3 | 3.2 | 15.6 | 162.6 | 0 | 27.3 |
| 76 | Wild-type | M | 8 | 23.9 | 9.3 | 32.7 | 0.28 | 212.5 | 6.8 | 21.1 | 153.8 | 0 | 20.3 |
| 77 | Wild-type | M | 8 | 25.0 | 6.3 | 26.9 | 0.23 | 142.7 | 6.7 | 23.1 | 183.7 | 0 | 25.8 |
| 78 | Wild-type | M | 8 | 23.0 | 10.7 | 39.5 | 0.27 | 172.5 | 9.3 | 28.6 | 159.2 | 0 | 32.5 |
| 79 | Wild-type | M | 8 | 28.3 | 10.9 | 41.8 | 0.26 | 198.1 | 6.1 | 21.4 | 183.3 | 0 | 27.6 |
| 132 | Wild-type | M | 8 | 26.1 | 11.3 | 35.6 | 0.32 | 182.4 | 6.5 | 18.7 | 176.6 | 0 | 26.9 |
| 133 | Wild-type | M | 8 | 25.2 | 8.1 | 32.8 | 0.25 | 142.7 | 6.7 | 29.9 | 183.7 | 0 | 30.8 |
| 134 | Wild-type | M | 8 | 23.8 | 10.7 | 39.5 | 0.27 | 172.5 | 9.3 | 28.6 | 159.2 | 0 | 31.9 |
| 135 | Wild-type | M | 8 | 25.9 | 8.7 | 25.9 | 0.33 | 150.6 | 8.3 | 24.5 | 180.3 | 0 | 22.3 |
| 136 | Wild-type | M | 8 | 24.8 | 7.6 | 26.4 | 0.29 | 162.6 | 5.1 | 26.6 | 156.1 | 0 | 18.6 |
| 137 | Wild-type | M | 8 | 22.9 | 11.2 | 31.2 | 0.36 | 180.0 | 5.9 | 21.6 | 180.1 | 0 | 20.7 |
| 138 | Wild-type | M | 8 | 26.8 | 7.5 | 28.6 | 0.26 | 195.2 | 6.3 | 19.6 | 196.5 | 0 | 23.9 |
| 139 | Wild-type | M | 8 | 26.3 | 10.2 | 29.2 | 0.35 | 186.3 | 7.0 | 25.4 | 198.5 | 0 | 22.6 |
| 140 | Wild-type | M | 8 | 25.9 | 9.1 | 29.8 | 0.30 | 210.1 | 4.9 | 28.0 | 168.2 | 0 | 23.6 |
| 141 | Wild-type | M | 8 | 22.9 | 8.5 | 23.6 | 0.36 | 175.4 | 8.6 | 24.6 | 145.3 | 0 | 29.0 |
| Mean | | | | | 8.5 | 29.7 | 0.29 | 178.2 | 6.6 | 22.9 | 167.5 | 0 | 25.4 |
| Std. dev. | | | | | 1.9 | 5.8 | 0.04 | 28.3 | 1.6 | 4.5 | 24.7 | 0 | 4.2 |
| | | | | | (eNOS mutant male mice) | | | | | | | | |
| 98 | eNOS −/− | M | 8 | 28.0 | 20.8 | 32.1 | 0.65 | 122.5 | 22.8 | 26.3 | 116.4 | 0 | 27.7 |
| 99 | eNOS −/− | M | 8 | 25.2 | 23.5 | 36.6 | 0.64 | 165.5 | 20.1 | 25.3 | 131.9 | 0 | 27.3 |
| 100 | eNOS −/− | M | 8 | 23.5 | 33.2 | 36.4 | 0.91 | 203.6 | 29.4 | 20.5 | 133.3 | 0 | 25.7 |
| 101 | eNOS −/− | M | 8 | 20.5 | 19.7 | 27.9 | 0.71 | 136.9 | 20.0 | 22.3 | 151.3 | 0 | 31.1 |
| 102 | eNOS −/− | M | 8 | 22.7 | 22.5 | 33.4 | 0.67 | 144.9 | 21.5 | 25.0 | 138.1 | 0 | 33.6 |
| 103 | eNOS −/− | M | 8 | 25.8 | 21.5 | 30.6 | 0.70 | 157.4 | 21.5 | 23.9 | 134.1 | 0 | 30.5 |
| 104 | eNOS −/− | M | 8 | 23.6 | 19.8 | 31.2 | 0.63 | 146.6 | 19.0 | 23.8 | 168.4 | 0 | 29.6 |
| 105 | eNOS −/− | M | 8 | 28.1 | 21.4 | 36.0 | 0.59 | 177.6 | 15.2 | 24.6 | 159.4 | 0 | 28.1 |
| 106 | eNOS −/− | M | 8 | 21.0 | 16.3 | 23.4 | 0.70 | 157.6 | 13.2 | 19.3 | 162.7 | 0 | 26.3 |
| 147 | eNOS −/− | M | 8 | 26.6 | 21.7 | 30.5 | 0.71 | 160.2 | 20.3 | 23.4 | 181.2 | 0 | 24.5 |
| 148 | eNOS −/− | M | 8 | 25.8 | 23.1 | 36.2 | 0.64 | 180.9 | 24.1 | 24.3 | 167.4 | 0 | 22.8 |
| 149 | eNOS −/− | M | 8 | 24.2 | 26.2 | 29.9 | 0.88 | 149.2 | 25.9 | 23.8 | 162.4 | 0 | 23.1 |
| 150 | eNOS −/− | M | 8 | 20.6 | 25.2 | 31.5 | 0.80 | 150.2 | 24.6 | 23.1 | 155.2 | 0 | 23.8 |
| 151 | eNOS −/− | M | 8 | 26.6 | 27.0 | 34.3 | 0.79 | 150.9 | 28.9 | 23.8 | 153.7 | 0 | 24.6 |
| 152 | eNOS −/− | M | 8 | 28.4 | 22.2 | 32.2 | 0.69 | 188.6 | 19.2 | 24.6 | 180.4 | 0 | 24.8 |
| 153 | eNOS −/− | M | 8 | 27.5 | 26.5 | 26.8 | 0.99 | 139.5 | 23.5 | 24.1 | 138.5 | 0 | 28.3 |
| 154 | eNOS −/− | M | 8 | 29.7 | 21.7 | 29.1 | 0.75 | 154.2 | 19.8 | 22.5 | 168.0 | 0 | 21.6 |
| 155 | eNOS −/− | M | 8 | 25.4 | 23.3 | 31.1 | 0.75 | 132.0 | 22.5 | 23.1 | 151.8 | 0 | 25.4 |
| 156 | eNOS −/− | M | 8 | 24.3 | 24.6 | 32.6 | 0.75 | 168.5 | 26.5 | 21.3 | 160.2 | 0 | 22.5 |
| 157 | eNOS −/− | M | 8 | 24.0 | 21.3 | 30.3 | 0.70 | 156.4 | 16.7 | 22.5 | 165.3 | 0 | 27.0 |
| Mean | | | | | 23.1 | 31.6 | 0.73 | 157.2 | 21.7 | 23.4 | 154.0 | 0.00 | 26.4 |
| Std. dev. | | | | | 3.5 | 3.4 | 0.10 | 19.6 | 4.2 | 1.7 | 17.2 | 0.00 | 3.2 |

TABLE 10

Neointima Formation Measured 14 Days After Cuff Placement

| Mouse strain | Intima volume | Media volume | I/M ratio | Intima ($\mu$m) |
|---|---|---|---|---|
| Wild-type, males (n = 20) | 0.0085 ± 0.0019 | 0.0297 ± 0.0058 | 0.29 ± 0.04 | 6.6 ± 1.6 |
| Wild-type, females (n = 20) | 0.0059 ± 0.0018 | 0.0321 ± 0.0087 | 0.18 ± 0.06 | 4.9 ± 1.8 |
| eNOS mutant, males (n = 20) | 0.0231 ± 0.0035 | 0.0316 ± 0.0034 | 0.73 ± 0.10 | 21.7 ± 4.2 |
| eNOS mutant, females (n = 20) | 0.0123 ± 0.0028 | 0.0286 ± 0.0062 | 0.43 ± 0.09 | 11.7 ± 2.7 |

In Table 10, all measurements are expressed as mean ± standard deviation. Volumes are expressed in mm$^3$, and are calculated as outlined in the text from area measurements. The last column shows thickness measurements of intima on the injured side. There was no detectable intima on the control side. p<0.05 was obtained for each gender, eNOS mutant mice vs. wild-type mice by ANOVA followed by Dunnett statistical analysis.

FIG. 18 shows the histology and immunochemical staining of the cuff-injured and control vessels from eNOS mutant mice. Hematoxylin-eosin and elastin stains outline the intima clearly on the injured side; the control has no intima. Cells throughout the neointimal layer stain strongly for actin (E). This staining is also seen in the media of injured and control vessels (E, F), consistent with smooth muscle staining. In contrast, only the luminal cells stain for von Willebrand factor, a marker of endothelial cells, as shown in panels G and H.

The Filament Model:

A comparison of the eNOS mutant mice and wild-type mice using the filament model of vessel injury is performed. As a first step, the size of the carotid arteries of eNOS mutant mice, nNOS mutant mice, and wild-type mice have been quantitated. Carotid arteries were fixed by perfusion at a pressure of 100 mm Hg. The luminal diameter was calculated by dividing the luminal circumference by π to account for differences in luminal shape. As shown in Table 11, the diameters of the carotid artery of wild-type mice do not differ substantially from those of the NOS mutant mice (n=20 in each group). Thus, the filament model can be used with a comparable degree of injury between different mouse strains.

TABLE 11

Luminal diameters of perfusions fixed carotid arteries

|  | Wild-type | eNOS mutant | nNOS mutant |
|---|---|---|---|
| Mean (mm) | 0.42 | 0.45 | 0.41 |
| Std. dev. (mm) | 0.06 | 0.08 | 0.05 |

The filament model addresses eNOS expression by non-endothelial cells, since it removes the endothelial layer of cells. The filament injury model is performed in eNOS mutant mice and C57BL/6 wild-type mice, and morphometry, immunohistochemistry, and BrdU staining is performed as outlined. Briefly, the external carotid artery is identified, and two ligatures are placed around it. The artery is tied distally and a filament is inserted through an incision and advanced down the common carotid artery. The filament is rotated and passed three times. The external carotid artery is tied off proximally, and the right carotid artery serves as a sham operated control.

The process of endothelial resurfacing, which occurs by migration from uninjured areas such as the aortic arch, is also studied. It is expected that the rate of resurfacing of the endothelial layer following denudation will be much slower in eNOS mutant mice.

In order to examine endothelial regeneration, animals are injected with Evan's blue solution (150 $\mu$l of 5% solution in PBS, iv) 10 minutes before euthanasia to identify de-endothelialized segments. Vessel segments are cut open longitudinally and pinned onto Teflon cards with the lumen facing up. For determination of smooth muscle cell proliferation, mice are injected intraperitoneally with 5'-bromo-2'-deoxyuridine (BrdU, 25 mg/kg, Boehringer Mannheim) one hour prior to euthanasia. Immunostaining with antibody to BrdU is carried out.

This result would demonstrate that eNOS expression in both endothelial and non-endothelial cells affect the response to injury. However, if no differences between mutant and wild-type mice are observed, these results would suggest that local production of eNOS by the endothelium and not other cells, is the overriding factor determining vessel response to filament injury.

Two independent methods are used to characterize vessel morphometry: area/volume calculations and thickness measurements of the intima and the media. Intimal, medial, and luminal volumes are calculated by integrating areas along the injured region to ensure that inhomogeneities in neointimal formation along the length of the injured region do not give spurious results. Absolute volumes and intima/media (I/M) ratios are compared. The I/M ratio is a standardized measure that accounts for differences in vessel size, even within the same group of animals.

The effect of hypertension in vascular injury responses (both filament and cuff models) is measured by repeating the experiments after treating eNOS mutant mice with hydralazine to reduce their blood pressure to normotensive levels. The addition of hydralazine to drinking water at 250 $\mu$g/ml gives a daily dose of about 750 $\mu$g, and results in a stable decrease in mean arterial pressure from 102 mm Hg to 72 mm Hg, which is equivalent to the blood pressure of untreated wild-type C57BL/6 mice. This will control hypertension during the duration of the experiment (3 to 28 days). Alternatively, local gene therapy to express eNOS in the femoral artery of the eNOS mutant mice could be used, leaving systemic eNOS deficiency and hypertension unaltered.

Example 14

Quantitative RT-PCR to Study Expression of NOS Isoforms

Primers for RT-PCR detection of NOS isoforms in small amount of tissue from mice have been devised, and are shown below:

```
The nNOS (type I) primers are as follows:
B1 primer: 5' CCT TAG AGA GTA AGG AAG GG GCG GG 3'      (SEQ ID NO:1) (26-mer)
B2 primer: 5' GGG CCG ATC ATT GAC GGC GAG AAT GAT G 3'  (SEQ ID NO:2) (28-mer)
These primers amplify a 404 bp fragment from nNOS cDNA.
The eNOS (type III) NOS primers are as follows:
E1 primer: 5' GGG CTC CCT CCT TCC GGC TGC CAC C 3'      (SEQ ID NO:3) (25-mer)
E2 primer: 5' GGA TCC CTG GAA AAG GCG GTG AGG 3'        (SEQ ID NO:4) (24-mer)
These primers amplify a 254 dp fragment from eNOS cDNA, and an 800 bp
fragment from the eNOS gene.
The iNOS (type II) NOS primers are as follows:
I1 primer: 5' ATC AGG AAC CTG AAG CCC CAG GAC 3'        (SEQ ID NO:5) (24-mer)
I2 primer: 5' TGT TGC CAG ATT TCT CTG CAC GGT 3'        (SEQ ID NO:6) (24-mer)
These primers amplify a 338 bp fragment from iNOS cDNA.
```

These primers are specific, and do not prime cDNA corresponding to the other NOS isoforms.

Figure 19:
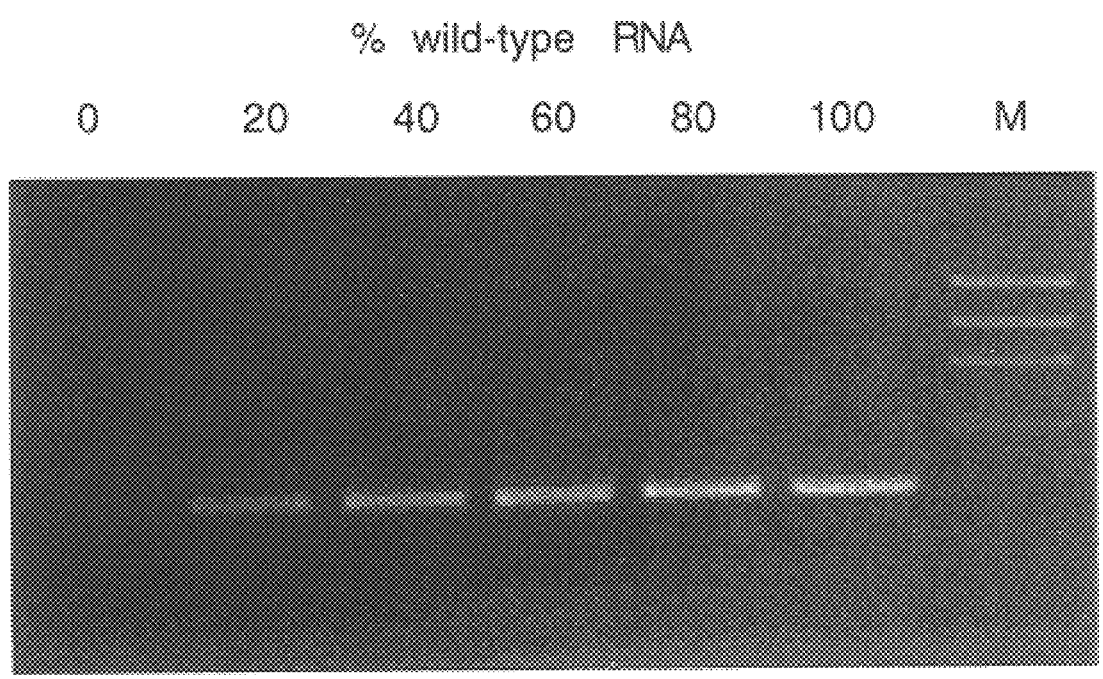
FIG. 19 depicts quantitative RT-PCR of eNOS mRNA from mouse aorta.
Figure 20A:
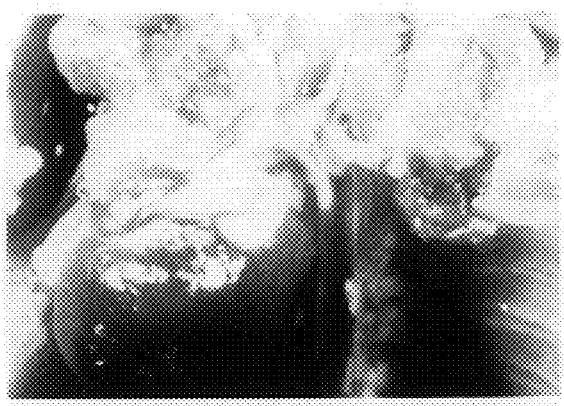
FIGS. 20A–20D depict atherosclerotic lesions from apoE mutant mice at 6 months.
Figure 20B:
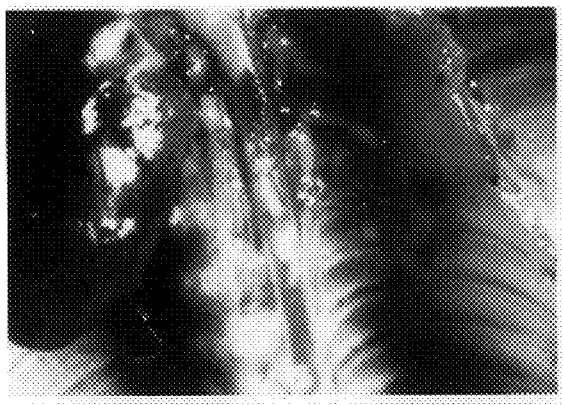
Figure 20C:
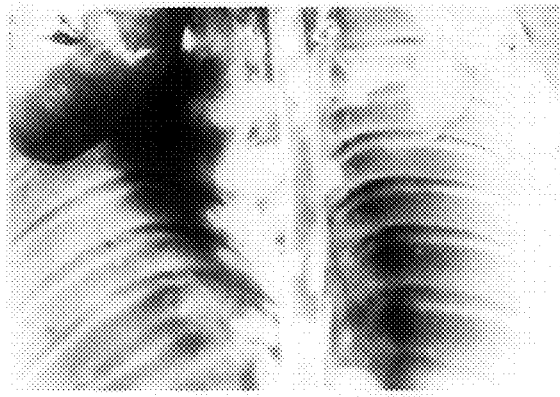
Figure 20D:
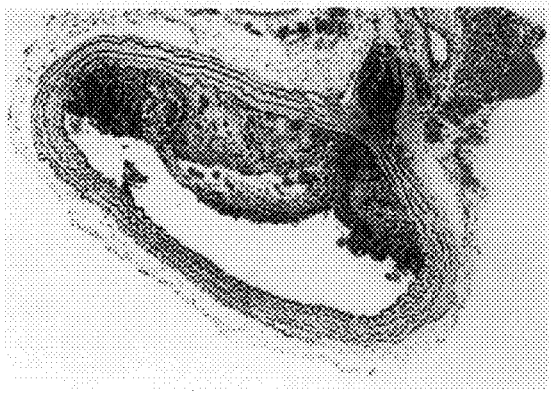

The quantitative nature of this technique was validated by using fixed amounts of aorta RNA (5 μg) as starting material for reverse transcription. Vessels are frozen in liquid nitrogen and homogenized in the presence of phenol and guanidine isothiocyanate (RNAzol B). Total cellular RNA is prepared by extration of the homogenate with chloroform and isopropanol. The proportion of eNOS mutant mRNA to wild-type mRNA varied 100% eNOS mutant (no wild-type mRNA) to 0% eNOS mutant (100% wild-type RNA). Using these mixtures, first strand cDNA was synthesized and used as a template for PCR using the eNOS specific primers. As seen in FIG. 19, the amount of PCR product varied according to the amount of eNOS RNA present in the initial RNA sample, validating the quantitative nature of the reaction. Additional controls for expression of actin and GAPDH were performed as well.

Example 15

ApoE/NOS Mutant Mice

ApoE mutant mice of a C57BL/6 genetic background were obtained from Jackson Labs. These mice were mated to eNOS mutant mice and nNOS mutant mice of the same genetic background. Double heterozygous apoE/eNOS and apoE/nNOS mice have been obtained. Mating pairs of each double heterozygous mice were bred, and the genotype of the offspring is determined using Southern blot analysis. For example, the ApoE mutation is genotyped by digesting genomic DNA with HindIII and using a 0.6 kb SacI/HindIII fragment. A ubiquitous endogenous HindIII band is 7.5 kb, the wild-type band is about 9 kb, and the disrupted band is 3 kb. See Huang (1994); Huang (1995).

The development of atherosclerotic lesions in the aorta of apoE mutant mice have been observed over time. FIG. 20 shows a 6 month old apoE mutant mice with macroscopically visible lesions within the aortic arch, the origins of the carotid arteries, and the thoracic and abdominal aorta Lipid in an aortic lesion stains with oil red O. The apoE mutant mice develop fatty streak lesions by 10 weeks of age, and evolve foam cells and fibrous plaque lesions by 15–20 weeks. The lesions typically occur in regions of shear stress, at the origins of the carotid arteries, intercostal arteries, renal arteries, and aortic bifurcation.

Since the apoE single or double mutant mice develop predictable, spontaneous atherosclerotic lesions, they provide a genetic background on which to study the effect of mutations in other genes, e.g., eNOS. The development of atherosclerotic lesions in mice homozygous for apoE and eNOS mutations is compared vs. apoE mutant mice that are wild-type for eNOS.

The animals will be fed a typical high-cholesterol, high-fat Western-type diet to mimic the human atherosclerotic process. This diet contains 16% crude fat, 1.25% cholesterol (Harlan Teklad Diets, Madison, Wis.). The mice have elevated VLDL and chylomicron levels. The lipid profiles of these mice will also be measured to ensure that eNOS gene disruption does not independently affect the lipid profile.

ApoE and ApoE/eNOS mutant mice are sacrificed at age 5, 10, 20, and 30 weeks. The lungs, liver, stomach, and intestines are removed so that the thoracic and abdominal aorta can be dissected. The tissue is stained with Oil Red O to quantitate the total area of atherosclerotic lesions compared with the area of aorta, from the aortic valve down to 1 cm past the aortic bifurcation. The time points are selected to determine if there is a difference in the rate of lesion development versus the severity of the lesions. The dependence of apoE atherosclerosis on diet demonstrates that these variables can be modulated, and that their quantitation is feasible.

Serial sections are taken for histologic analysis and to quantitate intimal proliferation. The volume of intima is calculated by integrating their affected areas over the length of the affected segment, as described above in the injury models. The cell types involved in these lesions, e.g., smooth muscle, endothelium, and foam cells, are identified by immunohistochemical staining with antibodies for alpha actin, vimentin, factor VIII related antigen, and CD31. The expression of remaining NOS isoforms will be examined by immunocytochemistry, and quantitated by RT-PCR, as described supra.

In other experiments, a low-fat, low-cholesterol diet can be used if the effect of the apoE mutation masks the effect of the eNOS mutation. Alternatively, cholic acid can be added to the diet to increase the atherosclerotic stimulus.

In these experiments, statistical differences in lipid levels among groups are tested by one-way ANOVA, and post hoc tests of individual means are performed with Tukey's test. Differences in atherosclerotic lesion area between groups will be statistically analyzed with the non-parametric Kruskal-Wallis procedure.

Example 16 iNOS and nNOS Isoforms Contribute to the Development of Atherosclerosis

In this Example, iNOS and nNOS mutant mice are used to determine if the loss of these pro-atherogenic isoforms show less response to injury and less atherogenesis. The cuff model of vessel injury is used in iNOS and nNOS mutant mice. These mice have normal vascular anatomy, so their response can be compared with those of wild-type C57BL/6 mice. Quantitative morphometry, immunohistochemistry, indices of cellular proliferation, and NOS isoform studies are performed as part of the filament or cuff injury models as described supra.

Double mutant apoE/iNOS and apoE/nNOS mice are bred to compare the development of atherosclerotic lesions in these animals with apoE mice. A typical high-cholesterol, high-fat Western type diet without cholic acid is used to mimic the human atherosclerotic process. The lipid profiles of these animals are measured, to ensure that the disruption of iNOS or nNOS do not have independent effects on the lipid profile.

The mice are sacrificed at age 5, 10, 20, 25, and 30 weeks. The thoracic and abdominal aorta is stained with Oil Red O, to quantitate the total area of atherosclerotic lesions compared with the area of the aorta. Serial sections are taken for histological analysis and to quantitate intimal proliferation the volume of intima is calculated by integrating the affected areas over the length of the affected segment. The cell types involved in these lesions are identified by immunohistochemical staining, and expression of the remaining NOS isoforms will be examined by immunohistochemistry, and quantitated by RT-PCR.

This experiment extends the results from injury models to the development of atherosclerotic lesions. The development of lesions involves not only cellular differentiation, but also the recruitment of inflammatory cells, lipid oxidation and phagocytosis, and endothelial cell activation. Due to the participation of iNOS or nNOS isoforms in the pathophysiology of atherosclerosis, the disruption of these genes would be expected to result in a less severe phenotype than apoE mutant mice alone.

Example 17

The Effect of NOS Isoform Expression Patterns on Lipid Oxidation and Endothelial Cell Activation Peroxynitrite is formed in biological systems only by the reaction of nitric oxide with superoxide. Since human atherosclerotic lesions contain nitrotyrosine, it is known that at least one isoform of NOS generates nitric oxide and peroxynitrite in atherosclerotic lesions. iNOS and nNOS, but not eNOS, are believed to be involved in the generation of peroxynitrite. If so, iNOS and nNOS mutant mice will exhibit decreased amounts of nitrotyrosine. Therefore, atherosclerotic lesions in animals that lack apoE and each isoform (eNOS/apoE, iNOS/apoE, nNOS/apoE) are examined for the presence of nitrotyrosine.

Two independent methods to detect 3-nitrotyrosine are used: immunohistochemical detection and HPLC. For immunohistochemistry, a rabbit antiserum specific for nitrotyrosine, obtainable from Upstate Biotechnology is used. Alternatively, the level of nitrotyrosine is independently assessed by 16 electrode HPLC. Schultz (1996).

Briefly, tissue from a 50 µm section of brain, comparable to the amount of tissue in atherosclerotic plaques, is used for this analysis. Atherosclerotic plaques from apoE and apoE/NOS double mutant mice are dissected and frozen. The level of 3-nitrotyrosine will be measured by HPLC with 16 electrode electrochemical detection. Reaction of standards and tissue extracts with 1M sodium hydrosulfite should abolish the peaks by converting 3-nitrotyrosine to aminotyrosine. The levels of 3-nitrotyrosine are expressed as a ratio of 3-nitrotyrosine to total tyrosine, to normalize for the varying arterial concentrations of tyrosine. This method is more quantitative than immunohistochemical detection and offers an independent measure of nitrotyrosine formation.

Under physiological conditions, eNOS suppresses the expression of endothelial activation genes by inducing and stabilizing IκB. Peng (1995). In atherosclerotic lesions, NOS expression patterns change, and iNOS and/or nNOS expression increases, while eNOS levels drop. Wilcox (1994). These changes are believed to contribute to increased oxidant stress in the vessel wall, and endothelial cell activation. To test for endothelial cell activation, the expression of VCAM-1 can be used as a preferred marker, since its expression is longer lived than other markers. However, ICAM-1, E-selectin and MCP-1 can be used. eNOS mutant mice will exhibit greater expression of VCAM-1 (more endothelial activation) in atherosclerotic lesions, while iNOS and nNOS would be expected to show diminished VCAM-1 expression (less endothelial activation).

VCAM-1 expression is examined by two methods: immunohistochemistry and RT-PCR quantitation of mRNA expression. For immunohistochemistry, a rat monoclonal anti-VCAM-1 antibody obtained from Southern Biotechnology Associates, Inc., Birmingham, Ala., is used as the primary antibody, and biotinylated goat anti-rat antibody as a secondary antibody. For RT-PCR primers that amplify VCAM-1 cDNA, conditions are used that ensure that the amount of amplified PCR product is proportional to the level of mRNA. Actin mRNA will be used to standardize the amount of total mRNA, and internal quantitative standards will be employed as described supra.

Lipid peroxidation results in many changes, including altered electrophoretic mobility and modification of apolipoprotein B. Many of these can be assessed in purified LDL that has been subject to oxidation, but are more difficult to study in vivo. The protein modification epitopes malondialdehyde-lysine (MDA-lysine) and 4-hydroxynonenal-lysine (4HNE-lysine) as markers for lipid oxidation events. Palinski et al. (1989); Palinski et al. (1994); Itabe et al. (1994); Yla-Herttuala (1989). These epitopes are found in atherosclerotic lesions in apoE-deficient mice and humans. A panel of antibodies against MDA-lysine and 4-HNE epitopes is used to study whether the absence of any one of the NOS isoforms results in a reduction in staining, implicating that NOS isoform in lipid oxidation. These results are correlated with a histologic assessment-of lesion extent, severity, and the presence of foam cells, macrophages, and other inflammatory cells. Independent methods to measure the same process are used, e.g., HPLC for nitrotyrosine or RT-PCR for VCAM-1 expression to improve our ability to detect differences due to NOS isoform deletion.

Literature Cited[1]

Aji et al. (1997), *Circulation* 95:430–437.

Archer, S., (1993), *FASEB J.* 7:349–360.

Babbedge et al. (1993), *Br. J. Pharmacol.* 110:225–228.

Bath (1993), *Eur. J. Clin. Pharmacol.*, 45:53–58.

Beckman et al. (1994a), *Methods Enzymol.* 233:229–240.

Beckman et al. (1994b), *Biol. Chem. Hoppe-Seyler* 375:81–88.

Benditt et al. (1973), *Proc. Natl. Acad. Sci. (USA)* 70:1753–1756.

Boeckvstaens et al. (1991), *Br. J. Pharmacol.* 102:434–438.

Bohme et al. (1991), *Eur. J. Pharmacol.* 199:379–381.

Booth et al. (1989), *Atherosclerosis* 76:257–268.

Bredt et al. (1994), *Ann Rev. Biochem.* 63:175–195.

Bredt et al. (1992), *Neuron* 8:3–11.

Bredt et al. (1990a), *Nature* 347:768–770.

Bredt et al. (1990b), *Proc. Natl. Acad. Sci. USA.* 87:682–685 (1990)—129/130

Breslow (1996), *Science* 272:685–688.

Brinster et al. (1985), *Cell* 27: 4438–4442.

Bult et al. (1990) *Nature* 345: 346–347.

Burnett et al. (1992), *Science* 257: 401–403.

Busse et al. (1996), *J. Vasc. Res.* 33: 181–194.

Curran et al. (1989), *J. Exp. Med.* 170:1769–1774.

Dalkara et al. (1994), *Brain Pathol.* 4:49–57.

Dalkara et al., (1995), *J Cereb Blood Flow Metab.* 15:631–638.

Darley-Usmar et al. (1992), *Free Rad. Res. Commun.* 17:19–20.

Dawson et al., (1991) *Proc Natl Acad Sci USA.* 88:6368–6371.

Dawson et al. (1992), *Ann. Neurol.* 32: 297–311.

Desai et al. (1991), *Nature* 351:477–479.

Dimmeler et al. (1992), *J. Biol. Chem.* 267: 16771–16774.

Dinerman et al. (1994), *Proc. Natl. Acad. Sci. (USA)* 91:4214–4218.

Edelman & Gally (1992), *Proc. Nat'l. Acad. Sci. (USA)* 89:11651–11652.

Furchgott et al. (1980), *Nature* 288:373–376.

Furchgott (1988), Studies on the relaxation of the rabbit aorta by sodium nitrate:basis for the proposal that the acid-activatable component of the inhibitory factor from retractor penis is inorganic nitrate and the endothelium-derived relaxing factor is nitric oxide, In: *Mechanisms of Vasodilation*, P. M. Vanhoutte ed.

Furchgott & Vanhoutte (1989), *FASEB J.* 3: 2007–2018.

Gally et al. (1990), *Proc. Nat'l Acad. Sci. (USA)* 87:3547–3551.

Garcia et al. (1993), *Am J Pathol.* 142:623–635.

[1] All of the literature cited in this application is expressly incorporated herein by reference.

Gibson et al. (1990), *Br. J. Pharmacol.* 99: 602–606.

Gillespie et al. (1989), *Br. J. Pharmacol.* 98: 1080–1082.

Haley et al. (1992), *Neuron* 8: 211–216.

Hamberg et al. (1993) In: *Proceedings of the Society of Magnetic Resonance in Medicine*, 12th Annual Scientific Meeting, Society of Magnetic Resonance in Medicine NY. 1:397.

Hevel et al. (1994), *Methods Enzymol.* 233:250–258 (1994).

Hibbs et al. (1988), *Biochem. Biophys. Res. Comm.* 157: 87–94.

Huang et al. (1993), *Cell* 75:1273–1286.

Huang et al. (1994), *Science* 265:1883–1885.

Huang et al. (1995), *Nature* 377:239–242.

Iadecola et al. (1994), *J Cereb Blood Flow Metab.* 14:175–192.

Ignarro et al. (1988), *Proc. Natl. Acad. Sci. USA.* 84:9265–9269.

Ignarro (1989), *FASEB J.* 3: 31–36.

Ishibashi et al., *J. Clin. Invest.* 92: 883–893.

Itabe et al. (1994), *J. Biol. Chem.* 269:15274–15279 (1994).

Jannsens et al. (1992), *J. Biol. Chem.* 267:14519–14522, and erratum published in *J. Biol. Chem.* 267:22694.

Kano et al. (1991), *J Cereb Blood Flow Metab.* 11:628–637.

Kaufman et al. (1995), Handbook of *Molec. and Cell. Methods in Biol. and Medicine*, pp. 329–366.

Kidd et al. (1995), *Neuropharmacol.* 34:63–73.

Knowles et al. (1992), *Trends Biochem Sci.* 17:399–402.

Kockx et al. (1993), *Arterioscl. Thromb.* 13: 1874–1884.

Koketsu et al. (1992), *J Cereb Blood Flow Metab.* 12:613–620.

Kots et al. (1992), *FEBS Lett.* 300: 9–12.

Kubes et al. (1991), *Proc. Natl. Acad. Sci. USA.* 88:4651–4655.

Kurose et al. (1994), *Circ Res.* 74:376–382.

Lamas et al. (1992), *Proc. Natl. Acad. Sci. (USA)* 89:6348–6352.

Lefer et al. (1993), *Arterioscler. Thromb.* 13:1874–1884.

Leitinger et al. (1995), *J. Physiol. Pharmacol.* 46: 385–408.

Li et al. (1992), *Cell* 69: 915–926.

Linder et al. (1993), *Circ. Res.* 73:792–796.

Lowenstein & Snyder (1992), *Cell* 70: 705–707.

Malinski et al., *J. Cereb. Blood Flow Metab.* 13: 355–358.

Marletta (1989), *Trends Biochem. Sci.* 14: 488492.

Marletta (1993), *J. Biol. Chem.* 268: 12231–12234.

Mayer et al. (1994), *Neuropharmacol.* 33:1253–1259.

McDonald & Moss (1993), *Proc. Nat'l Acad. Sci (USA)* 90: 6238–6241.

Michel et al. (1993), *Br. J. Pharmacol.* 109:287–288.

Moncada (1992), *Acta Physiol. Scand.* 145:201–227.

Moncada et al. (1991), *Pharmacol. Rev.* 43: 109–142.

Moore et al. (1993a), *Br. J. Pharmacol.* 108:296–297.

Moore et al. (1993b), *Br. J. Pharmacol.* 110:219–224.

Mooradian et al. (1995), *J. Cardiovasc. Pharmacol.* 25: 674–678.

Morikawa et al. (1994a), *Stroke.* 25:429–435.

Morikawa et al. (1994b), In: *The human brain circulation* (J Bevens, eds.), Harbor Basin Conference, Vermont. 373–387.

Murphy et al. (1993), *Trends Neurosci.* 16:323–328.

Nathan (1992), *FASEB J.* 6: 3051–3064.

Nathan & Xie (1994), *Cell* 278:915–918.

Nozaki et al. (1993), *J. Cereb. Blood Flow Metab.* 13: 70–79.

O'Dell et al. (1991), *Proc. Nat'l Acad. Sci. (USA)* 88: 11285–11289.

O'Dell et al. (1994), *Science.* 265:542–546.

Palinski et al., *Proc. Natl. Acad. Sci. (USA)* 86:1372–1376 (1989).

Palinski et al., *Arterioscler. Thromb.* 14:605–616 (1994).

Palmer et al. (1987), *Nature* 327: 524–526.

Palmer et al. (1988), *Nature.* 333:664–666.

Peng et al. (1995), *J. Biol. Chem.* 270: 14214–14219.

Plump et al. (1992), *Cell* 71:343–353.

Purcell-Huynh et al. (1995), *J. Clin. Invest.* 95: 2246–2257.

Radomski et al. (1991), *Trends in Pharm. Sci.* 12:87–88.

Radomski et al. (1995), *Atherosclerosis* 18: S69–80.

Rajfer et al. (1992), *N. Engl. J. Med.* 326: 90–94.

Ramagopal & Leighton (1989), *Eur. J. Pharmacol.* 174: 297–299.

Ramdomsky et al. (1990), *Proc Natl Acad Sci USA.* 87:5193–5197.

Rees et al. (1990), *Br J Pharmacol.* 101: 746–752.

Remington's Pharmaceutical Sciences, Mack Publishing Co., Easton, Pa. (1990).

Ross (1996), *Nature Medicine* 2:527–528.

Ross (1995), *Ann. Rev. Physiol.* 57:791–804.

Rutherford et al. (1995), Br. J. Pharmacol. 116:3099–3109.

Schmidt & Walter (1994), *Cell* 78:919–925.

Schmidt et al. (1992), *J. Histchem. Cytochem.* 40:1439–1456.

Schultz et al.(1996), *J. Neurochem.* 67:430–433.

Schulz et al. (1995a), *J. Neurochem.* 64:936–939.

Schulz et al. (1995b), *J. Neurosci.* 15: 8419–8429.

Schuman & Madison (1991), *Science* 254: 1503–1506.

Schwartz et al. (1995), *Circulation Res.* 77: 445–465.

Shibuki & Okada (1991), *Nature* 349: 326–328.

Snyder et al. (1991), *Trends Pharmacol Sci.* 12:125–128.

Snyder (1992), *Science* 257: 494–496.

Snyder (1995), *Nature* 377:196–197.

Sobey et al. (1995), *Circ. Res.* 77: 536–543.

Toda & Okamura (1990), *Biochem. Biophys. Res. Comm.* 170: 308–313.

Topors et al. (1995), *Circulation* 92:I-564.

Tottrup et al. (1991), *Am. J. Physiol.* 260:G385–G387.

Tybulewicz et al. (1991), *Cell* 65: 1153–1163.

van den Maagdenberg et al. (1993), *J. Biol. Chem.* 268: 10540–10545.

Vincent et al. (1992), *Neurosci* 46:755–784.

Wallace et al. (1992), *NeuroReport* 3:953–956.

Wilcox et al. (1994), *Circulation* 90 (supp I):I-298.

Yamamoto et al.(1992), *J Cereb Blood Flow Metab.* 12:717–726.

Yang et al. (1994), *Stroke* 25:165–170.

Yla-Herttuala et al.,*J. Clin. Invest.* 84:1086–1095 (1989).

Yoshida et al. (1994), *J Cereb Blood Flow Metab.* 14:924–929.

Yoshida et al.(1995), *Neuroscience Letter.* 194:214–218.

Zea-Longa et al.(1989), *Stroke.* 20:84–91.

Zhang et al. (1992), *Science* 258:468–471.

Zhang et al. (1993), *NeuroReport.* 4:559–562.

Zhang et al.(1994), *J Cereb Blood Flow Metab.* 14:217–226.

Zhang et al. (1995), *J Cereb Blood Flow Metab.* 15(Suppl.):S90.

Zhang & Snyder (1992), *Proc. Nat'l Acad. Sci (USA)* 89: 9387–9385.

---

What is claimed is:

1. A cell line comprising one or more cells comprising a disrupted eNOS gene, wherein in substantially all of said cells both copies of said eNOS gene are disrupted.

2. The cell line as claimed in claim 1, wherein said cell line is selected from the group consisting of a tumor cell line, an endothelial cell line, an epithelial cell line, a leukocyte cell line, a neural cell line, a macrophage cell line, a glial cell line, and a muscle cell line.

* * * * *